(12) United States Patent
Sartipy et al.

(10) Patent No.: US 8,802,431 B2
(45) Date of Patent: Aug. 12, 2014

(54) POPULATION OF MULTIPOTENT CARDIAC PRECURSOR CELLS DERIVED FROM HUMAN BLASTOCYSTS DERIVED STEM CELLS

(75) Inventors: Peter Sartipy, Kungsbacka (SE); Karolina Åkesson, Göteborg (SE); Caroline Améen, Göteborg (SE)

(73) Assignee: Cellectis AB, Gothenburg (DE)

( * ) Notice: Subject to any disclaimer, the term of this patent is extended or adjusted under 35 U.S.C. 154(b) by 1109 days.

(21) Appl. No.: 12/308,767

(22) PCT Filed: Jul. 13, 2007

(86) PCT No.: PCT/EP2007/006239
§ 371 (c)(1),
(2), (4) Date: Jan. 28, 2009

(87) PCT Pub. No.: WO2008/006605
PCT Pub. Date: Jan. 17, 2008

(65) Prior Publication Data
US 2010/0009399 A1 Jan. 14, 2010

Related U.S. Application Data

(60) Provisional application No. 60/830,334, filed on Jul. 13, 2006.

(30) Foreign Application Priority Data

Jul. 13, 2006 (DK) .................................. 2006 00970

(51) Int. Cl.
C12N 5/071 (2010.01)
C12N 5/00 (2006.01)
C12N 5/02 (2006.01)

(52) U.S. Cl.
USPC ............................ 435/366; 435/325; 435/377

(58) Field of Classification Search
USPC .......................................... 435/366, 325, 377
See application file for complete search history.

(56) References Cited

FOREIGN PATENT DOCUMENTS

| WO | WO 03/006950 A3 | 1/2003 |
| WO | WO 03/055992 A2 | 7/2003 |
| WO | WO 2004/098285 A2 | 11/2004 |
| WO | WO 2004/099394 A2 | 11/2004 |
| WO | WO 2005/012510 A1 | 2/2005 |
| WO | WO 2006/052925 A2 | 5/2006 |

OTHER PUBLICATIONS

Martin et al., Genes & Dev., 24: 2778-2783, 2010.*
Gokhale et al., Cell Growth and Differentiation, 11: 157-162, 2000.*
"Vimentin" and "Desmin" www.mubio.com, accessed online on Nov. 29, 2011.*
Hoffman et al.(Nature Biotech., 23(6): 699-708, 2005.*
Heins, N., et al., "Derivation, characterization, and differentiation of human embryonic stem cells" Stem Cells, 2004;22:367-76.
Huber, T. et al., "Transcriptional regulation of blood formation during Xenopus development," Seminars in Immunology,1998; 10(2):103-109.
Noaksson, K., et al., "Monitoring differentiation of human embryonic stem cells using real-time PCR," Stem Cells, 2005; 23(10):1460-7.
Norström, A., et al.,"Molecular and pharmacological properties of human embryonic stem cell-derived cardiomyocytes," Exp Biol Med (Maywood), Dec. 2006;231(11):1753-62.
Sjogren-Jansson, E., et al., "Large-scale propagation of four undifferentiated human embryonic stem cell lines in a feeder-free culture system," Developmental Dynamics. Aug. 2005;233(4):1304-14.
Reynolds, B.A., et al., "Generation of neurons and astrocytes from isolated cells of the adult mammalian central nervous system," Science Mar. 1992; 255: 1707-1710.
Urbanek, K., et al., "Intense myocyte formation from cardiac stem cells in human cardiac hypertrophy," PNAS Sep. 2003, 100 (18): 10440-45.
Laugwitz, K-L., et al., "Postnatal isl1+ cardioblasts enter fully differentiated cardiomyocyte lineages," Nature Feb. 2005; 433: 647-653.
Messina, E., et al., "Isolation and expansion of adult cardiac stem cells from human and murine heart," Circ. Res. 2004; 95: 911-921.
Beltrami, A.P., et al., "Adult cardiac stem cells are multipotent and support myocardial regeneration," Cell 2003 114: 763-776.

(Continued)

Primary Examiner — Thaian N Ton
(74) Attorney, Agent, or Firm — Buchanan Ingersoll & Rooney PC

(57) ABSTRACT

A novel population of multipotent cardiac precursor (MCP) cells derived from human blastocysts derived stem cells is disclosed, methods for the preparation thereof and use of the cells for in vitro testing. Basement cells derived from hBS cells are also disclosed and method for the preparation of MCP cells from basement cells. The MCP cells have the following characteristics
i) at least 1% of the cells exhibit no antigen expression of one or more markers for undifferentiated cell, the marker being selected from the group consisting of SSEA-3, SSEA-4, TRA-1-60, TRA-1-81 and Oct-4,
ii) at least 1% of the cells exhibit no protein expression of one or more of a neural marker including nestin or GFAP
iii) at least 1% of the cells exhibit protein and/or gene expression of one or more of a mesodermal marker including brachyury, vimentin or desmin
iv) at least 1% of the cells exhibit protein and/or gene expression of Flk-1 (KDR).
Furthermore, the MCP cells have a characteristic morphology. They grow as clusters of small, round and phase-bright cells; individual cells are 5-20 µm in diameter and each cluster is composed of 2-500 cells. They form clusters of round or elongated shape, that appear as loosely adherent cell clumps that as illustrated in FIG. 2 panel a, b and c. Furthermore, they have a relatively high nucleus-to-cytoplasma ratio, e.g. 1:2-1:64 of the total volume of the cell and/or appear as balloons on a string, as illustrated in FIG. 18, schematic sketch. Moreover, the MCP cells are non-contracting.

2 Claims, 25 Drawing Sheets

(56) References Cited

OTHER PUBLICATIONS

Figure 1:
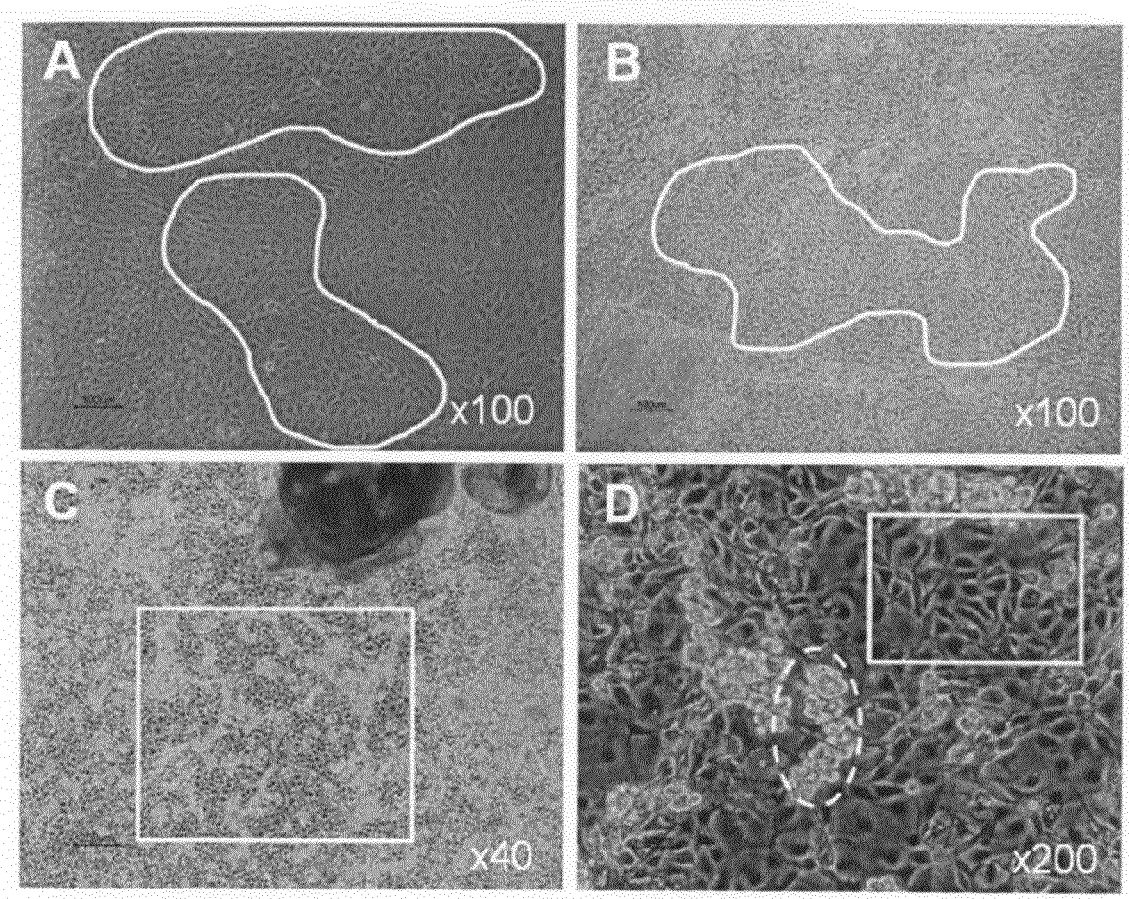

Cai, C.-L., et al., "Isl1 identifies a cardiac progenitor population that proliferates prior to differentiation and contributes a majority of cells to the heart," *Developmental Cell* 2003. 5: 877-889.

Kehat, I., et al., "Human embryonic stem cells can differentiate into myocytes with structural and functional properties of cardiomyocytes," *J. Clin. Invest.* Aug. 2001; 108: 407-414.

Xu, C., et al., "Characterization and enrichment of cardiomyocytes derived from human embryonic stem cells," *Circ. Res.* 2002; 91: 501-508.

He. J.-Q., et al., "Human embryonic stem cells develop into multiple types of cardiac myocytes: action potential characterization," *Circ. Res.* 2003; 93: 32-39.

Mummery, C., et al., "Differentiation of human embryonic stem cells to cardiomyocytes: role of coculture with visceral endoderm-like cells," *Circulation* 2003; 107: 2733-2740.

International Search Report issued in PCT/EP2007/006239 dated Apr. 21, 2008.

Yoon, B.S., et al., "Enhanced differentiation of human embryonic stem cells into cardiomyocytes by combining hanging drop culture and 5-azacytidine treatment," *Differentiation*, 2006; 74:149-159.

Gepstein, L., "Derivation and Potential Applications of Human Embryonic Stem Cells," *Circulation Research*, 2002; 81:866-876.

Oh, S.K., et al., "Derivation and Characterization of new Human Embryonic Stem Cell Lines: SNUhES1, SNUhES2, and SNUhES3," *Stem Cells*, 2005; 23:211-219.

Zheng, B., et al., "hhLIM is Involved in Cardiomyogenesis of Embryonic Stem Cells," *Biochemistry*, 2006, vol. 71, Suppl. 1, pp. 571-576; Pleiades Publishing, Inc., Moscow.

T. Barberi et al., *Derivation of Multipotent Mesenchymal Precursors from Human Embryonic Stem Cells*, 2(6) PLoS Medicine 0554-0560 (Jun. 2005).

P. Gokhale et al., *Brachyury is Expressed by Human Teratocarcinoma Cells in the Absence of Mesodermal Differentiation*, 11 Cell Growth & Differentiation 157-162 (Mar. 2000).

L. Hoffman et al., *Characterization and culture of human embryonic stem cells*, 23(6) Nature Biotechnology 699-708 (Jun. 2005).

E. Kolossov et al., *Functional Characteristics of ES Cell-derived Cardiac Precursor Cells Identified by Tissue-specific Expression of the Green Fluorescent Protein*, 143(7) The Journal of Cell Biology 2045-2056 (Dec. 28, 1998).

B. Martin et al., *Brachyury establishes the embryonic mesodermal progenitor niche*, 24 Genes and Development 2778-2783 (2010).

Background Vimentin and Desmin, http:www.mubio.com, accessed Nov. 29, 2011.

* cited by examiner

POPULATION OF MULTIPOTENT CARDIAC PRECURSOR CELLS DERIVED FROM HUMAN BLASTOCYSTS DERIVED STEM CELLS

FIELD OF THE INVENTION

The present invention relates to a novel multipotent cardiac precursor (MCP) cell population derived from hBS cells and to the potential use of such MCP cells in e.g. medical treatment, pharmaceutical drug development, cell therapy and toxicity testing.

Furthermore, the MCP cells have the capacity to differentiate into spontaneously contracting cardiomyocyte-like cells which make them attractive for use in in vitro studies of cardiogenesis such as early cardiomyogenic processes or cardio-regenerative disorders or malformations.

The MCP cells are obtained after cultivation of so-called basement cells derived from hBS cells as well. Accordingly, the invention also relates to these basement cells that have proven to be capable of providing MCP cells.

BACKGROUND OF THE INVENTION

Cardiovascular diseases are responsible for a large amount of deaths around the world and are a major burden on the health care system. Cardiac transplantation is still the best treatment available for end-stage heart disease. However, besides the high costs for this intervention, restrictions of the procedure relate to the sides effects derived from the use of immunosuppressants and the limited availability of organ donors. Among other possibilities, cell transplantation has emerged as a novel tentative option to stimulate myocardial regeneration. By reducing the need for organs, cell-based treatments will be of great importance to both society and to the individuals suffering from severe degenerative diseases such as cardiac infarction.

The traditional view of the heart as a post-mitotic organ has been challenged during the past few years and myocytes turnover as well as the presence of stem/progenitor cells residing in the adult mammalian heart has been described (Urbanek et al PNAS 2003, 100 (18), 10440-45, Laugwitz et al Nature, 2005, 433, 647-653, Messina et al Circ Res 2004, 95, 911-921, Beltrami et al Cell, 2003, 114, 763-776, Cai et al Dev Cell 2003, 5, 877-889). A number of different tissues have been proposed as the source of stem cells able to generate new cardiomyocytes (e.g. fetal cardiomyocytes, skeletal myoblasts, bone-marrow derived stem cells, stem cells isolated from umbilical cord blood, adipose tissue derived stem cells, and embryonic stem cells). So far only embryonic stem cells have been shown in vitro to efficiently differentiate into spontaneously contracting cardiomyocyte-like cells (Kehat et al J Clin Invest, 108: 407-414, 2001, Xu et al Circ Res, 91: 501-508, 2002, He et al Circ Res, 93: 32-39, 2003, Mummery et al Circulation, 107: 2733-2740, 2003). However, derivation and isolation of cardiac stem cells or MCP cells from human blastocyst stem cells have not been previously described. Notably, MCP cells are immature cells that not yet have acquired the functional features of cardiomyocyte-like cells.

On the other hand, cardiac stem cells were reportedly isolated from human post-natal heart biopsies and propagated in tissue culture (Messina et al Circ Res 2004, WO2005/012510 A1, WO2006/052925 A2). These cells were clonogenic, expressed stem and endothelial cell markers (e.g. c-kit, CD-34, Sca-1), and were able to differentiate into myocytes, endothelial and smooth muscle cells in vivo. These isolations however are depending on the accessibility to human biopsies and surgical techniques for their retrieval.

A number of reports have demonstrated the capacity of human embryonic stem cells to differentiate into contracting myocytes but no report has so far identified and isolated a discrete intermediate cardiac progenitor cell population from human embryonic stem cells.

There is a great need for a simple non-surgical method for derivation, isolation, and expansion of cardiac progenitor cells for subsequent use in pharmaceutical drug development, toxicity testing, and cellular therapy.

BRIEF DESCRIPTION OF THE INVENTION

The present invention relates to multipotent cardiac precursor (MCP) cells and the methods for their preparation from hBS cells. In addition, it relates to a specific basement cell type from which the MCP cells originate. The MCP cells of the present invention are especially well suited for use in drug discovery, toxicity testing, and cellular therapies because of their intrinsic capacity of differentiating into spontaneously contracting cardiomyocyte-like cells.

Accordingly, in one aspect the invention relates to a cell population derived from human blastocyst-derived stem (hBS) cells comprising multipotent cardiac precursor (MCP) cells as well as to the MCP cells as such. MCP cells are easy to identify based on morphological characterization and furthermore, a cell population comprising MCP cell have the following characteristics:
  i) at least 1% of the cells exhibit no antigen expression of one or more markers for undifferentiated cell, the marker being selected from the group consisting of SSEA-3, SSEA-4, TRA-1-60, TRA-1-81 and Oct-4,
  ii) at least 1% of the cells exhibit no protein expression of one or more of a neural marker including nestin or GFAP
  iii) at least 1% of the cells exhibit protein and/or gene expression of one or more of a mesodermal marker including brachyury, vimentin or desmin
  iv) at least 1% of the cells exhibit protein and/or gene expression of Flk-1 (KDR).

Furthermore, at least 1% of the cells exhibit no protein expression of one or more early stage cardiac marker such as, e.g., islet-1, cTNI, cTNT, Nkx2.5, alpha-MHC or connexin 43.

An important characteristics of the MPC cells are that they are non-contracting and that they have a very specific morphology as described herein.

As will be apparent from the disclosure herein, MCP cells are derived from so-called basement cells. The basement cells are obtainable by subjecting hBS cells to a suspension culture or a forced aggregation method comprising a differentiation factor or medium for a relatively short period. From this suspension culture, cells are plated and proliferated and a monolayer of basement cells appears. After further culturing, clusters of MCP cells appear as balloons on a string.

As the basement cells are an important intermediate product in order to obtain MCP cells, the present invention also relates to a cell population comprising basement cells as well as to basement cells as such.

In separate aspects, the invention relates to cardiomyocyte-like cells derived from MCP cells and to the use of basement cells, MCP cells and the cardiomyocyte-like cells in drug discovery, drug screening, medicine etc. Furthermore, the invention relates to methods for obtaining the cell populations.

DETAILED DESCRIPTION OF THE INVENTION

Definitions and Abbreviations

As used herein, the term ASA is intended to mean Acetyl Salicylic Acid, which is the active substance in aspirin.

As used herein, the term "blastocyst-derived stem cell" is denoted BS cell, and the human form is termed "hBS cells". In literature the cells are often referred to as embryonic stem cells, and more specifically human embryonic stem cells.

As used herein the term "DMSO" is intended to mean dimethylsulfoxide.

As used herein the term "basement cells" is intended to mean the layer of cells from which the MCP cells arise. Basement cells are further defined by morphological characteristics as well as by specific marker characteristics.

As used herein, the term "MCP" is intended to mean multipotent cardiac progenitor, which is a cell type that can give rise to many different cell types within the mesodermal lineage. One such cell type it can give rise to is cardiomyocyte-like cells, being cells sharing features with mature cardiomyocytes. MCP cells are further defined by morphological characteristics as well as by specific marker characteristics, such as gene expression of Flk-1(KDR), ISL-1, Notch-1, Nkx2.5, GATA-4, and troponin T type 2 (TNNT2). Further, the MCP cells are defined as non-contracting cardiac precursors.

As used herein the terms "MCP cluster" and "MCP cell cluster" are intended to mean a group of at least two MCP cells attached to each other.

As used herein the terms, "down regulated" and "up regulated" are intended to mean at least a 2-fold distinction in regulation compared to undifferentiated cells.

Feeder Cells

As used herein feeder cells are intended to mean supporting cell types used alone or in combination. The cell type may further be of human or other species origin. The tissue from which the feeder cells may be derived include embryonic, fetal, neonatal, juvenile or adult tissue, and it further includes tissue derived from skin, including foreskin, umbilical chord, muscle, lung, epithelium, placenta, fallopian tube, glandula, stroma or breast. The feeder cells may be derived from cell types pertaining to the group consisting of human fibroblasts, fibrocytes, myocytes, keratinocytes, endothelial cells and epithelial cells. Examples of specific cell types that may be used for deriving feeder cells include embryonic fibroblasts, extraembryonic endoderm cells, extraembryonic mesoderm cells, fetal fibroblasts and/or fibrocytes, fetal muscle cells, fetal skin cells, fetal lung cells, fetal endothelial cells, fetal epithelial cells, umbilical chord mesenchymal cells, placental fibroblasts and/or fibrocytes, placental endothelial cells, post-natal foreskin fibroblasts and/or fibrocytes, post-natal muscle cells, post-natal skin cells, post-natal endothelial cells, adult skin fibroblasts and/or fibrocytes, adult muscle cells, adult fallopian tube endothelial cells, adult glandular endometrial cells, adult stromal endometrial cells, adult breast cancer parenchymal cells, adult endothelial cells, adult epithelial cells or adult keratinocytes. When feeder cells are derived from hBS cells, the cells may be fibroblasts.

As used herein, the term "MEF cells" is intended to mean mouse embryonic fibroblasts.

As used herein the term "germlayer" is intended to mean any of the three major lineages known from developmental biology, i.e. ectoderm (giving rise to e.g. neural tissue), mesoderm (giving rise to e.g. connective tissue, cartilage, and bone) and endoderm (giving rise to tissues of the internal organs, such as the gut epithelium, liver and pancreas).

As used herein, the term "hFF cells" is intended to mean human foreskin fibroblasts. The hFF cells can further be commercially available or derived as described in the Methods part herein.

As used herein, the term "FGF" means fibroblast growth factor, preferably of human and/or recombinant origin, and subtypes belonging thereto are e.g. bFGF (sometimes also referred to as FGF2) and FGF4.

As used herein, the term "EGF" is intended to mean epithelial growth factor.

The term "BMP2" is intended to mean bone-morphogenic protein-2 which is one member of the BMP family of growth factors.

As used herein the term "xeno-free" is intended to mean complete circumvention of direct or in-direct exposure to non-human animal components.

As used herein, the term "forced aggregation" is intended to mean increased attachment of cells either to each other or to a surface by the application of an external force.

Markers for undifferentiated hBS cells: SSEA-3, SSEA-4 (stage specific embryonic antigen 3 and 4), TRA-1-60, TRA-1-81, Oct-4, ALP (alkaline phosphatase).

Marker for early differentiated hBS cells: SSEA-1

Early markers from a developmental biology perspective for the mesoderm lineage or germlayer are vimentin, desmin, alpha-sarcomeric actin and marker for mesendodermal cells is Brachyury.

Marker for cells of ectoderm lineage: Nestin, GFAP (glial fibrillary acidic protein or GFAP is a type III protein of the intermediate filament exclusively found in astrocytic cells of the central nervous system).

Cardiac stem cell marker: c-kit and cardiac progenitor markers: Islet-1, Nkx2.5, GATA-4. Here regarded as early cardiac markers.

Markers for cardiomyocytes: cTnI, cTnT (cardiac troponin I and T), α-MHC (alpha-myosin-heavy-chain), connexin-43.

As mentioned in the above, the present invention provides MCP cells as well as the intermediate basement cells and differentiated MCP cells into cardiomyocyte-like cells. It is envisaged that the MCP cells as well as the basement cells are novel. Such cells are advantageously used for a multitude of investigative purposes such as, e.g., in drug discovery processes, in drug screening processes, in vitro models for studying drugs with potential effect on cardiac cell types, in vitro models for studying cardiogenesis such as early cardiogenesis, in vitro models for studying human cardiodegenerative disorders, in vitro cardiotoxicity testing, etc.

Furthermore, the MCP cells, the intermediate basement cells and the derived cardiomyocyte-like cells can advantageously be used for treatment and/or prevention of pathologies and/or diseases caused by tissue degeneration such as, e.g., degeneration of cardiac tissue. More specifically such disorders include cardiac disorders such as disorders related to necrotic, apoptotic, damaged, dysfunctional and/or morphologically abnormal myocardium. Other disorders include ischemic heart disease, cardiac infarction, rheumatic heart disease, endocarditis, autoimmune cardiac disease, valvular heart disease, congenital heart disorder, cardiac rhythm disordersm cardiac insufficiency and the like. Accordingly, the cells, notably the MCP cells and the cardiomyocyte-like cells according to the present invention can be used in medicine and in the preparation of a medicament.

MCP Cells

In the present context MCP cells are intended to mean cells with a very specific morphology and with specific marker characteristics. Accordingly, in a first aspect the invention relates to a cell population derived from human blastocyst-derived stem (hBS) cells comprising multipotent cardiac precursor (MCP) cells. The cell population population has the following characteristics
  i) at least 1% of the cells exhibit no antigen expression of one or more markers for undifferentiated cell, the marker being selected from the group consisting of SSEA-3, SSEA-4, TRA-1-60, TRA-1-81 and Oct-4,
  ii) at least 1% of the cells exhibit no protein expression of one or more of a neural marker including nestin or GFAP
  iii) at least 1% of the cells exhibit protein and/or gene expression of one or more of a mesodermal marker including brachyury, vimentin or desmin
  iv) at least 1% of the cells exhibit protein and/or gene expression of Flk-1 (KDR).

As it appears from the examples herein, Flk-1 is an excellent marker for MCP cells.

Moreover, for MCP cells at least 1% such as, e.g., at least 2%, at least 5%, at least 10%, at least 15%, at least 20%, at least 25%, at least 30%, at least 40%, at least 50%, at least 60%, at least 70%, at least 80%, at least 85%, at least 90% or at least 95% of the cells exhibit no protein expression of one or more early stage cardiac marker including islet-1, cTNI, cTNT, Nkx2.5, alpha-MHC or connexin 43.

In contrast to e.g. cardiomyocytes, MCP cells are non-contracting cells. Accordingly, a cell population according to the invention comprising MCP cells has at least 50% of such as, e.g., at least 60%, at least 70%, at least 80%, at least 85%, at least 90%, at least 95%, at least 99% or 100% cells, which are non-contracting cells.

As evidenced from the examples herein, Troponin T2 is a good marker for MCP cells. Accordingly, a cell population according to the present invention is a population, wherein at least 1% such as, e.g., at least 2%, at least 5%, at least 10%, at least 15%, at least 20%, at least 25%, at least 30%, at least 40%, at least 50%, at least 60%, at least 70%, at least 80%, at least 85%, at least 90% or at least 95% of the cells exhibit protein and/or gene expression of Troponin T2.

Also, CD31 has been shown as an excellent marker for MCP cells. Accordingly, a cell population according to the present invention is a population, wherein at least 1% such as, e.g., at least 2%, at least 5%, at least 10%, at least 15%, at least 20%, at least 25%, at least 30%, at least 40%, at least 50%, at least 60%, at least 70%, at least 80%, at least 85%, at least 90% or at least 95% of the cells exhibit protein and/or gene expression of CD31.

In specific situations, Nkx2.5 and GATA-4 are also fine markers for MCP cells. As shown in the examples, this is especially the case, when the MCP cells are obtained after culturing on mouse feeder cells. Accordingly, a cell population according to the present invention is a population, wherein at least 1% such as, e.g., at least 2%, at least 5%, at least 10%, at least 15%, at least 20%, at least 25%, at least 30%, at least 40%, at least 50%, at least 60%, at least 70%, at least 80%, at least 85%, at least 90% or at least 95% of the cells exhibit protein and/or gene expression of Nkx2.5 and/or GATA-4.

In a specific embodiment, the cell population according to the invention has at least 1% such as, e.g., at least 2%, at least 5%, at least 10%, at least 15%, at least 20%, at least 25%, at least 30%, at least 40%, at least 50%, at least 60%, at least 70%, at least 80%, at least 85%, at least 90% or at least 95% of the cells exhibit protein and/or gene expression of Flk-1 (KDR), Troponin T2, CD31, Nkx2.5 and GATA-4, i.e. cells that are MCP cells. In another specific embodiments, the cell population according to the present invention has at least 1% such as, e.g., at least 2%, at least 5%, at least 10%, at least 15%, at least 20%, at least 25%, at least 30%, at least 40%, at least 50%, at least 60%, at least 70%, at least 80%, at least 85%, at least 90% or at least 95% of the cells exhibit protein and/or gene expression of one or more markers of progenitor cells Flk-1 (KDR) and ISL-1, i.e. cells that are MCP cells.

In a further specific embodiments, the cell population according to the present invention has at least 2%, at least 5%, at least 10%, at least 15%, at least 20%, at least 25%, at least 30%, at least 40%, at least 50%, at least 60%, at least 70%, at least 80%, at least 85%, at least 90% or at least 95% of the cells exhibit protein and/or gene expression of two or more markers of progenitor cells Flk-1 (KDR), Notch-1 or ISL-1, i.e. cells that are MCP cells.

Characteristic i) ensures that the cells in general are differentiated cells, i.e. they are different from the hBS cells from which they are derived.

Characteristic ii) ensures that the cells in general have not differentiated into neural-like cells, characteristic iii) indicates that the cells have mesodermal character and characteristic iv) ensures that the hBS cells have developed into MCP cells.

Moreover, at least 1% of the cells exhibit no protein expression of one or more early stage cardiac marker such as, e.g., islet-1, cTNI, cTNT, Nkx2.5, alpha-MHC or connexin 43. This characteristic ensures that the cells have not yet differentiated into cardio-like cell, i.e. the cells are still precursor cells with potency for developing into different kinds of cells. As shown in the examples herein, MCP cells can develop into cardiomyocyte-like cells or other differentiated cell types, but they also have the ability of providing basement cells.

Figure 2:
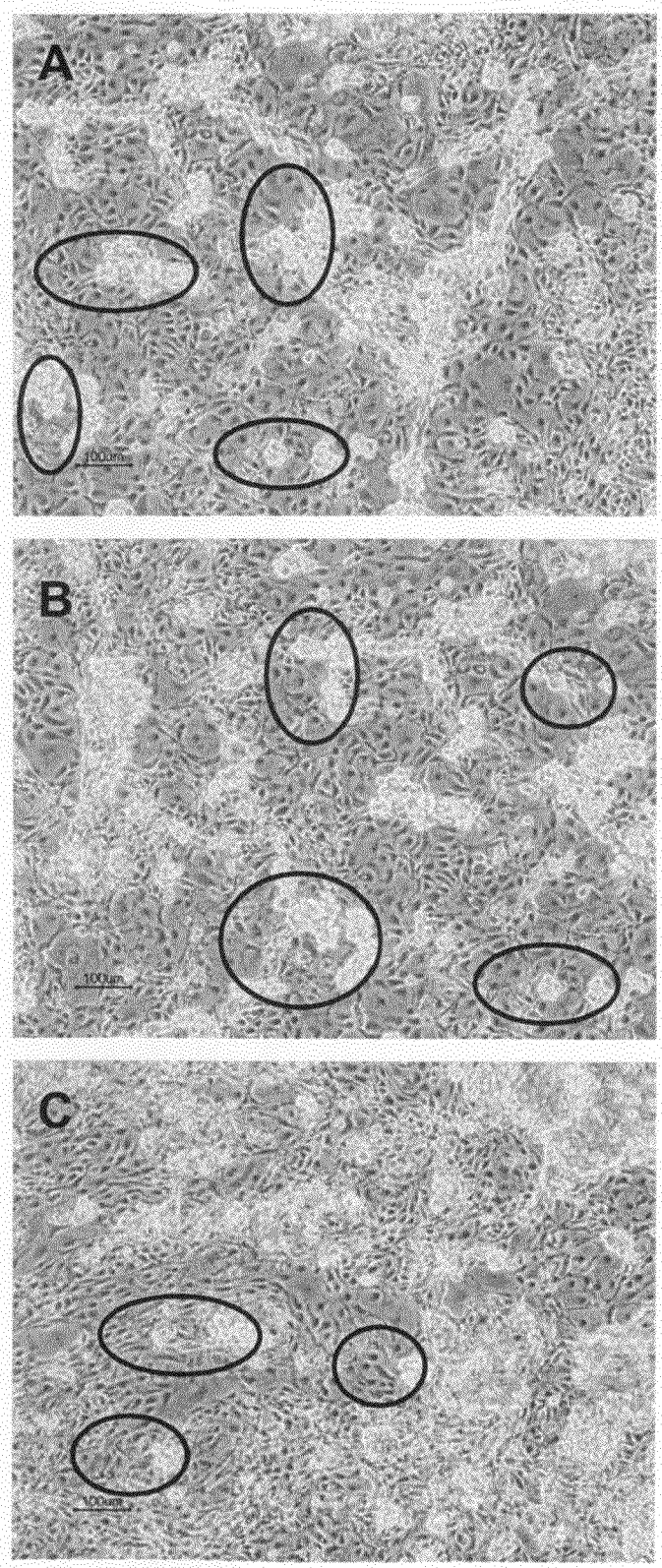

MCP cells have a very characteristic morphology as can be seen using light microscopy. Furthermore, MCP cells are shown in the figures herein. In one embodiment, the invention thus relates to a cell population comprising MCP cells that appear as clusters of small, round and phase-bright cells; individual cells are 5-20 μm in diameter and each cluster is composed of 2-500 cells. The clusters of MCP cells are either round or elongated in shape, as illustrated in FIG. 2 panel a, b and c.

Normally, the clusters of MCP cells appear as loosely adherent cell clumps that, if grown on basement cells, overlay a monolayer of basement cells. Moreover, the MCP cells have a relatively high nucleus-to-cytoplasma ratio, e.g. 1:2-1:64 of the total volume of the cell. A further characteristic morphological feature is seen from FIG. 2, namely the MCP clusters appear as balloons on a string as shown on a schematic sketch in FIG. 18.

Accordingly, in a specific embodiment a cell population according to the invention is a population, wherein at least 50% of the MCP cells that
  1. grow as clusters of small, round and phase-bright cells,
  2. form clusters of round or elongated shape, that appear as loosely adherent cell clumps that, if grown on basement cells, overlay a monolayer of basement cells,
  3. have a relatively high nucleus-to-cytoplasma ratio, and/or
  4. appear as balloons on a string
have all of the following characteristics
  i) at least 1% of the cells exhibit no antigen expression of one or more markers for undifferentiated cell, the marker being selected from the group consisting of SSEA-3, SSEA-4, TRA-1-60, TRA-1-81 and Oct-4,
  ii) at least 1% of the cells exhibit no protein expression of one or more of a neural marker such as, e.g., nestin or GFAP
  iii) at least 1% of the cells exhibit protein and/or gene expression of one or more of a mesodermal marker such as, e.g., brachyury, vimentin or desmin, and
  iv) at least 1% of the cells exhibit protein and/or gene expression of Flk-1 (KDR).

In a specific embodiment, at least 1% of the cells exhibit no protein expression of one or more early stage cardiac marker such as, e.g., islet-1, cTNI, cTNT, Nkx2.5, alpha-MHC or connexin 43 (characterstic v)).

Preferably, at least 50% of the MCP cells have at least two of the four characteristics such as at least three of the four characteristics or all four characteristics. In one embodiment of the invention, at least 55% such as, e.g., at least 60%, at least 65%, at least 70%, at least 75%, at least 80%, at least 85%, at least 90% or at least 95% of the MCP cells fulfil the requirements with respect to characteristics i), ii), iii) and/or iv).

As mentioned above, the present invention also relates to a cell population comprising MCP cells. Such a cell population fulfils at least characteristic i) such as, e.g., at least characteristic i) for at least two such as at least three, at least four or all of the markers mentioned in i). This feature is important since it is highly desirable to be able to distinguish the MCP cells from undifferentiated hBS cells.

In one embodiment of the invention, at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells in the cell population comprising MCP cells exhibit no antigen expression of one or more markers for undifferentiated cell, the marker being selected from the group consisting of SSEA-3, SSEA-4, TRA-1-60, TRA-1-81 and Oct-4.

Moreover or alternatively, the cell population has at least characteristic ii) for both markers mentioned in ii). This characteristic is important to ensure that differentiation into neural types of cells is avoided. In one embodiment of the invention, at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells in the cell population comprising MCP cells exhibit no protein expression of one or more of a neural marker such as, e.g., nestin or GFAP.

Characteristic iii) relates to presence of mesodermal characteristics and preferably at least characteristic iii) for two or three of the markers mentioned in iii) are fulfilled. . In one embodiment of the invention, at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells in the cell population comprising MCP cells exhibit protein and/or gene expression of one or more of a mesodermal marker such as, e.g., brachyury, vimentin or desmin.

Characteristic v) is of importance to ensure that the cells not yet have developed into early stage cardio-like cells and, accordingly, the cell population has preferably at least characteristic iv) for at least 2 such as, e.g., 2, 3, 4, 5 or 6 of the markers mentioned in iv). In one embodiment of the invention, at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells in the cell population comprising MCP cells exhibit no protein and/or gene expression of one or more early stage cardiac marker such as, e.g., islet-1, cTNI, cTNT, Nkx2.5, alpha-MHC or connexin 43.

In specific the cell population has at least two of the four characteristics such as at least three of the four characteristics or all four characteristics.

The cell population according to the invention can be xeno-free, which is an advantage if used for medical purposes.

The MCP cells according to the invention are capable of maintaining those of the characteristics i)-v) they exhibit during cultivation. In this context the term "maintained characteristics" is intended to mean stable protein, gene or antigene expression over a defined culture and analysis period, which can be further shown e.g. with immuno histochemistry and measuring and comparing expression intensities. Accordingly, a cell population comprising MCP cells according to the present invention may be cultured in vitro.

Furthermore, MCP cells can be re-generated and subsequently isolated from the same layer of basement cells. Such re-generation can be performed up to 20 times. Basement cells and MCP cells both show precursor properties such as Flk-1 (KDR) gene expression and studies through time-laps (example 14) has shown that the MCP cells can give rise to basement cells as well as basement cells giving rise to MCP cells, i.e the cells are to be closely linked precursor cells with some properties in common.

Differentiated MCP Cells

One very important property of the novel MCP cells is their ability of differentiating into cardiomyocyte-like cells. Accordingly, in one embodiment of the invention, a cell population according to the invention is subjected to differentiation by plating and using a differentiation medium for a time period of at least 5 days and then it has at least one of the following characteristics i) at least 1% of the cells exhibit protein and/or gene expression of one ore more mesodermal markers such as, e.g., brachyury, vimentin or desmin, ii) at least 1% of the cells exhibit protein and/or gene expression of one ore more cardiac markers such as, e.g., islet-1, GATA-4, Nkx2.5, cTNI, cTNT or connexin 43, iii) at least 1% of the cells exhibit no antigen expression of one or more markers for undifferentiated stem cells, the marker being selected from the group consisting of SSEA-3, SSEA-4, TRA-1-60, TRA-1-81 and Oct-4.

Comparing with the characteristic of the MCP cells it is seen that these cardiomyocyte-like cells derived from the MCP cells maintain their characteristic with respect to mesodermal markers. In a specific embodiment these cells fulfil at least characteristic i) such as at least characteristic i) for two or three of the markers mentioned in i). In a specific embodiment characteristic i) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

Moreover, the cardiomyocyte-like cells derived from MCP cells should have characteristic ii) in order to confirm their cardiomyocyte-like character, i.e. they have positive cardiac markers, i.e. the differentiation into cardiac-like cells are confirmed. In a specific embodiment these cells fulfil at least characteristic ii) for at least 2 such as, e.g., 2, 3, 4, 5 or 6 of the markers mentioned in ii). In a specific embodiment characteristic ii) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

The differentiated cells also retain their characteristics with respect to differentiation, i.e. the cell population after subjection to differentiation has at least characteristic iii) for at least 2 such as, e.g., 2, 3, 4 or 5 of the markers mentioned in iii). In a specific embodiment characteristic iii) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

Preferably, the cell population after subjection to differentiation has at least two or all three characteristics.

Basement Cells

The basement cells are important intermediary cells in the formation of MCP cells. They are distinct from the hBS cells from which they are derived and they are also morphologically distinct from the MCP cells. Accordingly, the present invention also relates to a cell population derived from human blastocyst-derived stem (hBS) cells, the cell population comprising basement cells. The cell population has the following characteristics i) at least 1% of the cells exhibit protein and/or gene expression of brachyury
ii) at least 1% of the cells exhibit protein and/or gene expression of alpha-sarcomeric actin,
iii) at least 1% of the cells exhibit no protein expression of vimentin,
iv) at least 1% of the cells exhibit no protein expression of desmin, and
v) at least 1% of the cells exhibit no antigen expression of one or more markers for undifferentiated cell, the marker being selected from the group consisting of SSEA-3, SSEA-4, TRA-1-60, TRA-1-81 and Oct-4.

As seen from the examples herein, basement cells exhibit gene and/or protein expression of a number of genes, such as those listed in table 11, example 3. Accordingly, a cell population according to the invention comprising basement cells has the following further characteristics i) at least 1% of the cells exhibit gene expression of at least one or more of the genes listed in table II, example 3, such as Basonuclin 1 (BNC1), nephronectin (NPNT), fibrinogen alpha chain (FGA), annexin A8 (ANXA8), matrix Gla protein (MGP), zona pellucida glycoprotein 4 (ZP4), thrombomodulin (THBD), homeobox B7 (HOXB7), heart and neural crest derivatives expressed 1 (HAND1), desmocollin 3 (DSC3), interleukin 6 signal transducer (IL6ST), aquaporin 1 (AQP1), Frizzled-related protein (FRZB), bradykinin receptor B1 (BDKRB1), growth hormone receptor (GHR) and kinase insert domain receptor (Flk-1) (KDR).
ii) at least 1% of the cells has down regulated gene expression of oct-4 and nanog compared to undifferentiated hBS cells The characteristic listed above for basement cells are normally valid for at least 5% such as, e.g., at least 10%, at least 15%, at least 20%, at least 25%, at least 30%, at least 40% or at least 50% of the cells in the cell population.

Figure 19:
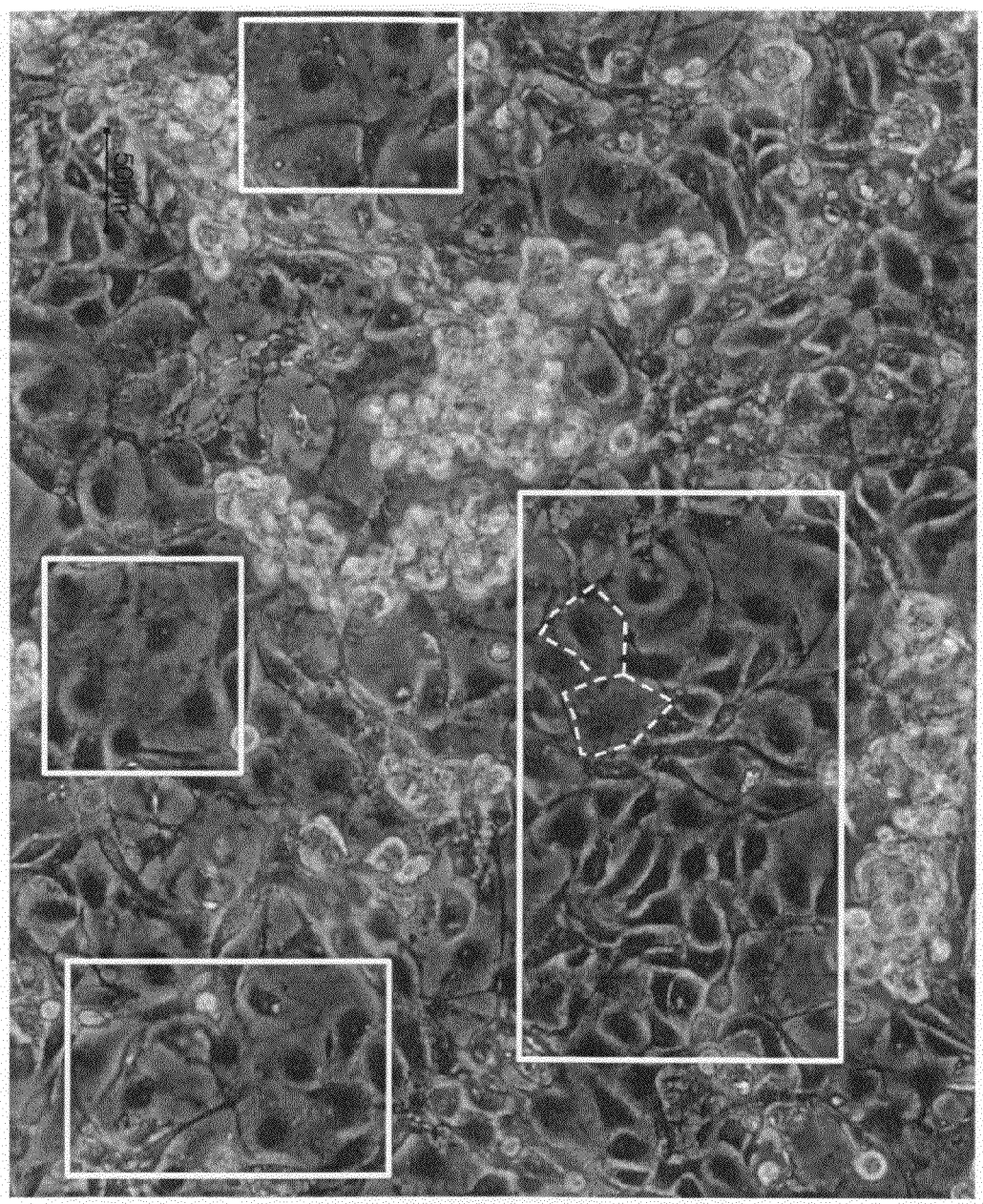

Basement cells have a very characteristic morphology as can be seen using light microscope. Furthermore, basement cells are shown in the figures herein. In one embodiment, the invention thus relates to a cell population comprising basement cells that have morphology with similarities to primitive endoderm and the cells are epithelial-like, i.e. they have an endothelial cell-like shape. The basement cells are also phase-dark and well demarcated (i.e. evident borders between adjacent cells) and/or they may have an angular shape as evidenced by light microscopy (FIG. 19).

In a specific embodiment the invention relates to a cell population comprising basement cells, wherein at least 5% of the basement cells that 1. have a morphology with similarities to primitive endoderm,
2. are epithelial like,
3. are phase-dark and well demarcated as evidenced by light microscopy, and/or
4. have an angular shape as evidenced by light microscopy have at least one of the following characteristics i) at least 1% of the cells exhibit protein and/or gene expression of brachury
ii) at least 1% of the cells exhibit protein and/or gene expression of alpha-sarcomeric actin,
iii) at least 1% of the cells exhibit no protein expression of vimentin, and
iv) at least 1% of the cells exhibit no protein expression of desmin
v) at least 1% of the cells exhibit no antigen expression of one or more markers for undifferentiated cell, the marker being selected from the group consisting of SSEA-3, SSEA-4, TRA-1-60, TRA-1-81 and Oct-4

In specific embodiments, at least 5% of the basement cells have at least two of the five characteristics and preferably the two characteristics are i) and iv) or they have at least three, four or all five characteristics. Normally, the characteristics are valid for at least 10% such as, e.g., at least 20%, at least 30%, at least 40%, at least 50%, at least 60%, at least 70%, at least 80%, at least 85%, at least 90% or at least 95% of the cells.

In a specific embodiment the invention GATA-1 is an important transcription factor. The role of GATA-1 is specifically notable since GATA-1 has been reported to be involved in hematopoiesis (blood formation) (Huber and Zon 1998, 10(2):103-109, Semin Immunol). Here we propose that GATA-1 can also provide a biological link between cardiogenesis and hematopoiesis by regulating early cellular processes occurring during development. The hemangioblasts, that give rise to vascular cells and blood cells, share developmental pathways with cardiac progenitors and also originates from the mesoderm in the early embryo.

As mentioned above, the present invention also relates to a cell population comprising basement cells. Such a cell population fulfils at least characteristic i), at least two of the five characteristics, the two characteristics preferably being are i) and iv), at least three of the five characteristics, at least four of the five characteristics or the cell population has all five characteristics. In general, each of the characteristics i)-v) is valid for at least 5% such as, e.g., at least 10%, at least 15%, at least 20%, at least 25%, at least 30%, at least 40% or at least 50% of the cells.

The basement cells may also be obtained in xeno-free form.

The use of the individual type of cell of cell population is described herein before or appears from the examples or the appended claims.

In a specific embodiment the invention relates to a cell population comprising basement cells and MCP cells, wherein at least 5% of the whole cell population (i.e. basement cells and MCP cells) exhibits gene and/or protein expression of Flk-1.

Method for Preparation

Starting Material

The starting material for the present invention is suitably pluripotent undifferentiated hBS cells, such as undifferentiated hBS cell lines. Such material can be obtained from Cellartis AB and is also available through the NIH stem cell registry. Cellartis AB has two hBS cell lines (SA001 and SA002) and one subclone of SA002 (SA002.5) available through the NIH. Those hBS cell lines have been frequently used in the present invention.

The Cellartis™ hBS cell lines SA001, SA002, SA046, SA094, SA111, SA121, SA181, SA191, SA196, SA202, SA218, SA240, SA348, SA352, SA399, SA461, SA502, SA506, SA521 and SA540 are also approved for the UK Stem Cell Bank registry at the MRC (Medical Research Council).

Characteristics of the hBS cells recommended as starting material are the following: positive for alkaline phosphatase, SSEA-3-SSEA-4, TRA 1-60, TRA 1-81, Oct-4, negative for SSEA-1, telomerase activity, and pluripotency in vitro and in vivo (the latter shown by teratomas formation in immunodeficient mice).

Before use, the hBS cell lines used as starting material may be derived from a LOT preparation subjected to a characterization program. The LOT preparation of hBS cell lines constitutes an expansion of the hBS cells in culture and a subsequent freezing of more than 100 straws in one single passage according to a standardized method (patent pending, WO2004098285), see the experimental section herein.

The starting material used herein may furthermore be completely xeno-free derived whereby completely xeno-free basement, MCP or cardiomyocyte-like cells may be obtained for potential use in regenerative medicine. For xeno-free derivation of hBS cells all medium and matrix components, feeder cells and other material used may not be derived from or been in contact with any non-human animal material. Suitable components for xeno-free derivation of hBS cells and furthermore xeno-free basement, MCP or cardiomyocyte-like cells are xeno-free derived human fibroblasts, such as human foreskin fibroblasts, serum-free or human serum based culture medium with recombinant growth factors, differentiation factors and/or potential other additives, and either human recombinant enzymes or sterile mechanical tools for dissociation and propagation of the cells.

3D Culture

I. Suspension Culture

The basement cells as well as the MCP cells are derived from undifferentiated hBS cells. A cell population comprising basement cells are obtained by a method comprising the steps of
i) culturing of one or more pieces of colonies or colonies of undifferentiated hBS cell in a differentiation medium in a suspension culture of from about 1 to about 10 days such as from about 1 to about 6 days,
ii) transferring the thus cultured cells to a culture vessel for continued proliferation and differentiation,
iii) optionally, identifying basement cells by morphological criteria in light microscope and/or relevant marker identification as defined herein,
iv) optionally, isolating the thus obtained basement cells, and
v) optionally, repeating steps ii)-iv)

Undifferentiated hBs cells were maintained and propagated in 3-6 days, such 4-5 days. The undifferentiated cells were dissected (e.g. manually) and placed in a differentiation medium, such as defined below as suspension cultures. The cells were maintained in suspension for 1-10 days, e.g., 1-8 days or 1-6 days, and transferred to e.g. gelatin coated dishes, leading to adhesion of cell clusters. Proliferation and differentiation are continued for about 2-6 days, e.g., 4 days. A monolayer of cells appears from clusters of cells and basement cells can be identified by use of e.g. light microscopy (as discussed herein).

II. Forced Aggregation

The basement cells as well as the MCP cells are derived from undifferentiated hBS cells. A cell population comprising basement cells are obtained by a method comprising the steps of
i) Detachment and dissociation of the hBS cells in to a suspension and distribution of cell suspension to a multi-well tissue culture plate,
ii) application of a centrifugal force for forced aggregation of the cells,
iii) culture of thus enhanced 3D-clustered cells in a differentiation medium in a micro well format from about 1 to about 20 days such as from about 6 to about 8 days,
iv) optionally, transferring the thus 3D-cultured cells to a culture vessel for continued proliferation and differentiation,
v) optionally, identifying basement cells by morphological criteria in light microscope and/or relevant marker identification as defined herein,
vi) optionally, isolating the thus obtained basement cells, and
vii) optionally, repeating steps iii)-iv)

Step i) normally starts with suspending pieces of undifferentiated hBS cell colonies in a differentiation medium with or without serum. Suitable differentiation media (e.g. for step i) in the suspension culture and step iii) in the forced aggregation method) includes but are not limited to the differentiation medium as described in Example 1 comprising KO-DMEM supplemented with Glutamax (e.g. in a concentration from 0.1 to 2 mM such as 1 mM), β-MeOH (e.g. in a concentration from 0.01 to about 1 mM such as, e.g., 0.1 mM), one or more non-essential amino acids (NEAA) (e.g. in a concentration from 0.1% to about 2% such as, e.g., 1%), PeST (e.g. in a concentration from about 0.1 to about 2% such as, e.g., about 1%) and/or a serum such as, e.g., fetal bovine serum (e.g. in a concentration of from 5 to 30% such as, e.g., about 20%) or the CGM medium as described in Example 6 (base medium composed of 35% IMDM and 65% DMEM: F12, supplemented with 1% PeST and Glutamax and made to a final concentration of 3,5% FBS, 2% B-27, 0.1 mM β-MeOH, 10 ng/ml EGF, 20 ng/ml bFGF, 4 nM Cardiotrophin-1, and 40 nM Thrombin) or combinations or variations thereof.

In those cases, where serum is included, the serum may be FBS or human serum. If present, the concentration of serum is at least 2% such as, e.g., from about 2% to about 30%, from about 5% to about 25% or about 20%.

In the forced aggregation method step i) (i.e. the detachment) is initiated by enzymatic treatment of the cells, e.g., by treatment with a collagenase such as collagenase IV. The concentration of the enzyme is normally in a range corresponding to 50-500 U/mL). The detached cells are then transferred to a culture medium (such as the medium described above) and dissociated mechanically. In step ii) the centrifugation is carried out from 100 to 1000×g notably about 400×g and normally for a suitable time period (e.g. 400×g in 5 min or equivalents thereof). After centrifugation the cells are incubated for a time period of 5-10 days, notably 6-8 days. 3D cluster structures are transferred e.g. to gelatin coated dishes containing culture medium and cultured for 2-6 days, notably 4 days. Medium is normally changed every 1-3 days such as every second to third day.

Basement cells can then be identified morphologically as well as by use of specific markers as described herein.

Derivation of Basement Cells

In order to enable formation of basement cells the present inventors have found that it is important that step i) of the suspension method is carried out for a relatively short period of time. Thus, in a specific embodiment step i) is performed for a time period of from about 1 to abut 6 days such as, e.g., from about 1 to about 4 days, from about 1 to about 3 days or from about 1 to about 2 days.

In step ii) of the suspension method the cells from the suspension culture are plated in a culture vessel or on an extracellular matrix. Any suitable vessel can be employed such as, e.g., multi well formats, culture dishes, flasks etc. Preferably, the cells adhere to the surface of the vessel and a medium is used so that the cells continue to proliferate and differentiate. The adherence of the cells may be directly on plastic, such as tissue culture plastic, protein coating such as laminin, poly-ornitin, on extracellular matrix components such as Matrigel, or on feeders or, preferably, gelatin-coated vessels.

The medium employed in step ii) may be with or without serum. If serum is present, the same concentrations as mentioned above are suitable for use in step ii) as well. The medium may be switched or same type of medium used in step ii). Suitable media include differentiation medium as described in Example 1 and CGM medium. Suitable additives to the media used are growth factors such as EGF and bFGF and a serine protease such as Thrombin. The medium may further comprise IMDM and DMEM: F12, optionally supplemented with 1% PeST and Glutamax and made to a final concentration of 3.5% FBS, 2% B-27, 0.1 mM β-MeOH, 10 ng/ml EGF, 20 ng/ml bFGF, 4 nM Cardiotrophin-1, and 40 nM Thrombin, as described in Example 4) for enrichment of MCP cells.

Normally, step ii) is performed for a time period of from about 2 to about 20 days such as e.g. from about 2 to abut 15 days, from about 2 to about 10 days, from about 2 to about 6 days or from about 2 to about 4 days.

Then basement cells appear and can be identified as described herein before. The basement cells may be isolated e.g. by mechanical dissection using a sharp micro capillary or another suitable tool or by enzymatic digestion using e.g. a collagenase, trypsin, using a chelator, such as EDTA. The basement cells may be re-plated and steps ii)-iv) repeated.

The basement cells or cell population comprising the basement cells can be stored e.g. by freezing or cryopreservation e.g. as described in the examples herein and can be used for purposes described herein.

Derivation of MCP Cells

Isolated or non-isolated basement cells can be used for the preparation of MCP cells. Accordingly, the invention also relates to a method for the preparation of a cell population comprising MCP cells, the method comprising steps for obtaining basement cells, e.g. steps i)-iii) as defined above or, alternatively, comprising the use of isolated or non-isolated basement cells and the further steps of vi) culturing the basement cells until MCP cells appears as evidenced by light microscope and/or relevant marker identification as defined herein, vii) isolating the thus obtained MCP cells.

Suitable media for the culturing of the basement cells in order to achieve MCP cells are e.g. differentiation medium or CGM medium or combinations thereof. The medium may contain serum (see above) or it may serum-free. The medium may be switch or it may be the same medium.

After a time period of from about 2 to abut 25 days after plating such as, e.g., from about 2 to about 20 days, from about 2 to about 15 days, from about 2 to abut 10 days, from about 2 to about 5 days or from about 2 to about 4 days after plating clusters of MCP cells appear. These clusters can be isolated e.g. by mechanical dissection using a sharp micro capillary or another suitable tool or by enzymatic digestion using e.g. a collagenase, trypsin, using a chelator, such as EDTA.

MCP clusters can furthermore be isolated in sequential rounds, such as from 1 to 20 times, from 5 to 10 times between day 1 and day 20, such as between day 5 and day 10 after that the basement cells have appeared.

The MCP cells may further be sub-cultured e.g. for storage, for use for cardiac differentiation, for characterization, for use in drug discovery, for use in toxicity testing, for use in regenerative medicine and/or for obtaining basement cells.

Differentiation of MCP Cells

Furthermore, the MCP cells may be subjected to differentiation to provide cardiomyocyte-like cells by i) plating MCP cells on a surface in the presence of one or more differentiation factors such as growth factors of the BMP and FGF families, B-27, 5-aza deoxycytidine, DMSO, retinoic acid, ASA and ascorbic acid and/or medium to obtain differentiated MCP cells.

Other Aspects

The invention also relates to a kit. Details and particulars of the aspects described above apply mutatis mutandis to the kit aspect. Specific embodiments appear from the appended claims. Thus, a kit of the invention may comprise a cell population comprising basement cells, MCP cells or cardiomyocyte-like cells derived from MCP cells, ii) one or more maturation factors and/or a maturation culture medium driving the cardiac differentiation, and iii) optionally, an instruction for use. The maturation culture medium may be selected from the group consisting of VitroHES™, VitroHES™ supplemented with bFGF, autologuous pre-conditioned VitroHES™, CGM medium, and other cardiac specific culture media, and the one or more maturation factors are selected from the group consisting of FGF, such as bFGF, BMP, 5-aza deoxycytidine, DMSO, retinoic acid, ascorbic acid, and ASA. The kit may further comprise tools for monitoring maturation. Suitable tools may comprise i) PCR primers against at least three, such as, e.g. at least four or at least five of the genes coding for expression markers selected from the group consisting of markers for undifferetnatiated hBS cells, desmin, alpha-sarcomeric actin, Brachyury, Nestin, GFAP, Islet-1, Nkx2.5, GATA-4, cTnI, cTnT, α-MHC, and connexin-43, or i) antibodies against at least three, such as, e.g. at least four or at least five of the expression marker antigens selected from the group consisting of markers for undifferetnatiated hBS cells, desmin, alpha-sarcomeric actin, Brachyury, Nestin, GFAP, Islet-1, Nkx2.5, GATA-4, cTnI, cTnT, α-MHC, and connexin-43.

In another embodiment a kit of the invention comprises i) basement and/or MCP cells ii) optionally, factors for driving differentiation in vitro and or in vivo iii) tools for administration of the cells to a patient or cells as such in an administrative form, such as in a ready-to-use syringe.

The invention is further illustrated in the following non-limiting examples and figures. Specific embodiments appear from the items and claims herein.

FIGURES

FIG. 1. Morphology of basement cells.

A. Shows a monolayer of differentiating cells 3 days after plating, arisen from adherent clusters of differentiating hBS cells. The basement cells grow in a characteristic tight network resembling a maze which makes areas of basement cells easy to distinguish using light microscopy in a culture of differentiating hBS cells. The morphology of the basement cells share similarities with primitive endoderm and the cells are epithelial-like. In addition, individual cells are phase-dark, well demarcated, and usually angular in shape. The figure illustrates cell obtained from hBS cell line SA002.5, LOTBE002.5, passage 26, maintained on MEF cells. Typical areas of basement cells are indicated.

B. Shows a monolayer of differentiating cells 8 days after plating, arisen from adherent clusters of differentiating hBS cells. The monolayer contains basement cells (a typical area is indicated). The figure illustrates cell obtained from hBS cell line SA002.5, LOTBE002.5, passage 42+enzymatic dissociation 4 maintained on hFF cells.

C and D. Show a monolayer of differentiating cells 15 days after plating, arisen from adherent clusters of differentiating hBS cells over which clusters of MCP cells appear. In panel C a typical area is indicated within the square. In panel D the square marks an area with basement cells and the dashed oval marks a typical cluster of MCP cells overlaying the basement cells. The figures illustrate cells obtained from hBS cell line SA002.5, LOTBE002.5, passage 26, maintained on MEF cells.

FIG. 2. Morphology of MCP cell clusters overlaying basement cells.

Panels A-C show MCP cells, 15 days after plating of differentiated hBS cells, growing as clusters of small, round, and phase-bright cells loosely adherent to the monolayer of basement cells. They have a high nucleus-to-cytoplasm ratio. A typical feature of the clusters is the similarity to "balloons on a sting". The MCP cell clusters can either be round or elongated in shape. The ovals indicate typical MCP cell clusters. The figures illustrate cells obtained from hBS cell line SA002.5, LOTBE002.5, passage 26, maintained on MEF cells. Panel A includes a schematic sketch of a MCP cluster with the "balloons on a string" morphology.

Figure 3:
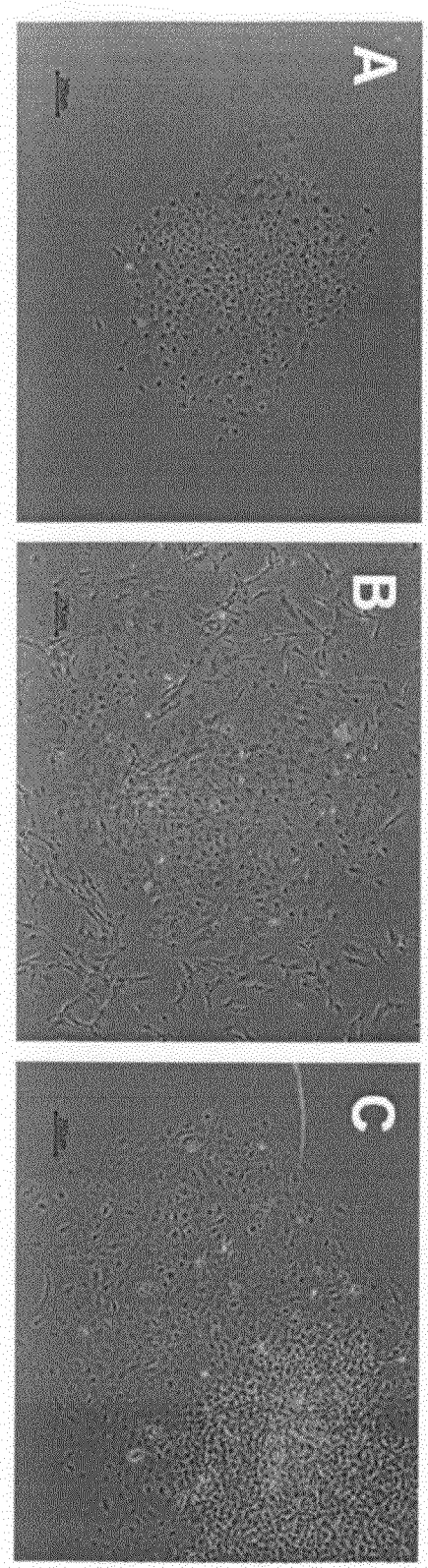

FIG. 3 Morphology of isolated and re-plated non-beating MCP cells

A. Shows the morphology of an isolated MCP cell cluster, 6 days after isolation, transferred to a new culture dish in (serum containing) differentiation medium. The figure illustrates cells obtained from hBS cell line SA461, LOTBF461, passage 22 maintained on MEF cells.

B. Shows the morphology of an isolated MCP cell cluster, 7 days after isolation, transferred to a new culture dish in differentiation medium. The figure illustrates cells obtained from hBS cell line SA121, LOTBD121, passage 156+enzymatic dissociation 10 maintained on HFF cells.

C. Shows the morphology of an isolated MCP cell cluster, 12 days after isolation, transferred to a new culture dish in differentiation medium. The figure illustrates cells obtained from hBS cell line SA121, LOTBD1 21, passage 156+enzymatic dissociation 10 maintained on HFF cells.

Figure 4:
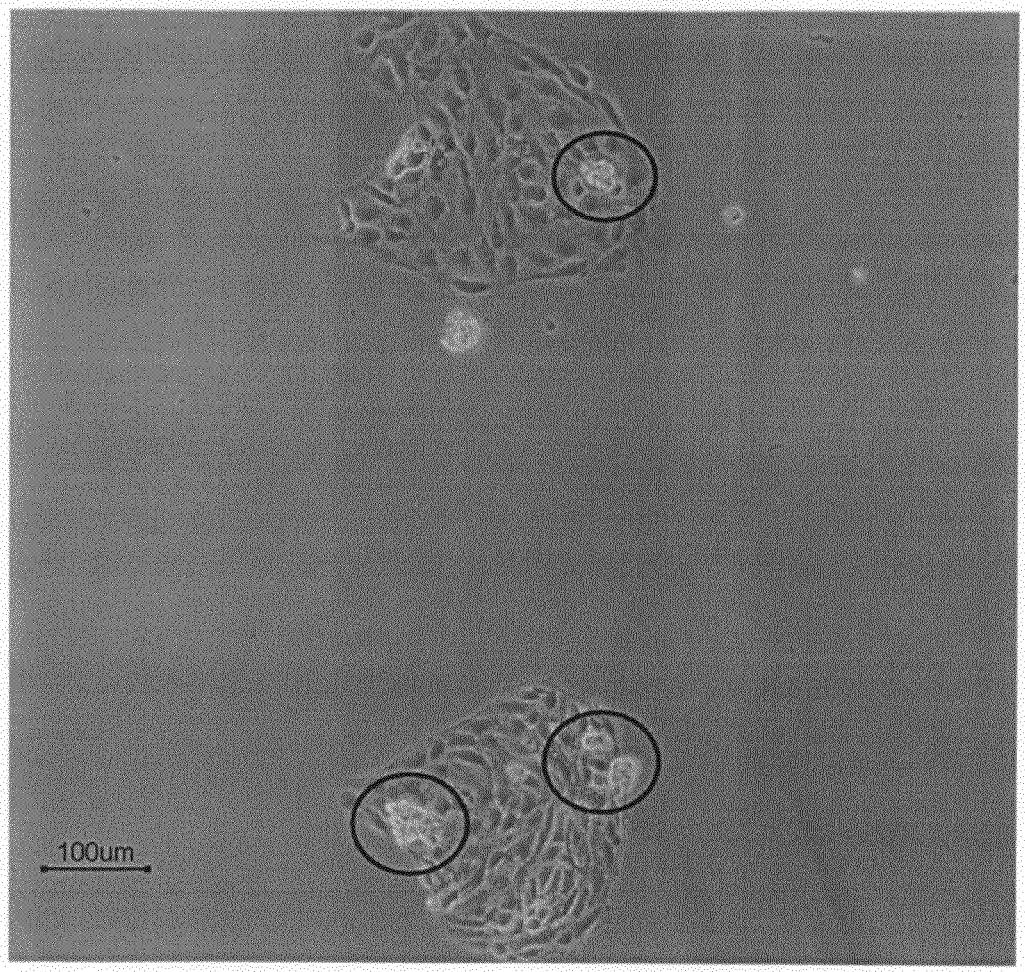

FIG. 4 Morphology of isolated and re-plated MCP cells which give rise to new basement cells and new MCP clusters.

The figure shows isolated MCP cells which differentiate to new basement cells, 1 day after isolation in differentiation medium without FBS. New MCP cells can be observed overlaying the basement cells (indicated by the ovals). The figure illustrates cells obtained from hBS cell line SA002, LOTAL002, passage 55+enzymatic dissociation 3 maintained on hFF cells and SA002.5, LOTBE002.5, passage 26 on MEF cells.

Figure 5:
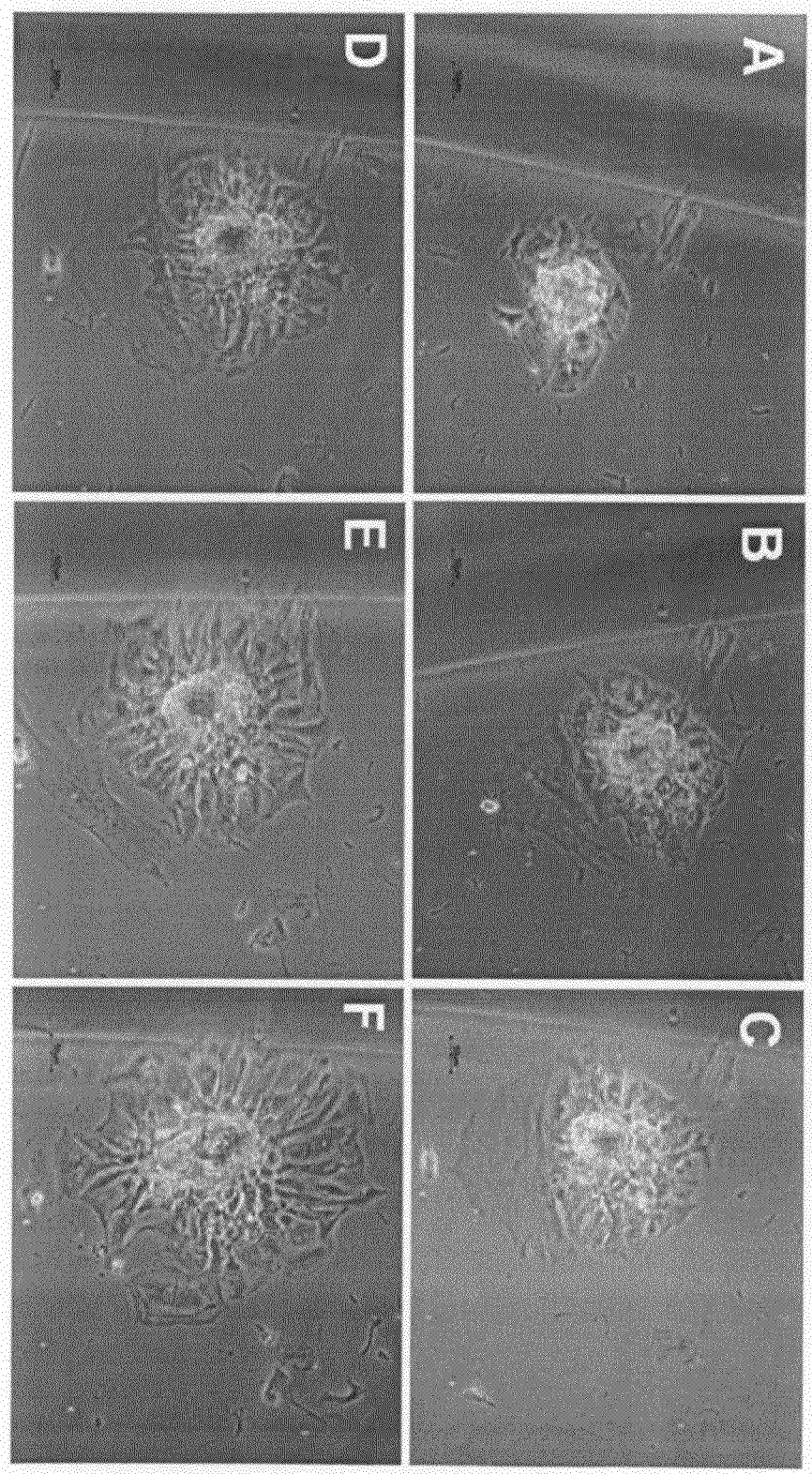

FIG. 5 Morphology of spontaneously contracting cells derived from MCP cells The FIGS. 5A-5F illustrate cells obtained from hBS cell line SA002, LOTAL002, passage 34, maintained on MEF cells.

A. Shows the morphology of a proliferating and spontaneously contracting MCP cell cluster 8 days after isolation in differentiation medium.

B. Shows the same cell cluster 11 days after isolation.
C. 13 days after isolation.
D. 15 days after isolation.
E. 18 days after isolation.
F. 26 days after isolation.

Figure 6:
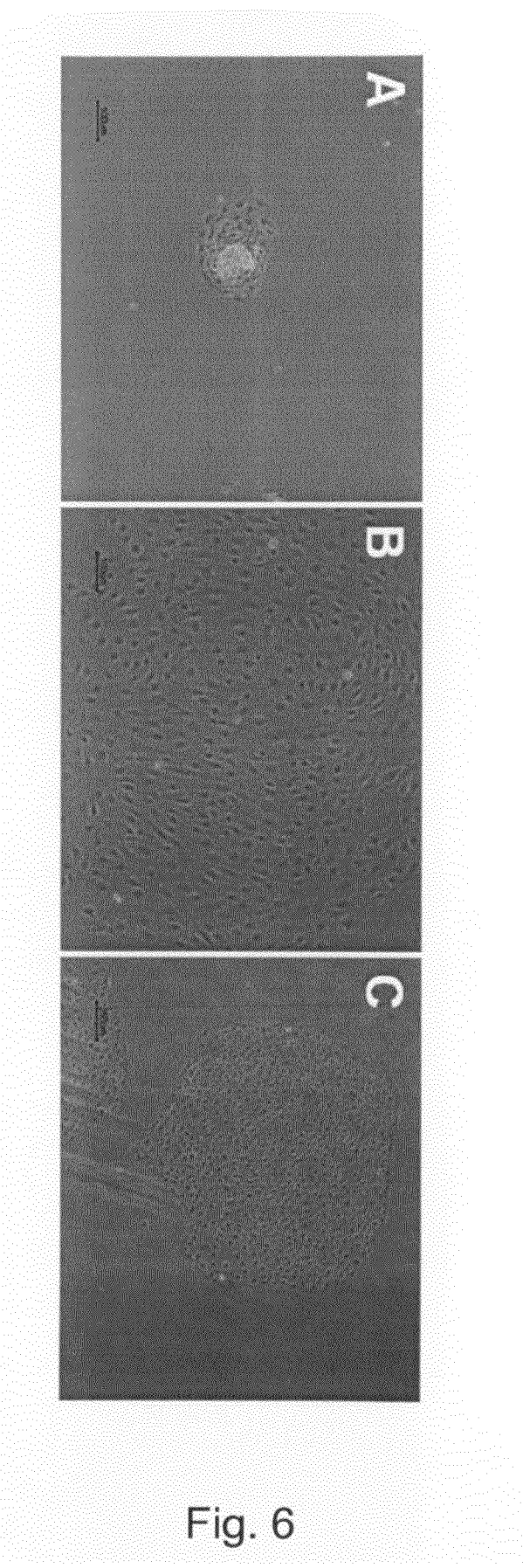

FIG. 6 Differentiation of MCP cells in the absence of serum

The FIGS. 6A-6C illustrate cells obtained from hBS cell line AL002, passage 55+enzymatic dissociation 3 maintained on hFF cells and SA002.5, LOTBE002.5, passage 26 on MEF cells.

A. Shows a typical morphology of isolated MCP cells in medium without serum, 1 day after isolation.

B. Shows a typical homogenous morphology of isolated MCP cells in medium without serum, 7 days after isolation.

C. Shows a typical homogenous morphology of isolated MCP cells in medium without serum, 9 days after isolation.

Figure 7:
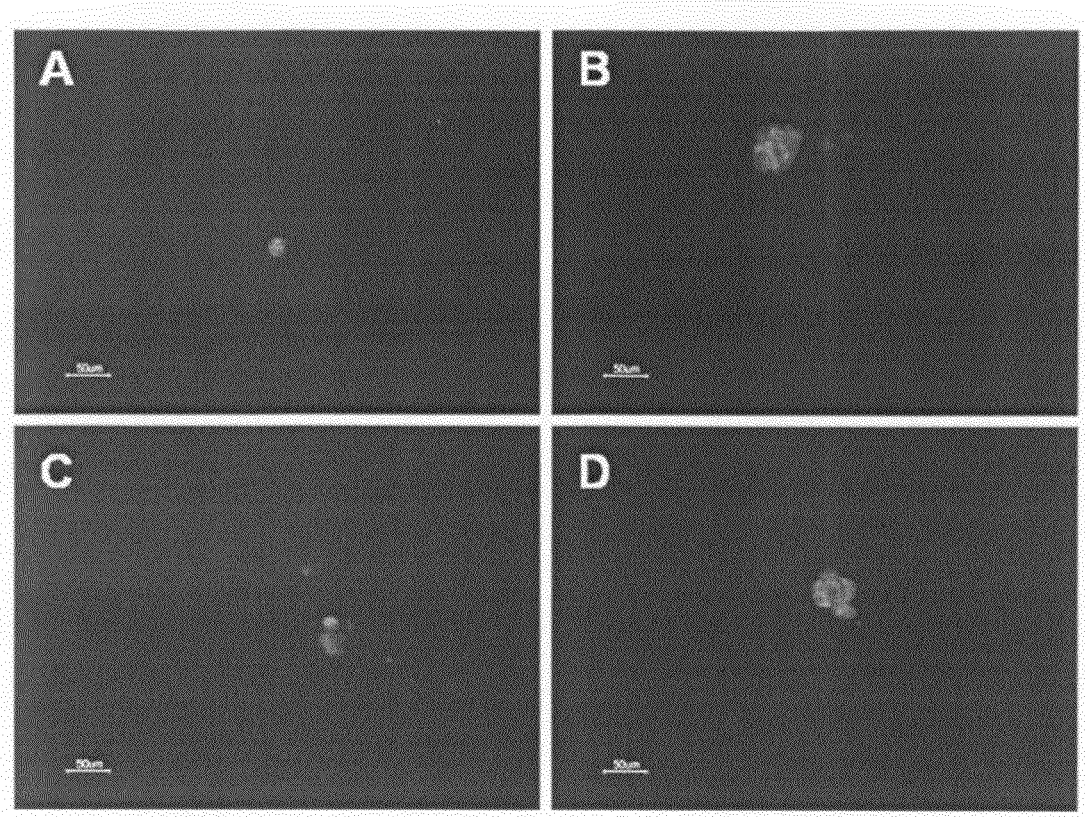

FIG. 7 Vimentin staining of MCP cells directly when isolated using Cytospin

Vimentin expression in MCP cell clusters fixed immediately after isolation. Nuclei stained blue with DAPI and vimentin (mouse anti-vimentin antibody, V-6630, Sigma) is visualized with a TRITC-conjugated anti-mouse IgG1 antibody (Southern Biotechnology). Cell lines SA002.5, LOTBE002.5 passage 26 and SA002, LOTAL002 passage 48.

Figure 8:
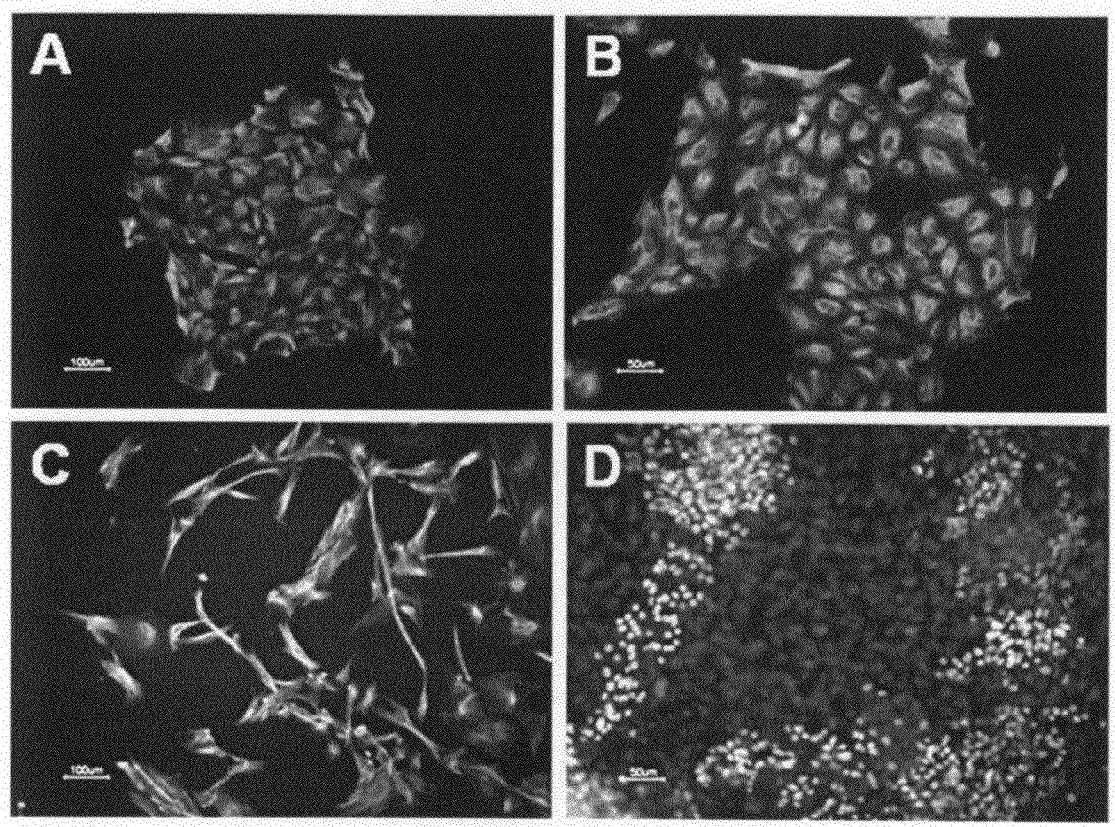

FIG. 8 Illustration of the results obtained by immunohistochemical analysis of the differentiated MCP cells of SA002, LOTAL002 passage 48, SA002.5, LOTBE002.5 passage 42+4 enzymatic passages, SA121, LOTBD121 passage 156+10 and 11 enzymatic passages, respectively and SA461, LOT461 passage 22.

A. Vimentin expression (mouse anti-vimentin antibody, V-6630, Sigma) in MCP cells differentiated 3 days after isolation, visualized with TRITC-conjugated anti-mouse IgG1 antibody (Southern Biotechnology). Nuclei stained blue with DAPI.

B. Desmin expression (mouse anti-desmin antibody, MAB1698, Chemicon) in MCP cells differentiated 3 days after isolation, visualized with TRITC-conjugated anti-mouse IgG1 antibody (Southern Biotechnology). Nuclei stained blue with DAPI.

C. Expression of alpha-sarcomeric actin (mouse anti-alpha sarcomeric actin, A2172, Sigma) in MCP cells differentiated 7 days after isolation, visualized with a FITC-conjugated IgM antibody. Nuclei stained blue with DAPI.

D. Expression of Nkx2.5 (anti-Nkx2.5 antibody, Santa Cruz Biotechnology) in MCP cells differentiated 16 days after isolation, visualized with an Alexa$_{488}$ anti-rabbit IgG antibody.

Figure 9:
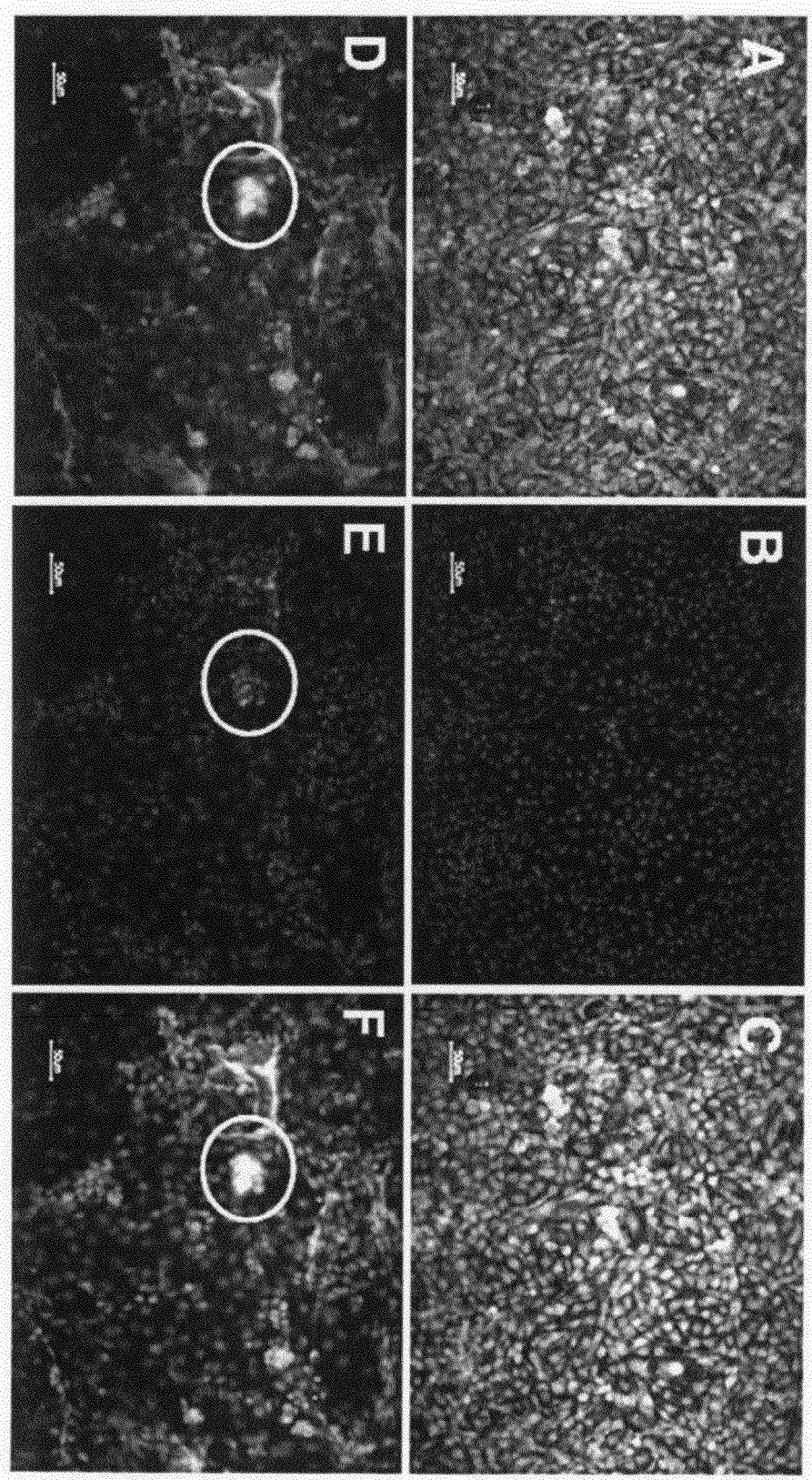

FIG. 9 Illustration of the results obtained by immunohistochemical analysis of basement cells A. Shows expression of α-sarcomeric actin (mouse anti-alpha sarcomeric actin, A2172, Sigma) in basement cells cultivated 36 days after plating in differentiation medium. The antigen marker is visualized with a FITC-conjugated IgM antibody. Cell line used is SA002, LOTAL002, passage 26.

B. DAPI staining of all cell nuclei including the basement cells.

C. Overlay of figure A and B together.

D. Illustrates expression of brachyury (rabbit anti-bracyury, sc-20109, Santa Cruz biotechnology) in basement cells cultivated 15 days after plating in differentiation medium. The antigen marker is visualized with an Alexa$_{488}$ anti-rabbit IgG antibody. Cell line used is SA002.5, LOTBE002.5 passage 32.

E. DAPI staining of all cell nuclei including the basement cells.

F. Overlay of FIGS. 9D and 9E together.

The circles in figures D-F indicate an MCP cell cluster overlaying the basement cells also staining positive for Brachyury.

Figure 10:
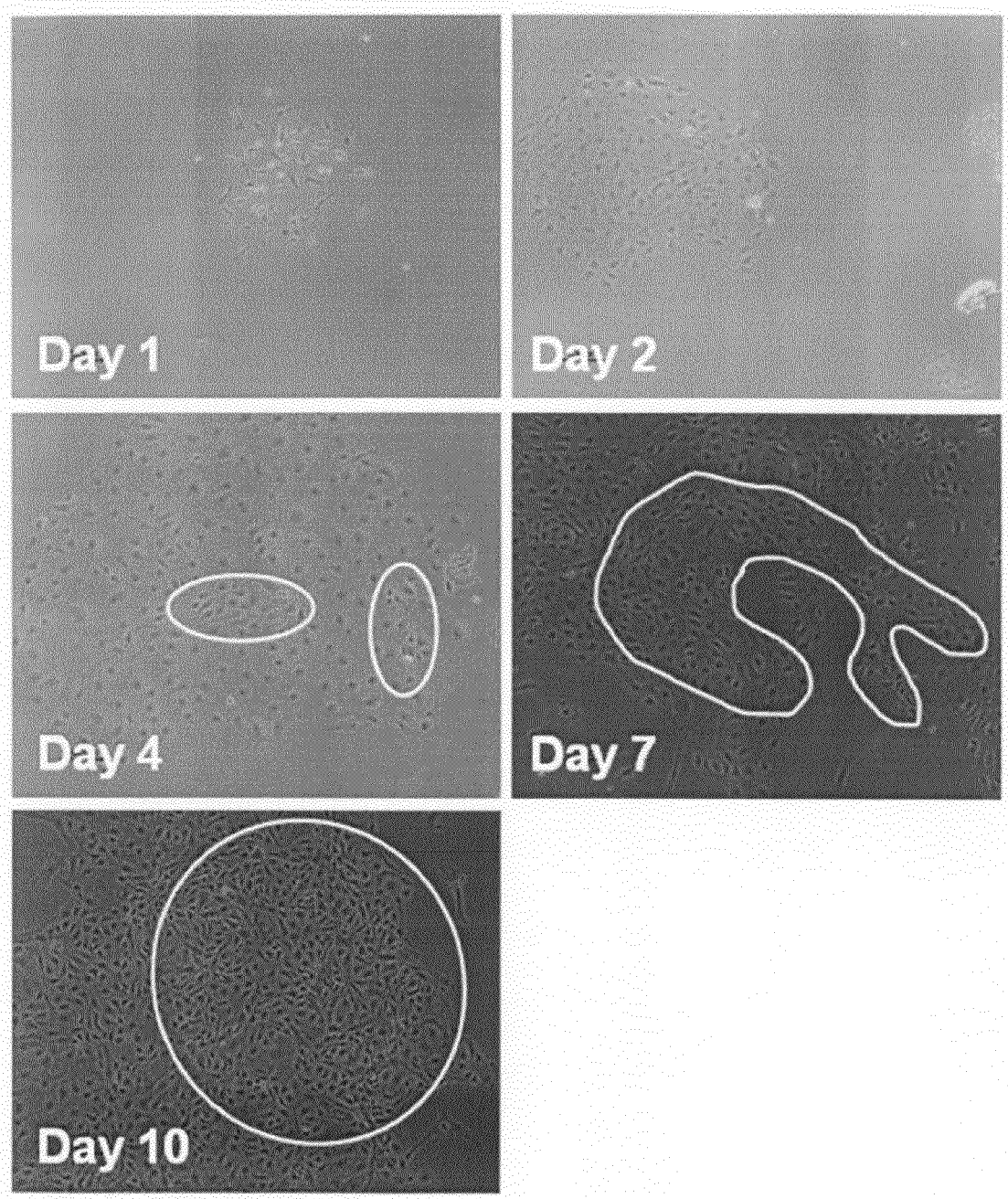
Figure 11:
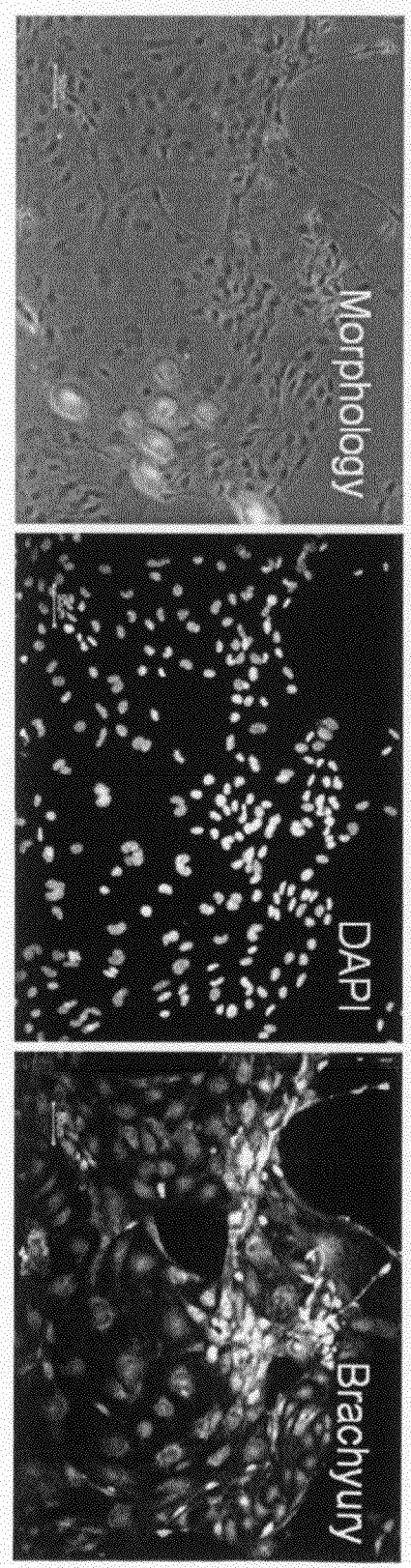

FIGS. 10 and 11. Morphology of isolated and plated MCP cells cultured in B27-containing medium MCP cells were derived from hBS line SA461 and isolated clusters were transferred to new IVF dishes. The cells were subsequently maintained in serum free medium containing 2% B27 supplement.

FIG. 10 shows MCP cell cluster on day 1, 2, 4, 7, and 10 (as indicated) after isolation and plating. Typical appearance of basement cells is indicated at day 4, 7, and 10, and FIG. 11 shows immunohistochemical staining of MCP cells at day 10 after isolation and plating. The figure shows morphology, DAPI staining, and staining for brachyury expression.

Figure 12:
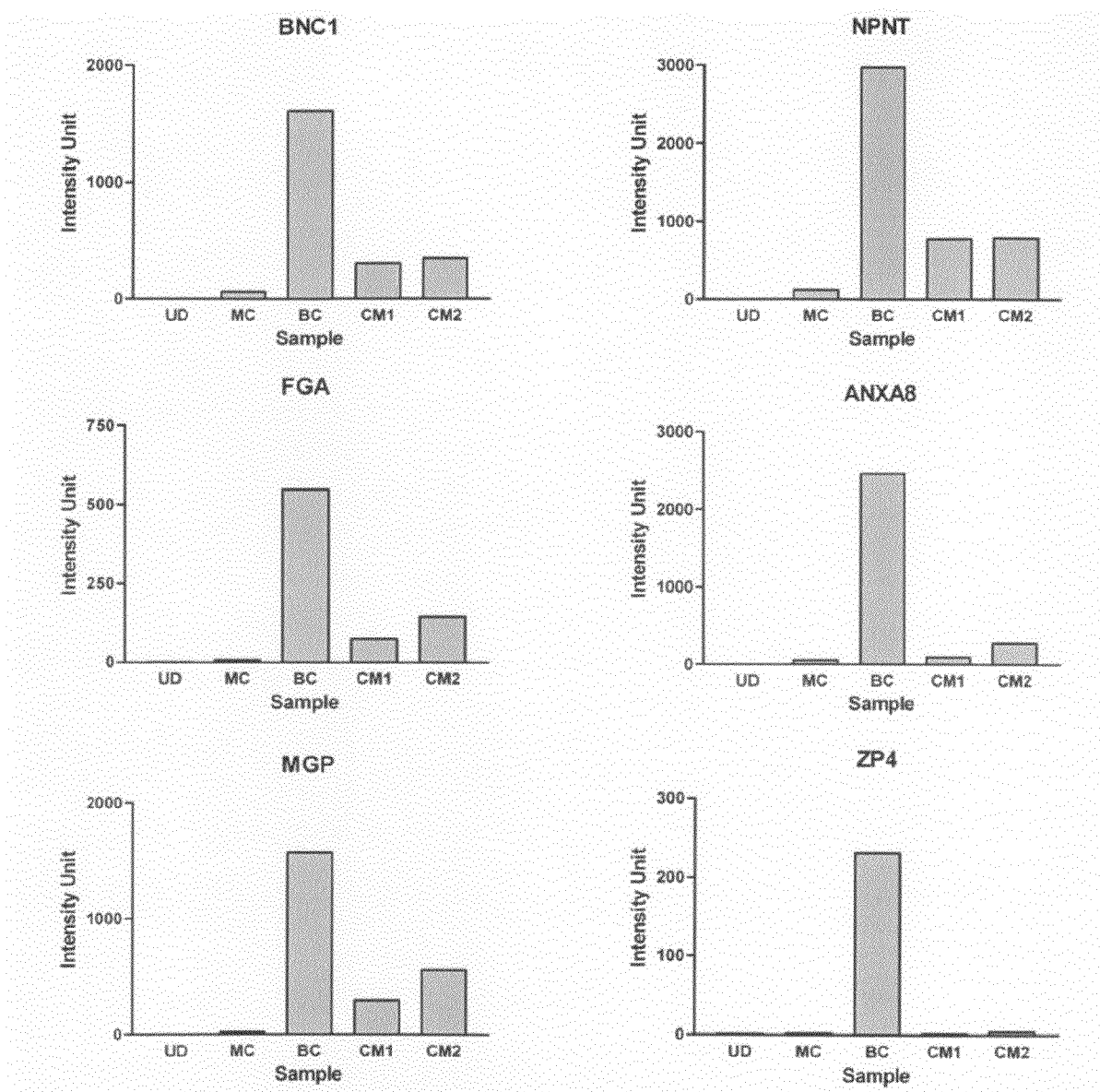
Figure 12:
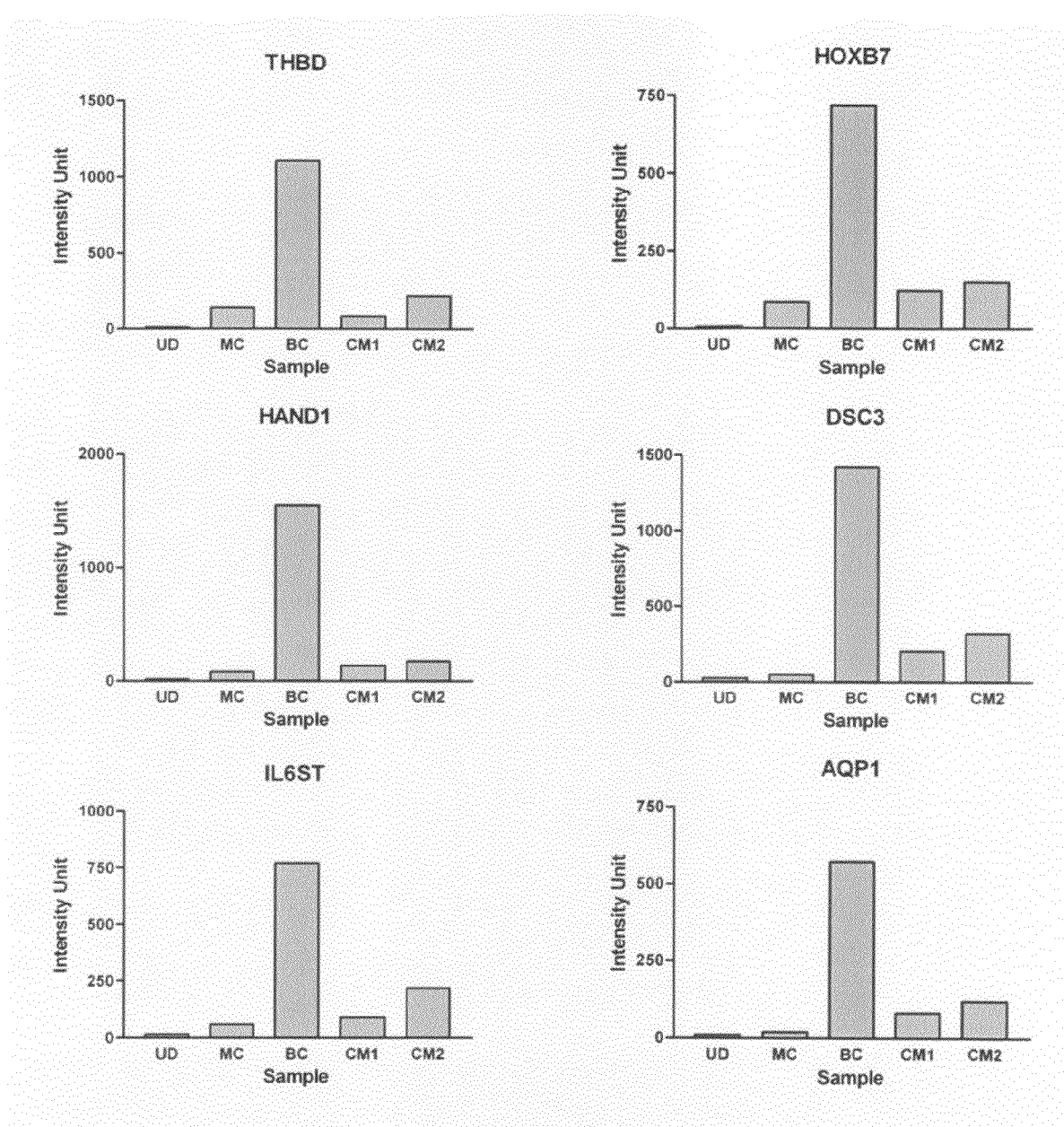
Figure 12:
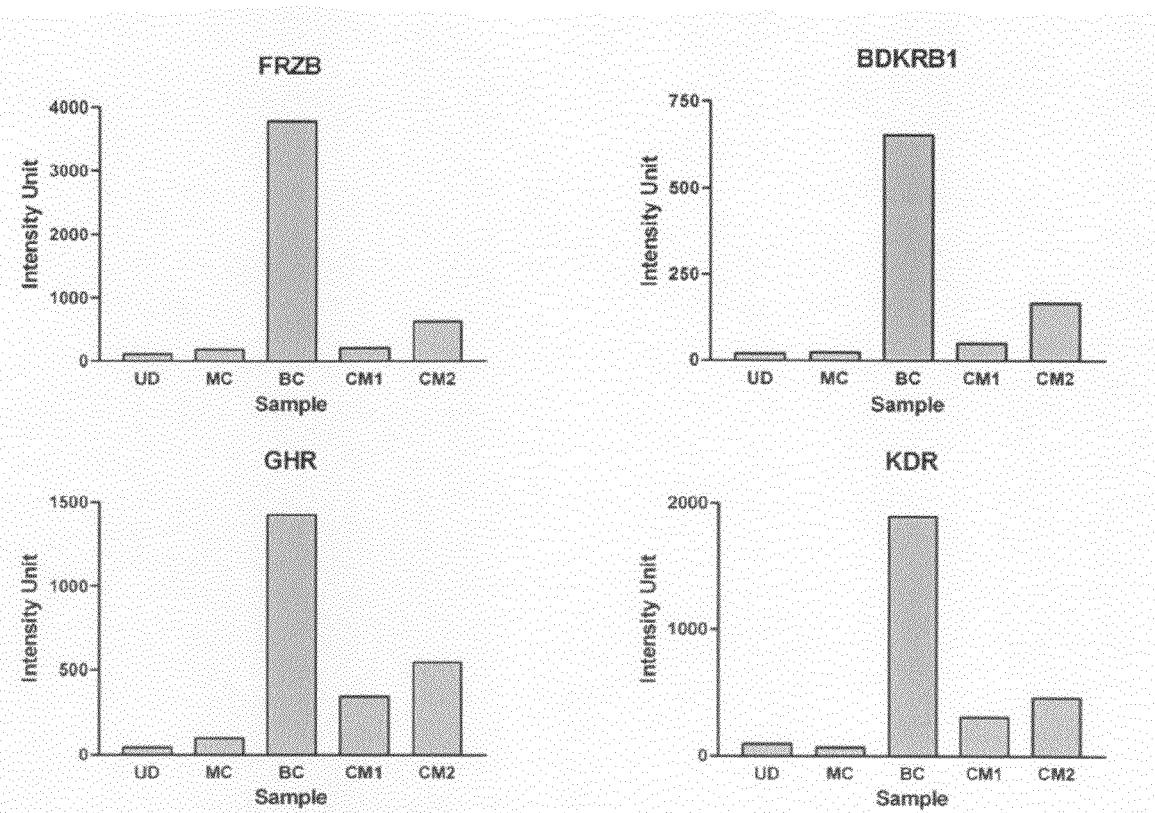

FIG. 12. Gene expression levels of genes specifically expressed in basement cells.

Micro array analysis was performed as described in Example 3 and the gene expression levels of a sub-set of the genes listed in Table II are plotted. The y-axis shows the Intensity Units which is directly proportional to the gene expression level. Panel A shows the values for: Basonuclin 1 (BNC1), nephronectin (NPNT), fibrinogen alpha chain (FGA), annexin A8 (ANXA8), matrix Gla protein (MGP), zona pellucida glycoprotein 4 (ZP4). Panel B shows the values for: thrombomodulin (THBD), homeobox B7 (HOXB7), heart and neural crest derivatives expressed 1 (HAND1), desmocollin 3 (DSC3), interleukin 6 signal transducer (IL6ST), aquaporin 1 (AQP1). Panel C shows the values for: Frizzled-related protein (FRZB), bradykinin receptor B1 (BDKRB1), growth hormone receptor (GHR), kinase insert domain receptor (Flk-1) (KDR). UD=Undifferentiated cells; MC=mixed differentiated cells excluding basement or MCP cells, BC=basement cells, CM1=cardiomyocyte-like cells derived from hBS cells, CM2=cardiomyocyte-like cells derived from hBS cells.

Figure 13:
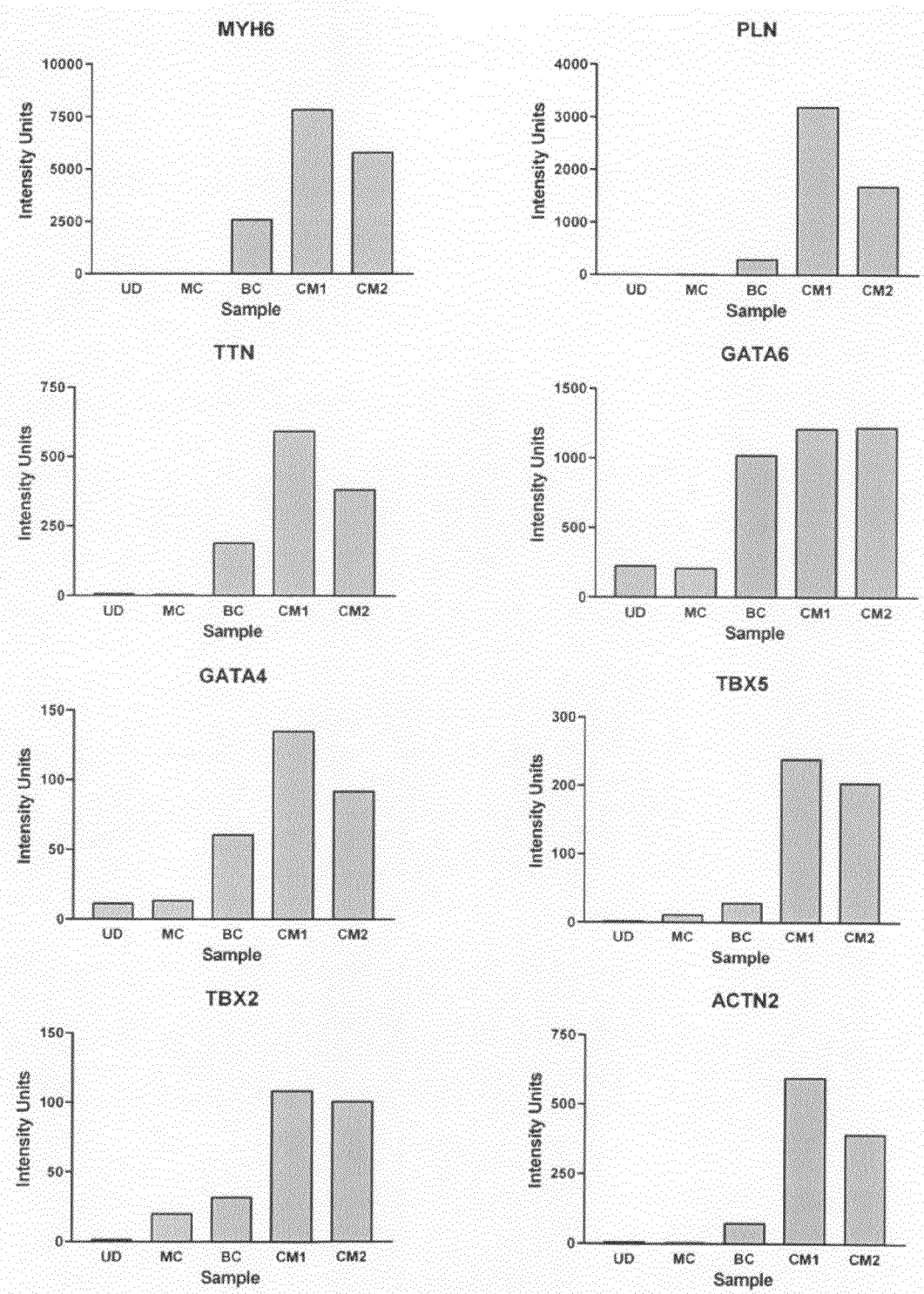
Figure 13:
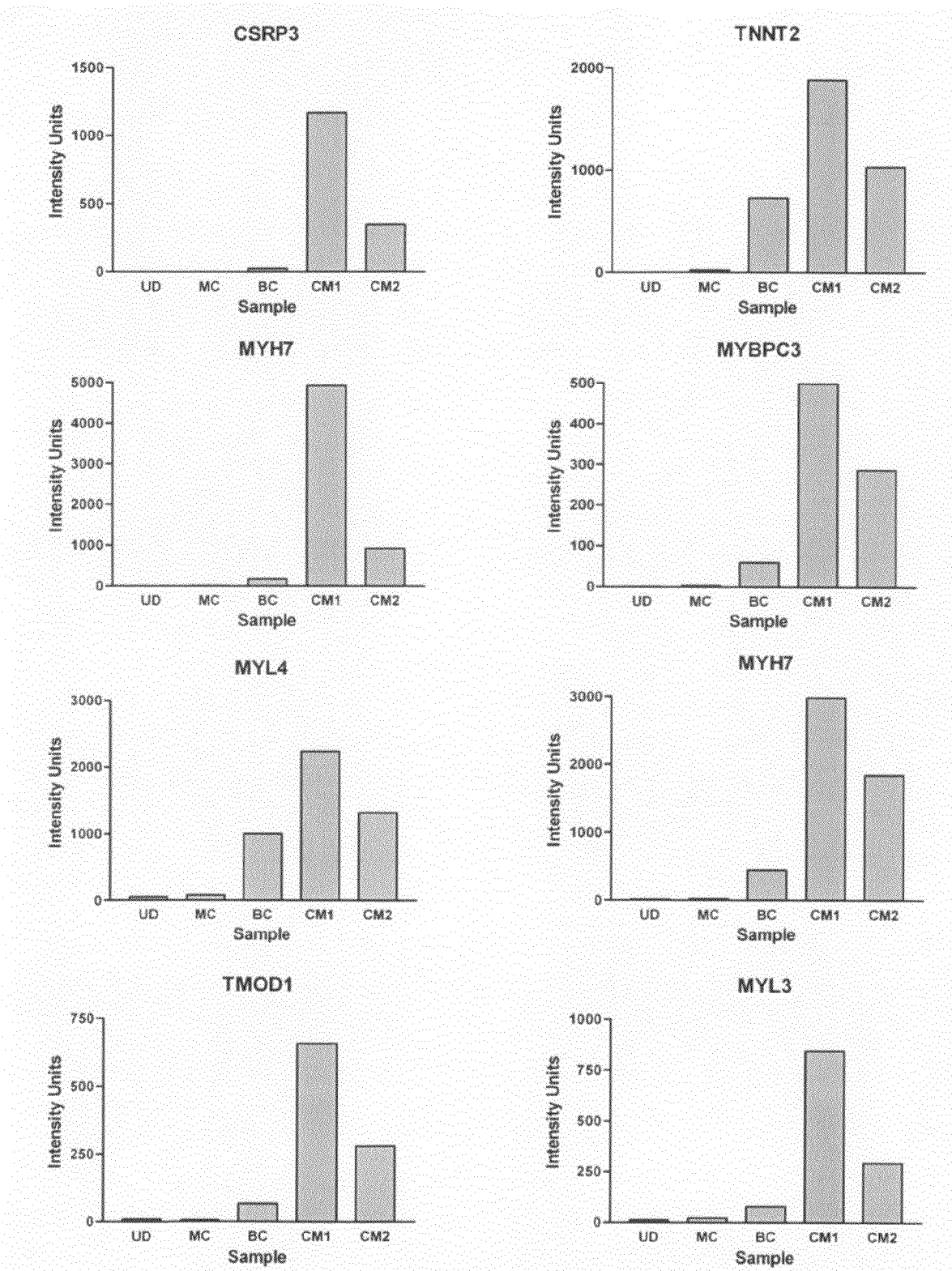
Figure 13:
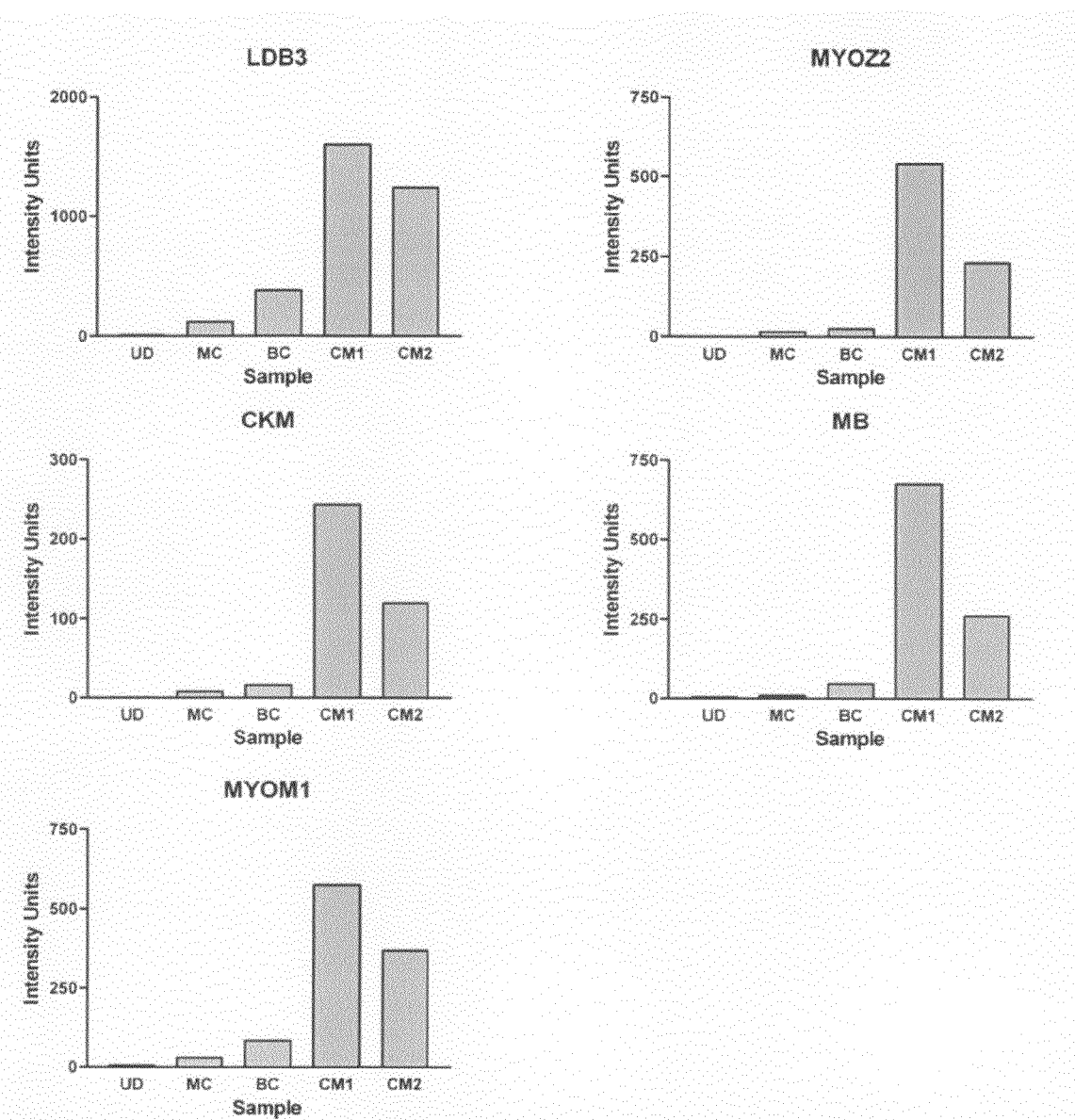

FIG. 13. Gene expression levels of cardiomyocyte marker genes expressed at intermediate levels in basement cells Micro array analysis was performed as described in Example 3 and the gene expression levels of cardiomyocyte marker genes are plotted. The y-axis shows the Intensity Units which is directly proportional to the gene expression level. Panel A shows the values for: myosin heavy polypeptide 6 (MYH6), phospholamban (PLN), titin (TTN), GATA binding protein 6 (GATA6), GATA binding protein 4 (GATA4), T-box 5 (TBX5), T-box 2 (TBX2), and actinin alpha 2 (ACTN2). Panel B shows the values for: cardiac LIM protein (CSRP3), troponin T type 2 (TNNT2), myosin heavy polypeptide 7 (MHY7), myosin binding protein C (MYBPC3), myosin light polypeptide 4 (MYL4), myosin light polypeptide 7 (MYL7), tropomodulin 1 (TMOD1), and myosin light polypeptide 3 (MYL3). Panel C shows the values for: LIM domain binding 3 (LDB3), myozenin 2 (MYOZ2), creatine kinase (CKM), myoglobin (MB), and myomesin 1 (MYOM1) UD=Undifferentiated cells; MC=mixed differentiated cells excluding basement or MCP cells, BC=basement cells, CM1=cardiomyocyte-like cells derived from hBS cells, CM2=cardiomyocyte-like cells derived from hBS cells.

Figure 14:
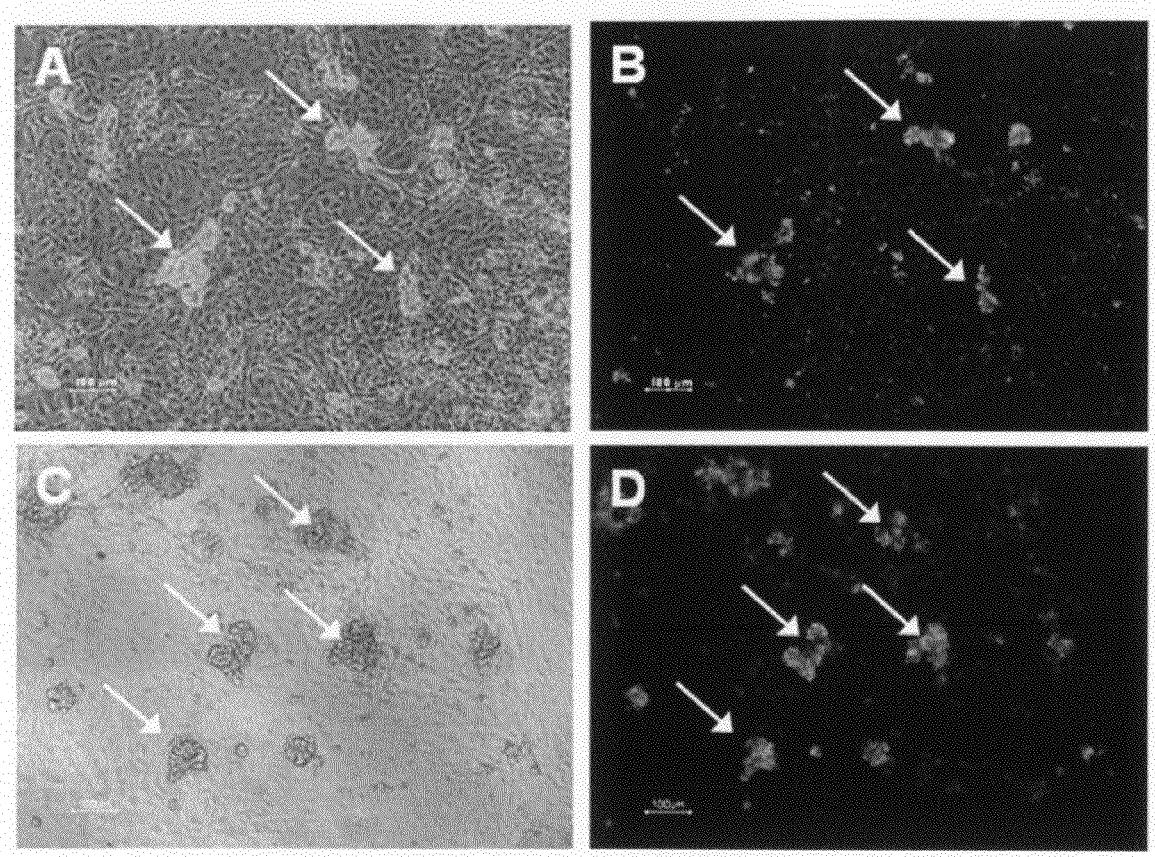

FIG. 14. Staining of MCP cells with MitoFluor™Green Dye.

The figure shows MCP cells stained with the MitoFluor™Green Dye at different concentrations and for different time periods. MCP cells were derived from hBS cell lines SA002 and SA002.5, and stained with MitoFluor™Green Dye at a final concentration of 50-200 nM after 9-20 days in culture. In one experiment, the cells were incubated for 15, 30 and 45 minutes after which the loading solution was removed, and then the fluorescence was observed at different time points after staining. In another experiment, the staining time was varied from 45 minutes up to 19 hours and fluorescence was monitored after each time point. Mitochondria in MCP cells stained with 200 nM of the dye for 30-45 minutes or longer specifically exhibited bright green fluorescence directly after staining or after letting the dye accumulate for an extended time. This staining did not get stronger or more specific by increasing the time for accumulation, neither by increasing the total staining incubation time. Cells treated with 100 nM MitoFluor™Green Dye needed staining for longer than 45 minutes, or time to let the dye accumulate, in order to to exhibit the same pattern as for staining with 200 nM of the dye. Representative pictures of these experiments are shown in A-D. A. Shows the light microscope picture of MCP cells stained with 200 nM of the dye for 45 minutes. B. Shows the corresponding fluorescence picture of MCP cells stained with 200 nM of the dye for 45 minutes; fluorescence was observed directly after staining. C. Shows the light microscope picture of MCP cells stained with 100 nM for 19 hours. D. Shows the corresponding fluorescence microscope picture of MCP cells stained with 100 nM for 19 hours; fluorescence was observed directly after staining. Arrows indicate MCP cell clusters.

Figure 15:
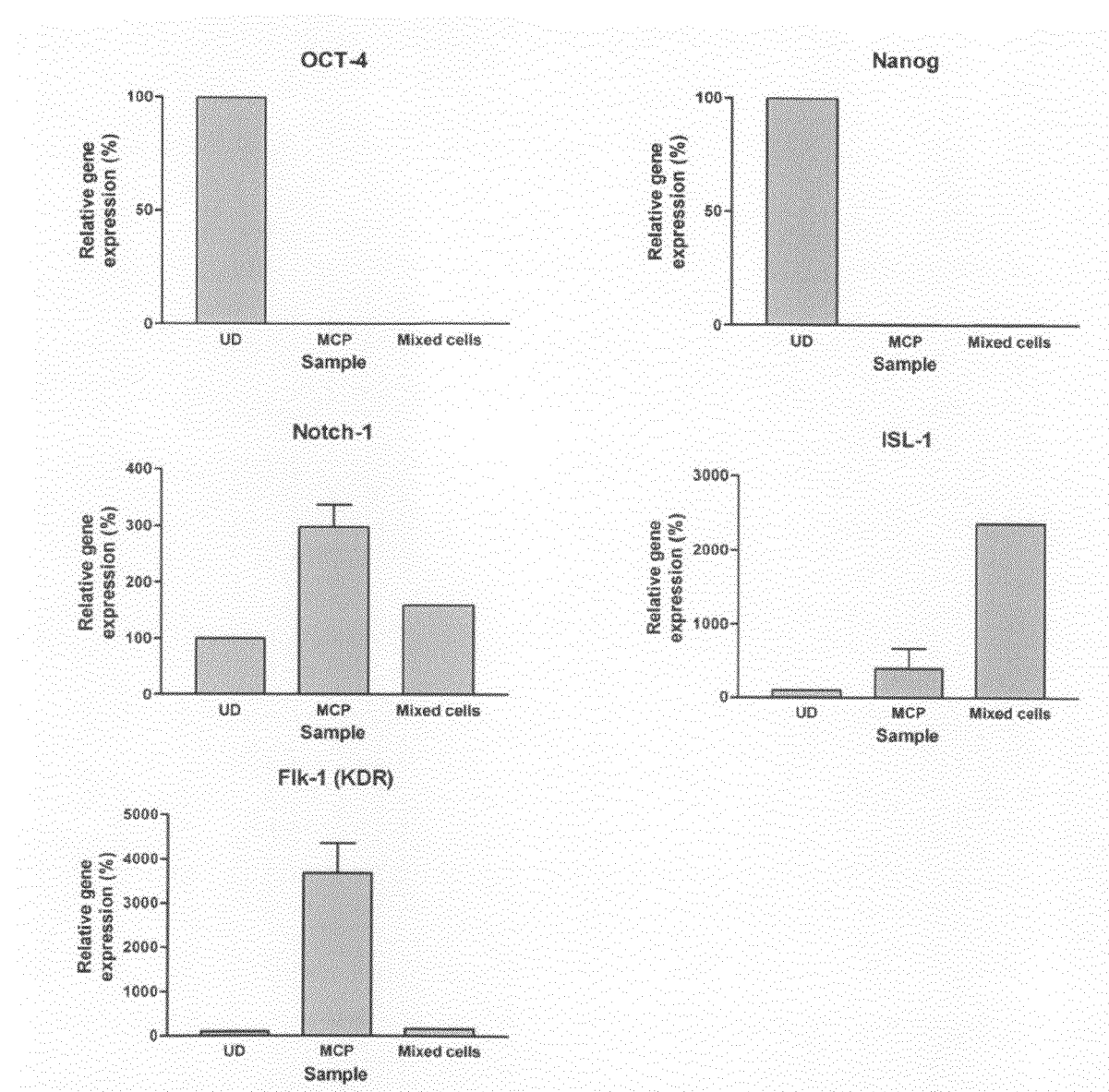
Figure 15:
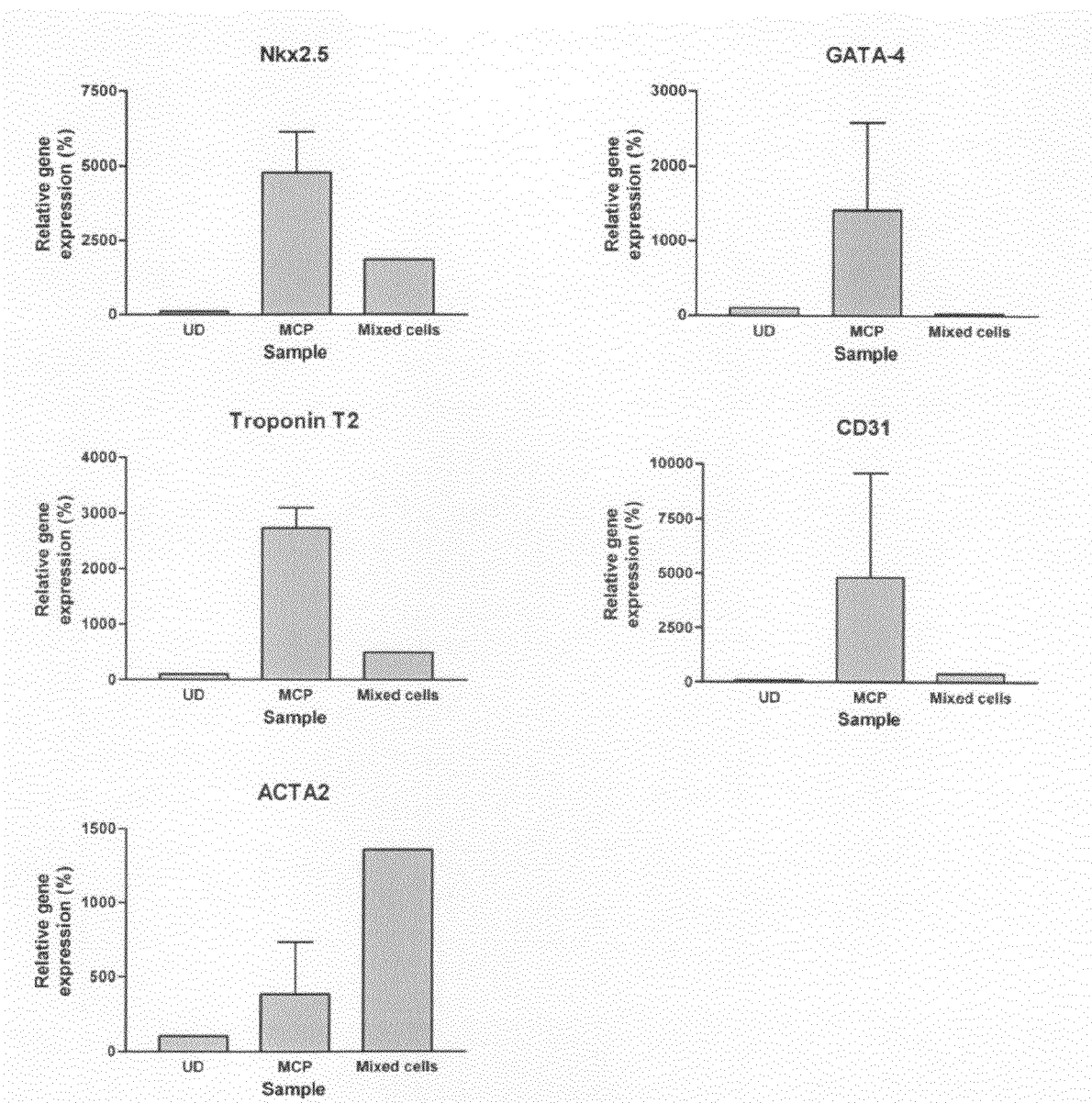

FIG. 15. Gene expression analysis of MCP celler derived from hBS cells cultured on MEF using real-time qPCR MCP cell clusters were derived from hBS cell line SA002 maintained on MEF cells, The MCP cells were harvested, by mechanical dissection of loosely attached cell clusters, 9-18 days after plating of 3D-clusters formed from differentiating hBS cells in 96-well plates. The mRNA levels of specific genes were determined using real-time RT-PCR. The values are expressed as relative gene expression, where the undifferentiated control is set to 100%. There is one observation in each group except for MCP where values are means+SE of three different observations. Panel A shows the gene expression levels of: Oct-4, Nanog, Notch-1, Islet-1 (ISL-1) and Flk-1 (KDR). Panel B shows the gene expression levels of Nkx2.5, GATA-4, Troponin T2, CD31, and ACTA2. UD=Undifferentiated cells; MC=mixed differentiated cells excluding basement or MCP cells.

Figure 16:
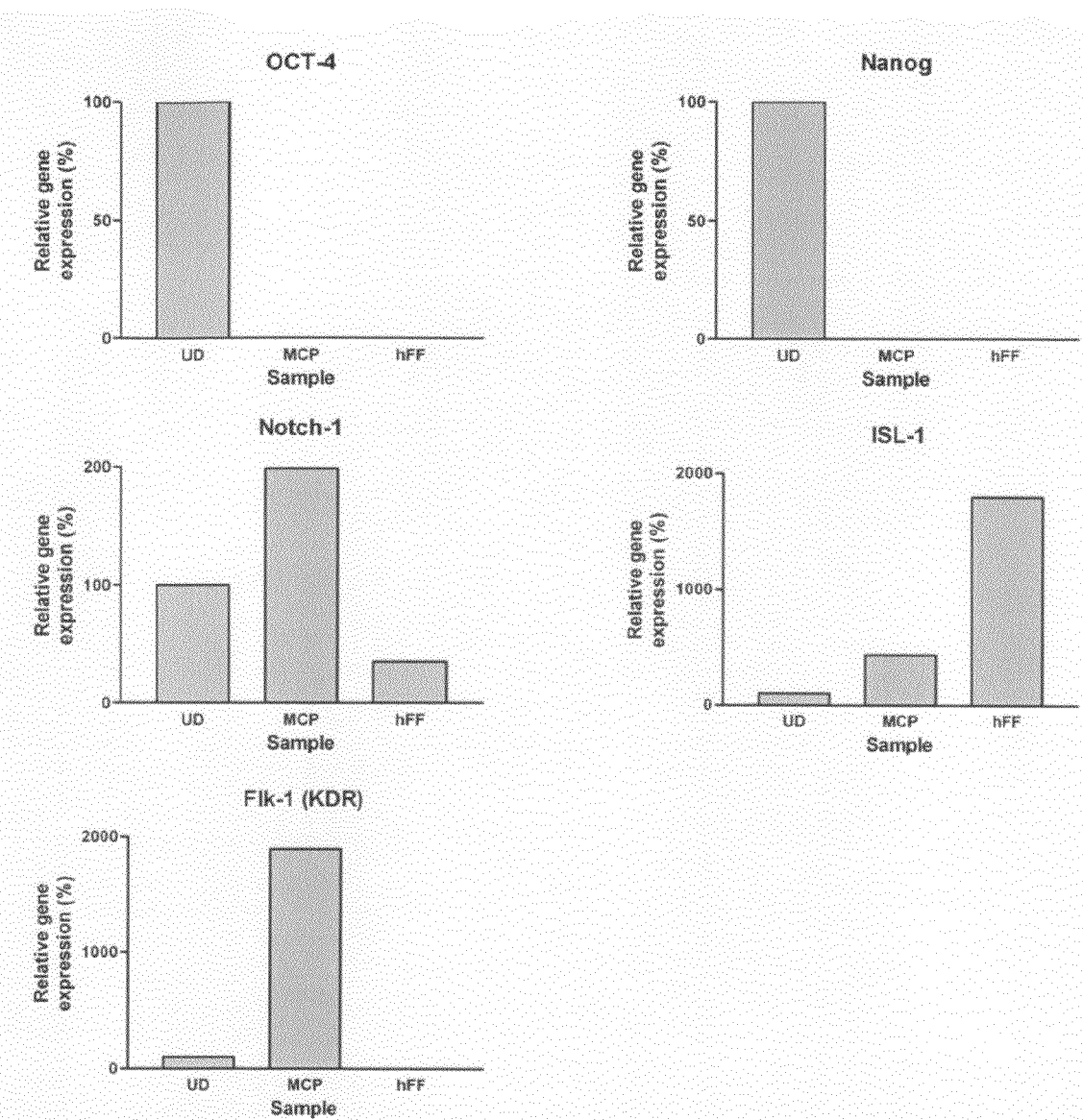
Figure 16:
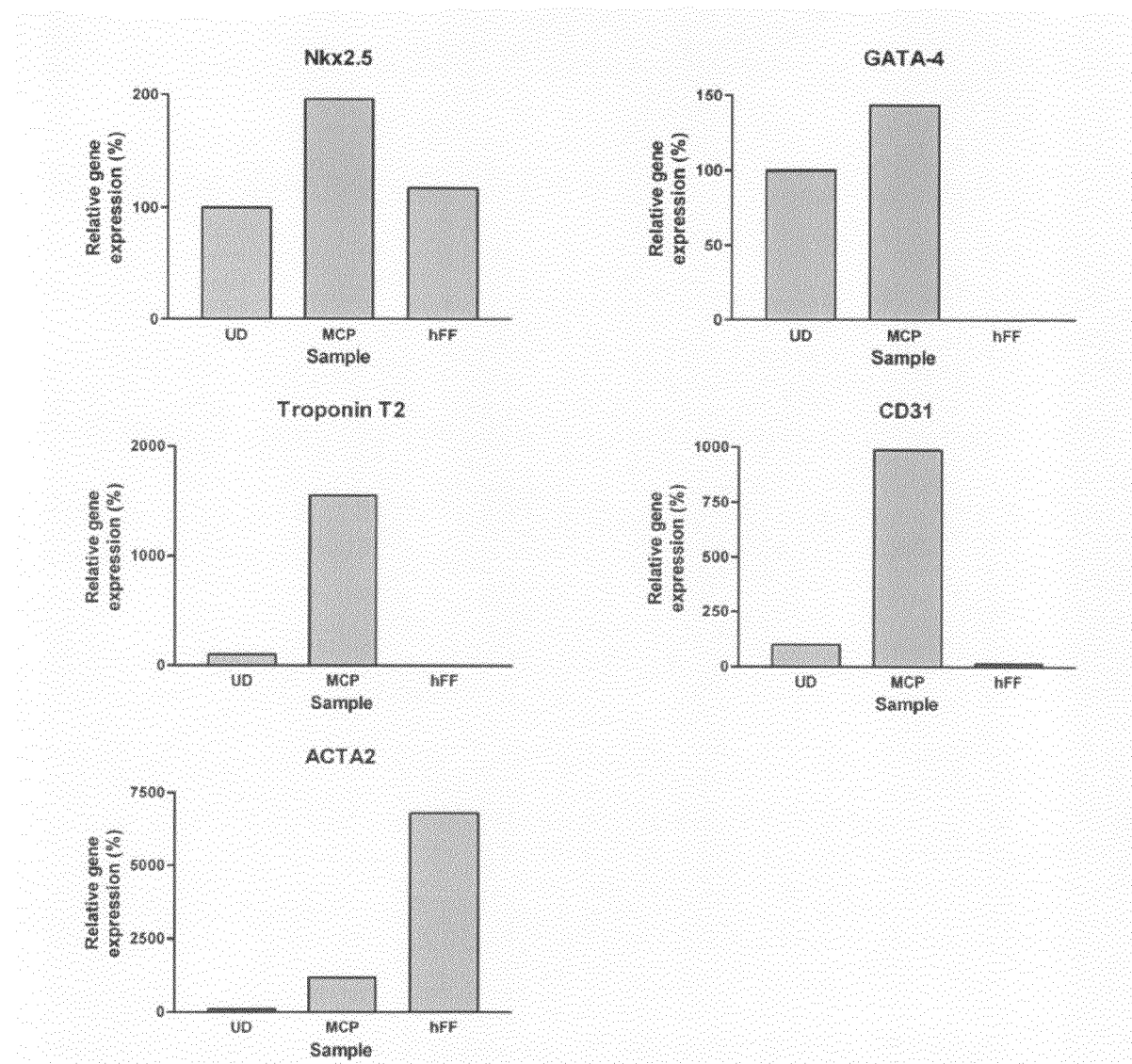

FIG. 16 Gene expression analysis of MCP celler derived from hBS cells cultured on hFF using real-time qPCR MCP cell clusters were derived from hBS cell line E3-SA002 maintained on hFF cells. In the hFF culture system, only loosely attached MCP cell clusters were harvested (9-18 days after plating of 3D clusters formed in 96 well plates). The mRNA levels of specific genes were determined using real-time RT-PCR. The values are expressed as relative gene expression, where the undifferentiated control is set to 100%. Panel A shows the gene expression levels of: Oct-4, Nanog, Notch-1, Islet-1 (ISL-1) and Flk-1 (KDR). Panel B shows the gene expression levels of Nkx2.5, GATA-4, Troponin T2, CD31, and ACTA2. UD=Undifferentiated cells; MC=mixed differentiated cells excluding basement or MCP cells.

hFF=human foreskin fibroblasts.

Figure 17:
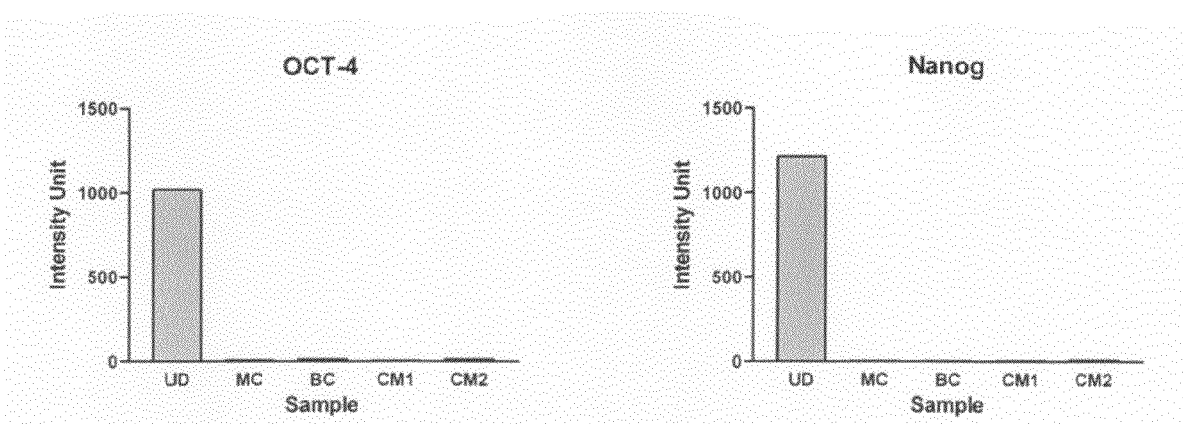

FIG. 17. Gene expression levels of hBS cell marker genes in basement cells.

Micro array analysis was performed as described in Example 3 and the gene expression levels of Oct-4 and Nanog are plotted. The y-axis shows the Intensity Units which is directly proportional to the gene expression level. UD=Undifferentiated cells; MC=mixed differentiated cells excluding basement or MCP cells, BC=basement cells, CM1=cardiomyocyte-like cells derived from hBS cells, CM2=cardiomyocyte-like cells derived from hBS cells.

Figure 18:
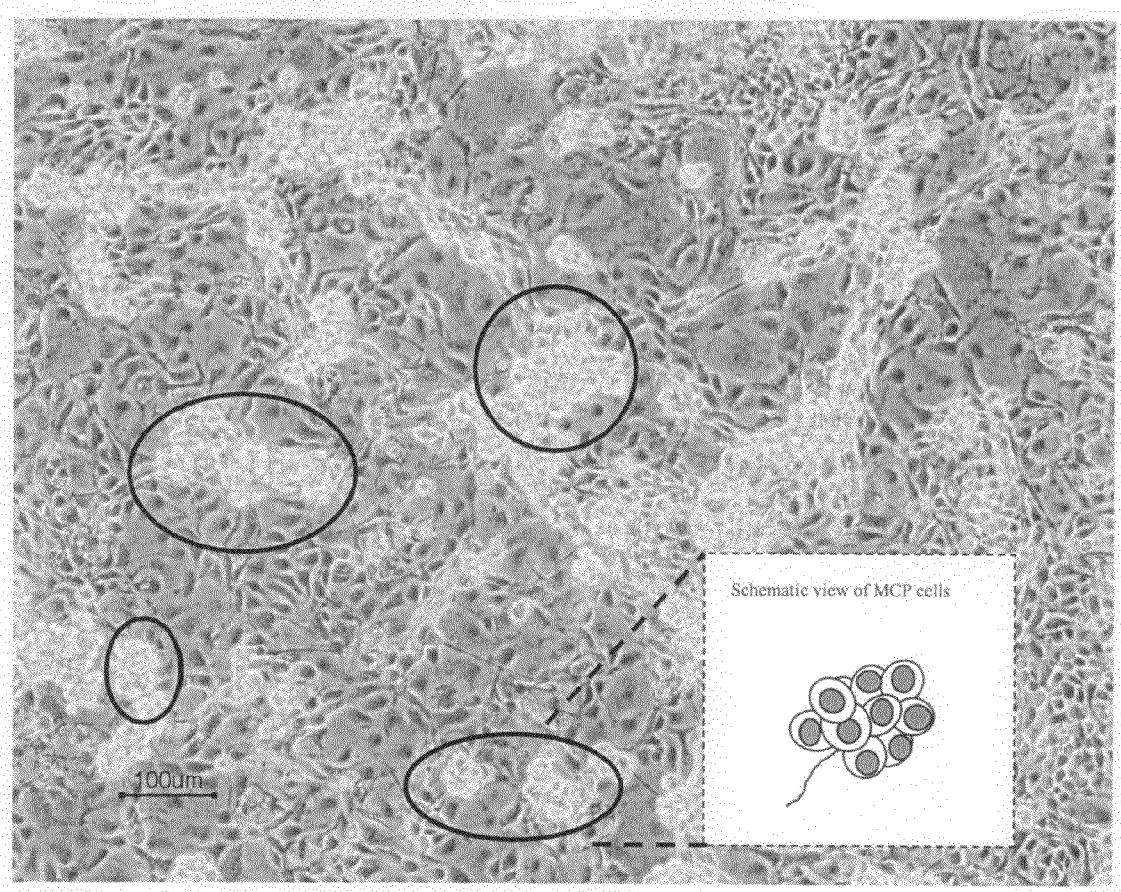

FIG. 18. Morphology of MCP cell clusters overlaying basement cells.

Panels A is from FIG. 2, but includes a schematic sketch of a MCP cluster with the "balloons on a string" morphology.

FIG. 19. Morphology of basement cells.

Is similar to FIG. 1, panel D, and shows the morphology of basement cells with angular shape.

METHODS AND MATERIAL

Specific details relating to the materials employed in the experimental section are given in the following section. The following abbreviations have been used DAPI is intended to mean 4',6'-diamidino-2-phenylindole dihydrochloride hydrate and is a reagent used to visualize cell nuclei.

DMEM is intended to mean the cell culture base medium Dulbecco's Modified Eagle's Medium.

FITC is intended to mean fluorescein isothiocyanate, which is often used as a conjugation to secondary antibodies for visualizing immuno reactions.

Glutamax or (Glutamax™) is intended to mean a glutamine substitute often used as addition to cell culture medium.

IMDM is intended to mean Iscove's modified Dulbecco's Medium.

PEST is intended to mean a mixture of penicillin and streptomycin used as a anti-bacterial cell culture addition.

SCID mice is intended to mean Severely Combined Immuno-Deficient mice.

TRITC is intended to mean Tetramethyl Rhodamine Iso-Thiocyanate which is often used as a conjugation to secondary antibodies for visualizing immuno reactions.

TrypLE Select is intended to mean a recombinant, non-animal alternative for the enzyme trypsin (often derived in porcine), as sold by Invitrogen Corp.

Methods

Starting Material

The starting material for the present invention is suitably pluripotent undifferentiated hBS cells, such as undifferentiated hBS cell lines. Such material can be obtained from Cellartis AB and is also available through the NIH stem cell registry as well as from the UK Stem Cell Bank. Cellartis AB has two hBS cell lines (SA001 and SA002) and one subclone of SA002(SA002.5) available through the NIH.

The Cellartis™ hBS cell lines SA001, SA002, SA046, SA094, SA111, SA121, SA181, SA191, SA196, SA202, SA218, SA240, SA348, SA352, SA399, SA461, SA502, SA506, SA521 and SA540 are also accepted by the UK Stem Cell Bank at the MRC (Medical Research Council).

Those hBS cell lines have been frequently used in the present invention. Characteristics of the hBS cells recommended as starting material are the following: positive for alkaline phosphatase, SSEA-3, SSEA-4, TRA 1-60, TRA 1-81, Oct-4, negative for SSEA-1, telomerase activity, and pluripotency in vitro and in vivo (the latter shown by teratomas formation in immuno-deficient mice) (Methods and protocols as previously shown, Heins et al, WO03055992).

In the following four different ways of obtaining suitable starting material are described:
1. hBS cell line establishment and LOT preparation
2. Xeno-free preparation
3. Enzymatically passaged hBS cells
4. hBS cells transferred to a feeder-free culture system The xeno-free preparation is especially important when the MCP cells are used for therapeutic purposes.

1. LOT Preparation and Characterization Program

The LOT preparation of hBS cell lines constitutes an expansion of the hBS cells in culture and a subsequent freezing by vitrification, which means instant freezing to a crystalline state of more than 100 straws in one single passage according to a standardized method (patent pending, WO2004098285). The morphology of the hBS cell lines are monitored before and after freezing and also in consecutive passages in the subsequent culturing after thawing of cells from the LOT. The quality of the LOT freezing is verified by an examination of the thawing recovery rate. A safety test concerning microbiological safety and human viruses is then performed on the cells and the media in the passage of freezing to make sure the cells are free from contamination. The characterization program performed includes a broad range of methods to validate the differentiation state the of the hBS cell lines. At first a marker expression analysis of the commonly accepted markers for undifferentiated cells (SSEA-1, SSEA-3, SSEA-4, TRA-1-60, TRA-1-81, Oct-4 and ALP) is performed. The genomic stability of the cells through out passage and freezing-thawing cycles is investigated through karyotyping and FISH. The telomerase activity is measured using a Telo TAGGG Telomerase PCR ELISA$^{PLUS}$ kit. The pluripotency of the hBS cells are examined by in vitro differentiation via an embryoid body step and through in vivo differentiation by transplantation of hBS cells under the kidney capsule of immuno-deficient SCID mice.

2. Xeno-Free Preparation

The starting material used herein may furthermore be completely xeno-free derived whereby completely xeno-free MCPs may be obtained for potential use in regenerative medicine and so significantly decreasing the risks of graft rejection and potential transfer of non-human pathogens. For xeno-free derivation of hBS cells all medium and matrix components, feeder cells and other material used may not be derived from or been in contact with any non-human animal material. Suitable components for xeno-free derivation of hBS cells and furthermore xeno-free MCPs are xeno-free derived human fibroblasts, such as human foreskin fibroblasts, serum-free or human serum based culture medium with human recombinant growth factors, differentiation factors and/or potential other additives, and either human recombinant enzymes or sterile mechanical tools for dissociation and propagation of the cells. In the following suitable procedures are described.

Obtaining and Culture Xeno-Free hBS Cells

Surplus human embryo from clinical in vitro fertilization (IVF) treatment was donated after informed consent and approval from the local ethics committee at Göteborg University. The donated embryo was cultured to blastocyst until the age of 5 days in media traditionally used in IVF treatment. The blastocyst was graded according to Gardner as 4AA and according to WO2003055992 as a blastocyst of quality A (expanded blastocyst with many distinct tightly packed ICM cells and a cohesive trophectoderm with many cells). The blastocyst was treated with acid Tyrode's solution (Medicult) solution (ready-to-use concentration) for 15-30 seconds in room temperature in order to remove the zona pellucida and parts of the trophectoderm before placing the inner cell mass cells onto mitomycin-C inactivated xenofree human foreskin fibroblast feeders in xeno-free serum containing a DMEM with osmolarity of around 270 mOsm/kg, supplemented with 20% (v/v) human serum, 4 ng/mL human recombinant bFGF, 1% penicillin-streptomyocin, 1% Glutamax, 0.5 mmol/l β-mercaptoethanol and 1% non-essential amino acids (Gibco Invitrogen Corporation). The blastocyst was then incubated at 37° C. in 5% $CO_2$ in air. 50% of the medium was changed every 2-3 day, and after 10 days the cells were mechanically passaged to fresh hFF feeders. From passage 2 the hBS cells (cell line SA611) have been passaged mechanically using a glass capillary as cut and transfer tool. They have been passaged approximately once a week and have been cultured for more than 11 passages.

The hBS cell line SA 611 was obtained using the procedure mentioned above and has further undergone more than 30 passages.

Establishment of a Human Foreskin Fibroblast Feeder Cell Line (Such as Cell Line hFF003)

Human foreskin samples were aseptically collected in sterile IMDM (Invitrogen) containing 2X Gentamycin from a circumcised 8 week old boy. Skin explants were placed inside 25 cm2 primaria tissue culture flasks (Becton Dickinson) containing IMDM medium (Invitrogen), 1% penicillin-streptomyocin (Gibco Invitrogen Corporation) and 10% of human serum. After approximately 10 days, a confluent monolayer was established. The cells were serially passaged using TrypLE Select (Invitrogen). After expansion they were tested for a standard panel of human pathogens (mycoplasma, HIV of type 1 and 2, Hepatitis of type B and C, Cytomegalovirus, Herpes Simplex Virus type 1 and 2, Epstein-Barr virus, Human Pailloma virus)

Feeder Layer Preparation

Prior to plating the xenofree human fibroblast feeders, the tissue cultured wells are coated with 0.1% recombinant human gelatin (Fibrogen) for a minimum of 1 hour at room temperature. Confluent monolayers of xenofree hFF003 (fifth to eight passage) cells grown in IMDM, 10% human serum and 1% penicillin-streptomyocin were then treated with mitomycin-C (Sigma) for 2.5 hours. Mitomycin-C treated feeders were plated on IVF wells (Becton Dickinson), 200 000 cells per 2.89 $cm^2$ in a medium which was based on DMEM (as above) supplemented with 10% (v/v) human serum, 1% penicillin-streptomyocin, 1% Glutamax, 0.5 mmol/l β-mercaptoethanol and 1% non-essential amino acids (Gibco Invitrogen Corporation). Prior to the placing blastocysts with their inner cell mass cells and cells derived therefrom or hBS cells, the medium was changed to a DMEM (as above), now instead supplemented with 20% (v/v) human serum, 10 ng/mL human recombinant bFGF, 1% penicillin-streptomyocin, 1% Glutamax, 0.5 mmol/l β-mercaptoethanol and 1% non-essential amino acids (Gibco Invitrogen Corporation). (Same medium as in Obtaining and culture xeno-free hBS cells above.)

Preparation of Serum Based Medium

Human serum was obtained from blood-samples from at least 15 healthy individuals (Blodcentralen, Sahlgrenska University Hospital) by collecting the blood in non-heparin coated plastic bags at approximately 8° C. over night whereby the serum could be separated from the clotted material. The serum was further sterile filtered, pooled and frozen in suitable portions. (Prior to use the blood was tested at Blodcentralen, Sweden for the standard battery of pathogens including Hepatitis B, C, HIV, HTLV and syphilis.) The medium was further prepared by adding 20% (v/v) of the thawed serum to a DMEM (as above) together with the other ingredients as described in Obtaining and culture xeno-free hBS cells above.

Freezing and Thawing by Vitrification of Xeno-Free hBS Cells

The hBS cell line SA611 was frozen according to a method described in WO2004098285. Two solutions A and B are prepared (Solution A: Sterile filtered 10% Ethylene glycol, 10% DMSO in Cryo-PBS; Solution B: Sterile filtered 0.3M Trehalose, 20% Ethylene glycol, 10% DMSO in Cryo-PBS) Selected colonies of hBS cell line SA611 were cut in the same way as when the cells are cut for regular passage using a stem cell cutting tool (Swemed Labs International, Billdal, Sweden). The cell pieces are incubated first in 500 ml preheated (37° C.) Solution A for 1 min and then transferred to 25 ml Solution B and incubated for 30 s and then transferred again to a fresh drop of Solution B and incubated for 30 s. The volume was about 40-50 μl. The cell pieces were aspirated into a straw prepared for vitrification and the straw was then closed with a bond. The straw was further plunged into liquid nitrogen.

Several days later straws containing frozen SA611 were thawed as described: Two solutions C and D were prepared (Solution C: Sterile filtered 0.2M Trehalose in Cryo-PBS.; Solution D: Sterile filtered 0.1M Trehalose in Cryo-PBS). Solutions C and D and hBS-medium were preheated at 37° C. The closed straws containing vitrified SA611 were removed from the liquid nitrogen tank. The straw was keep at room temperature for 10 s and then quickly thawed in a 40° C. water bath (within seconds). The straw was cut open in the plugged end using an autoclaved pair of scissors and the content pushed out from the straw into solution C using a syringe. The hBS cells were incubated for 1 min in 500 μl solution C and the transferred to 500 μl solution D and incubated for 5 min. Under a steromicroscope the hBS cell pieces were quickly rinsed in the xeno-free serum based medium and then seeded in a culture dish on top of xeno-free human fibroblast feeder cells in the serum based medium. The cells were then cultured (incubated at 37° C.) and the number of established new colonies were counted and passaged in order to verify the viability of the hBS cells after vitrification.

Characterization of a Xeno-Free hBS Cell Line

The xeno-free SA611 cell line has so far not undergone any LOT preparation and thereto related characterization (as described above) but the still quite thorough characterization so far performed is described in the following paragraphs.

The hBS cell colony cultures were fixed in 4% paraformaldehyde and subsequently permabilized. After consecutive washing and blocking steps, the cells were incubated with the primary antibody overnight at 4° C. The primary antibodies used were specific for Oct-4, TRA-1-60, TRA-1-81, SSEA-1, SSEA-3 and SSEA-4 FITC- or Cy3-conjugated secondary antibodies were used for detection. Nuclei were counterstained with DAPI. The activity of alkaline phosphatese (ALP) was determined according to manufacturer's protocol.

In order to identify cells from the three different germlayers, immunohistochemical analysis was performed as outlined above with the following antibodies: For endodermal cells HNF3β (Santa Cruz Biotechnology, Santa Cruz; http://www.southernbiotech.com) was used. Mesodermal cells were detected by ASMA (company) and ectodermal cells were identified by β-tubulin-III mAb (Sigma-Aldrich). Alkaline phosphatase (ALP) reactions were detected using a commercial kit and following the manufacturer's protocol (Sigma-Aldrich).

Positive reactions in undifferentiated colonies were detected for ALP, Oct4, Tra1-60, Tra 1-81, and SSEA-4 while SSEA-1 was negative.

hBS cells designated for genetic characterization were retransferred to mouse embryonic fibroblasts for two passages or transferred to Matrigel plates (Becton Dickinson) and further cultured for approximately 10 days. The cells were then incubated in the presence of Calyculin A, collected by centrifugation, lysed by hypotonic treatment, and fixed using ethanol and glacial acetic acid. The chromosomes were visualized using trypsin-Giemsa or DAPI staining. For fluorescence in situ hybridization (FISH) analysis, commercially available kits containing probes for chromosomes 12, 13, 17, 18, 20, 21 and the sex chromosomes (X and Y) were used according to the manufacturer's instruction with minor modifications. The slides were analyzed in an inverted microscope equipped with appropriate filters and software. The hBS cell line SA611 was genetically characterized at passage 9-10. The hBS cell line SA611 has a diploid normal karyotype as demonstrated by karyotype analysis. The karyotype is 46 XY. FISH analysis on selected chromosomes confirmed this finding. The karyotype of SA611 has been confirmed normal.

The pluripotency of SA611 was initially tested in vitro by either allowing the hBS cell colonies to spontaneously differentiate on the feeders or by transfer the undifferentiated hBS cell colonies to Matrigel™ coated plates (Becton Dickinson) on which they were allowed to spontaneously differentiate. In both cases the medium was switched to VitroHES™ (Vitrolife, Kungsbacka, Sweden) when differentiation was to be induced. After 3-4 weeks of culture, the colonies were analysed by immunohistochemistry in order to identify cells from the three different germlayers. Positive reactions were identified for the early endodermal marker HN3beta (sometimes also referred to as Foxal), the ectodermal marker β-Tubulin and ASMA (alpha-smooth-muscle actin).

3. Enzymatically Passaged hBS Cells

In this procedure the human fibroblast feeders need not be xeno-free. Accordingly, the feeders can be obtained using different procedures. In the following two different ways are described and the way actually chosen can then correlate to the requirements of the culture conditions, i.e. if xeno-free culture conditions are desired or even needed.

Culture of Human Foreskin Fibroblast Feeders

Commercially available hFFs were obtained from the American Type Culture Collection (CRL-2429 ATCC, Manassas, Va.) and were cultured in Iscove's DMEM (Gibco Invitrogen Corporation, Paisley, Scotland; http://www.invitrogen.com), supplemented with 10% of FBS (Invitrogen) and 1% penicillin-streptomycin. The cells were passaged regularly (weekly) at a split between 1:2 and 1:8 using Trypsin-EDTA (Invitrogen). Confluent monolayer of HFF were treated with mitomycin-C (Sigma) (10 µg/ml for 2.5 hrs) and plated on 0.1% gelatin (Sigma) coated IVF dishes at a density of 70000-80000 cells/cm$^2$ in VitroHES™ medium supplemented with 4 ng/ml hrbasic fibroblast growth factor (hrbFGF, Invitrogen). hFF cells were used as feeders between passage 4 and passage 12.

hFF cell lines and subsequent feeder layer preparation of the same can be performed as described under Xeno-free preparation above.

Transfer of hBS Cells to Enzymatic Propagation Culture

The hBS cell lines SA001 and SA121 (Cellartis AB, Goteborg, Sweden, http://www.cellartis.com) had been established and characterized as previously described [Heins, Noakssson] and in W003055992. Prior to the experiments the lines had been maintained in IVF dishes on mitomycin-C inactivated mEF feeder layers in VitroHES™ medium supplemented with 4 ng/ml hrbFGF and cut manually by using a micro capillary as cutting and transfer tool. To transfer hBS cells from traditional culture to the enzymatic dissociation, the used culture medium was removed and the culture dishes were washed once with PBS (Invitrogen). A volume of 0.5 mL of TrypLE™ Select (Invitrogen) or Trypsin/EDTA (Invitrogen) was then added to each IVF dish. Dishes were incubated at 37° C. until the outer regions of the hBS cell colonies started to round up from the feeder layer. The cell sheet was then broken apart to a single cell suspension by repeated trituration with a pipette, transferred to a centrifuge tube and centrifuged at 400 g for 5 minutes. Supernatant was discarded, the hBS cell pellet was resuspended in fresh VitroHES™ medium and the single cell suspension was seeded into an IVF dish containing a dense feeder layer of inactivated hFF.

Enzymatic Propagation of hBS Cells Using Passage as Single Cell Suspension

For enzymatic propagation the hBS cells were maintained in a culture system consisting of hFF feeder cells at high density and VitroHES™ medium supplemented with 4 ng/ml hrbFGF. Enzymatic dissociation was initiated by removing the culture medium washing the culture dishes with PBS (Invitrogen). A volume of 0.5 mL of TrypLE™ Select (Invitrogen) or Trypsin/EDTA (Invitrogen) was then added to each dish. Dishes were incubated at 37° C. until the outer regions of the hBS cell colonies started to round up from the feeder layer. The cell sheet was then broken apart to a single cell suspension by repeated trituration with a pipette. Subsequently the cell suspension was transferred to a centrifuge tube and centrifuged at 400 g for 5 minutes. Supernatant was discarded and the hBS cell pellet was resuspended in fresh VitroHES™ medium. Cells were then seeded into fresh IVF dishes containing a dense feeder layer of inactivated hFF at split ratios between 1:5 and 1:500. The lower split ratio was used during a so-called adjustment procedure during the very first passages in the new system. After no more than 5 passages the hBS cell line was split at split ratios between 1:20 and 1:500. Cultures were maintained in an incubator at 37° C. and 95% humidity. Used culture medium was replaced with fresh VitroHES™+4 ng/ml hrbFGF every 2-3 days. Depending on the growth speed of the individual hBS cell line the cells were passaged every 6-12 days. Both line SA001 and SA121 have been cultured for more than 20 passages with maintained normal karyotype and further been frozen and thawed according to conventional slow-freezing methods in their normal culture medium supplemented with 10% DMSO.

Characterization of Enzymatically Passaged of hBS Cells hBS cell cultures were fixed in 4% paraformaldehyde for 15 minutes, permeabilized for 5 minutes in 0.5% trition solution (Sigma-Aldrich) and subsequently blocked with 5% FBS in PBS (lnvitrogen). The cells were incubated with primary antibody solution overnight at 4° C. The primary antibodies used were specific for Oct-4, TRA-1-60, TRA-1-81, SSEA-1, SSEA-3 and SSEA 4 . Incubation with FITC- or Cy3-conjugated secondary antibodies (Jackson Immunoreserach Laboratories) was performed for 60 minutes at RT. Cell nuclei were counterstained with DAPI (Sigma). The activity of alkaline phosphatase was determined using an alkaline phosphatase activity detection kit according to the manufacturer's instructions (Sigma-Aldrich). Stainings were evaluated and documented using a Nikon Eclipse TE-2000 U fluorescence microscope. Both SA001 and SA121 showed all the above hBS cell characteristics after more than 20 passages.

For karyotype analysis the hBS cells were incubated in the presence of colcemid, trypsinized, fixed and mounted on glass slides. The chromosomes were visualized by DAPI staining, arranged and documented using an inverted microscope equipped with appropriate filters and software.

For fluorescence in situ hybridization (FISH) analysis, commercially available kits containing probes for chromosomes 12, 13, 17, 18, 21, X and Y were used according to the manufacturer's instruction with minor modifications. The slides were analyzed in an inverted microscope equipped with appropriate filters and software (CytoVision).

SA001 and SA121 both showed normal karyotypes after being cultured in the present system for more than 20 passages. FISH was confirmed normal at even higher passages. Pluripotency was assessed by teratoma formation in SCID mice as described earlier [Heins et al]. In brief, undifferentiated hBS cell colonies were mechanically cut into 200×200-µm pieces and surgically placed under the kidney capsule of severe combined immunodeficient (SCID) mice (C.B-17/Icr-Crl-scidBR; Charles River Laboratories). The mice were sacrificed after 8 weeks and tumours were excised and fixed in 4% paraformaldehyde. Hematoxylin and eosin stained paraffin sections were evaluated histologically for the presence of differentiated human tissue derived from all three embryonic germ layers e.g., neural ectoderm, cartilage, and gut-like epithelium.

All three germ layers were confirmed in the teratomas from both SA001 and SA121 cultured in the present system still after more 20 passages.

A xeno-free cell line, such as SA611, could of course be transferred to and subcultured in the enzymatic passaging system in a similar way as described above in this section.

4. hBS Cells Previously Transferred to a Feeder-Free Culture System

Further examples of hBS cells that can be used in the present invention are hBS cells that have been previously transferred to a feeder-free culture system (WO2004099394 and Sjögren-Jansson E et al).

Colonies of hBS cells can then be dissociated into pieces using a suitable enzyme, e.g. a collagenase, such as collagenase IV or mechanical dissection, using e.g. a glass capillary as cut and transfer tool and further subject to the method as described below in the Examples part below.

EXAMPLES

Example 1

Derivation of Basement Cells from Undifferentiated hBS Cells

Suspension Culture

Undifferentiated hBS cells were maintained and propagated in vitro. At day 4-5 after passage undifferentiated hBS cell colonies were manually dissected using a Stem Cell Cutting Tool and placed in differentiation medium (KO-DMEM supplemented with 1 mM Glutamax, 0.1 mM β-MeOH, 1% NEM, 1% PeST and 20% FBS) in suspension cultures. The cells were maintained in suspension for 1-6 days and subsequently transferred to gelatin-coated tissue culture dishes leading to adhesion of the differentiating cell clusters and continued proliferation and differentiation of the cells. Four days after plating a monolayer of cells appear from the adherent clusters of differentiating hBS cells. These cells grow in a characteristic tight network with appearance resembling a maze which makes areas of basement cells easy to distinguish using light microscopy. The morphology of the basement cells share similarities with primitive endoderm and the cells are epithelial-like. In addition, individual cells are phase-dark, well demarcated, and usually angular in shape. (Illustrated in FIG. 1)

Forced Aggregation

Basement cells can also be obtained from undifferentiated hBS cells using another approach described here. Undifferentiated hBS cells were maintained and propagated in vitro. At day 4-5 after passage undifferentiated hBS cell colonies were detached from the feeder layer by incubation with collagenase IV (200 U/ml), for 10-15 minutes at 37° C. The cell suspension was transferred to a 15 ml tube, and after the cells had sedimented, the supernatant was removed. The colonies were resuspended in Knock Out DMEM supplemented with 20% FBS, 1% penicillin-streptomycin, 1% Glutamax, 0.5 mmol/l β-mercaptoethanol and 1% non-essential amino acids (all from Invitrogen, Carlsbad, Calif.) and dissociated mechanically into small clusters (0.2-0.4 mm) using a pipette. This cell suspension was distributed (200 µl/well) into a 96-well v-bottom plate (Corning incorporated, NY, USA) at a concentration of approximately 4-6 colonies per well and centrifuged for 5 min at 400×g. The plate was then incubated at 37° C. for 6-8 days. The 3D structures that formed were then transferred to gelatin coated dishes containing culture medium (same as above). Four days after plating basement cells appear from the adherent clusters of differentiating hBS cells. Medium was changes every second to third day.

Example 2

Characterization of Basement Cells

Basement cells were derived from undifferentiated hBS cells as described above. They were cultured in differentiation medium (KO-DMEM supplemented with 1 mM Glutamax, 0.1 mM β-MeOH, 1% NEM, 1% PeST and 20% FBS) for up to 37 days. Cells were fixed at various time points in PFA and evaluated by immunohistochemistry (Noaksson et al Stem Cells 2005). Antigen markers used were vimentin, desmin, α-sarcomeric actin and brachyury. The basement cells expressed α-sarcomeric actin and brachyury (FIG. 9) but not vimentin and desmin. Cell lines used were SA002, LOTAL002 (passage 26), SA002.5, LOTBE002.5 (passage 32) and SA461, LOTBF461 (passage 33).

Table I summarizes the obtained results of the IHC analysis of basement cells.

TABLE I

| Antigen marker | Days of Differentiation* | Result | Antibody info |
|---|---|---|---|
| Vimentin | 25 | Negative | mouse anti-vimentin antibody, V-6630, Sigma |
| Desmin | 25 | Negative | mouse anti-desmin antibody, MAB1698, Chemicon |
| α-sarcomeric actin | 36 | Positive | mouse anti-alpha sarcomeric actin, A2172, Sigma |
| Brachyury | 15 | Positive | rabbit anti-brachyury, sc-20109, Santa Cruz Biotechnology |

*Denotes days of differentiation after plating of differentiating hBS cell clusters or pieces on gelatin coated culture dishes.

Based on visual characterization of morphology, the basement cells resemble endothelial cells. To investigate the possible endothelial relation, basement cells were exposed to 1,1'-dioctadecyl-3,3,3',3'-tetramethylindocarbocyanine-perchlorate (DiI)-labeled acetylated LDL (DiI-AcLDL). This dye labels both vascular endothelial cells and macrophages and can be used to specifically identify these cells in mixed cell populations.

Basement and MCP cells were derived from undifferentiated hBS cells as described above. The cell line used for derivation was SA002, LOTAL002 (passage 27). After 3-27 days in culture, the cell dishes containing mixed cells, including basement and MCP cells, were treated with 10 µg/ml Dil-AcLDL (Invitrogen, Carlsbad, Calif., USA) in differentiation medium (KO-DMEM supplemented with 1 mM Glutamax, 0,1 mM β-MeOH, 1% NEM, 1% PeST and 20% FBS) during 4 hours at 37° C. The cells were washed three times with warm (37° C.) PBS and incorporated staining was examined in the fluorescence microscope. No specific staining was observed for neither basement nor MCP cells under these conditions. This indicates that these cells are not differentiated endothelial cells. However, the cells could still constitute an earlier and more immature form of endothelial cells that are not stained by Dil-AcLDL.

Example 3

Micro Array Analysis of Basement Cells
Cell Culture and Differentiation

The hBS line SA002 was propagated and the cells differentiated to basement cells as described above, forced aggregation, example 1. Using light microscopy clusters of basement cells were identified and mechanically isolated using a Stem Cell Tool. For comparison purposes in the micro array experiments, samples of undifferentiated hBS cells, samples from a mixed population of differentiated hBS cells (i.e., no basement cells present), and samples from spontaneously contracting cardiomyocyte-like cells derived from hBS cells (Norstrom et.al 2006, Kehat et.al. 2001) were collected and included in the analysis.

Samples:
1. Undifferentiated hBS cells (passage 33, 36, 37, 39, and 40)
2. Basement cells (passage 22, 23, 26-28, 32, 33, 36, and 37)
3. Mixed population of differentiated hBS (passage 22, 28, and 32)
4. Cardiomyocyte-like cells 1 (passage 23-25, 29, and 35)
5. Cardiomyocyte-like cells 2 (passage 39-41)

RNA Extraction and Micro Array Experiments

Total RNA was extracted from the cells using the Rneasy® Mini Kit (Qiagen) and it was subsequently used for microarray experiments employing GeneChip® Human Genome U133 Plus 2.0 (Affymetrix Inc, Santa Clara, CA, USA) targeting 54,675 transcripts. The RNA samples were amplified using two-cycle in-vitro transcription (IVT). RNA quality and concentration was measured using an Agilent 2100 bioanalyzer and Nanodrop ND-1000 respectively. Total RNA was processed following the GeneChip® Expression 3'-Amplification Reagents Two-cycle cDNA synthesis kit** instructions (Affymetrix Inc, Santa Clara, CA, USA) to produce double-stranded cDNA. This was used as a template to generate biotin-targeted cRNA following manufacturer's specifications. Fifteen micrograms of the biotin labeled cRNA was fragmented to strands between 35 and 200 bases in length, 10 micrograms of which was hybridised onto the GeneChip® Human Genome U133 Plus 2.0 (Affymetrix Inc, Santa Clara, CA, USA) overnight in the GeneChip® Hybridisation oven 6400 using standard procedures. The arrays were washed and then stained in a GeneChip® Fluidics Station 450. Scanning was carried out with the GeneChip® Scanner 3000 and image analysis was performed using GeneChip® Operating Software. Swegene MARC conducted the quality controls, the RNA processing and the hybridization of the arrays. The samples representing undifferentiated hBS cells, basement cells, and mixed populations of differentiated hBS cells were hybridized to the arrays. The arrays were run in duplicates. For additional comparison purposes two samples representing spontaneously contracting cardiomyocyte-like cells derived from undifferentiated hBS cells were also analyzed by micro arrays. These samples are denoted CM1 and CM2 respectively.

Data Analysis

In order to define the family of genes that are up-regulated in the basement cells the fold change (FC) in gene expression between undifferentiated hBS cells and the basement cell was calculated. Genes that were called as Absent by the MAS software in all samples were filtered and not included in further analyses. In the samples 17,436 probes were called as Absent. First, the FC-values were calculated for the basement cells. Genes with an average FC-value<2 were filtered from the data set and only the remaining genes were considered for further analysis.

To identify genes that were specifically up-regulated in basement cells and not in the mixed differentiated hBS cell population or in the CM1 and CM2 samples, the following parameters were calculated:
1) Fold-change (FC) in gene expression between basement cells and undifferentiated hBS cells ($FC_{BC}$)
2) FC in gene expression between the mixed differentiated hBS cells and undifferentiated hBS cells ($FC_{MC}$)
3) FC in gene expression between cardiomyocyte-like cells and undifferentiated hBS cells ($FC_{CM}$). The average of the two preparations of cardiomyocyte-like cells was used in the calculation.

Subsequently the following strategy was used to sort out only genes that were specifically up-regulated in the basement cells:
1) Genes with expression values<100 in the basement cells were removed
2) Genes with $FC_{BC}$<3 were removed.
3) Genes with a $FC_{BC}/FC_{MC}$ ratio<5 were removed.
4) Genes with a $FC_{BC}/FC_{CM}$ ratio<3 were removed.

The remaining 125 genes are listed in Table II and these represent suitable marker genes for the basement cells. In order to further emphasize and illustrate the characteristic gene expression pattern of this group of genes, a sub-set of the genes are also plotted in FIG. 12. Similar to the criteria indicated above, the genes in FIG. 12 were selected based on absolute gene expression levels and fold-change (FC) compared to the reference cell populations (i.e., undifferentiated hBS cells, mixed differentiated hBS cells, and cardiomyocyte-like cells derived from hBS cells). With the exception of one gene (ZP4) all genes display gene expression levels above 500. ZP4 was included based on its specificity (i.e., strikingly low expression in the reference cell populations). Furthermore, the genes in FIG. 12 display a $FC_{BC}$>20 and an $FC_{BC}/FC_{MC}$ ratio>7 which represent stricter inclusion criteria compared to the criteria used to compile Table II. In addition, some of the genes have also previously been associated with embryo development (e.g., DSC3, AQP1, ZP4, FRZB, HAND1).

Notably, the gene expression levels of Oct-4 and Nanog are substantially down regulated in the mixed differentiated cells, basement cells, and the cardiomyocyte-like cells (CM1 and CM2) compared to the undifferentiated hBS cells (FIG. 17), further demonstrating the differentiated phenotypes of the cell preparations.

TABLE II

Summary of genes that are specifically up-regulated in the basement cells.
All FC values in the table are, as indicated above, calculated in relation to
undifferentiated hBS cells. The genes are sorted in descending order based on the
$FC_{BC}$ value.

| UniGene ID | Gene Symbol | $FC_{BC}$ | $FC_{MC}$ | $FC_{CM}$ | $FC_{BC}/FC_{MC}$ | $FC_{BC}/FC_{CM}$ |
|---|---|---|---|---|---|---|
| Hs.136241 | BNC1 | 5362.8 | 205.3 | 1082.0 | 26.1 | 5.0 |
| Hs.435535 | NPNT | 2697.9 | 108.9 | 712.8 | 24.8 | 3.8 |
| Hs.534052 | FMO1 | 1504.7 | 9.7 | 331.6 | 155.7 | 4.5 |
| Hs.492974 | FGA | 1283.7 | 7.7 | 114.6 | 178.5 | 11.9 |
| Hs.591641 | ANXA8 | 1070.6 | 25.4 | 80.2 | 42.1 | 13.3 |
| Hs.306051 | MGP | 983.0 | 13.3 | 265.8 | 74.2 | 3.7 |
| Hs.487027 | RGS1 | 830.2 | 26.7 | 94.1 | 31.1 | 8.8 |
| Hs.468058 | IFIT1 | 541.3 | 14.3 | 55.1 | 37.9 | 9.8 |
| Hs.470277 | WISP1 | 472.4 | 62.5 | 87.0 | 7.6 | 5.4 |
| Hs.270279 | MAB21L2 | 465.2 | 31.7 | 108.4 | 14.3 | 4.2 |
| Hs.591338 | GUCY1A3 | 292.4 | 30.9 | 88.1 | 9.5 | 3.3 |
| Hs.389669 | SH3RF2 | 282.7 | 28.9 | 47.8 | 9.8 | 5.9 |
| Hs.386215 | ZP4 | 257.0 | 2.7 | 3.6 | 96.4 | 71.7 |
| Hs.279746 | THBD | 246.5 | 28.7 | 27.2 | 7.8 | 7.7 |
| Hs.2030 | SYNPO2 | 244.5 | 8.7 | 46.1 | 26.4 | 5.0 |
| Hs.490454 | IGF2 | 214.6 | 2.0 | 54.7 | 107.3 | 3.9 |
| Hs.591706 | PPBP | 200.2 | 1.8 | 9.9 | 111.2 | 20.3 |
| Hs.9730 | CRISPLD2 | 197.2 | 10.9 | 53.8 | 18.1 | 3.7 |
| Hs.508958 | EPAS1 | 191.9 | 17.2 | 55.4 | 11.2 | 3.5 |
| Hs.480615 | TYRP1 | 182.7 | 5.1 | 17.8 | 35.8 | 10.3 |
| Hs.253495 | DCN | 178.0 | 11.6 | 54.6 | 15.5 | 4.4 |
| Hs.527973 | POSTN | 177.2 | 25.3 | 52.6 | 7.0 | 3.4 |
| Hs.487200 | RGS4 | 163.8 | 7.9 | 33.2 | 21.7 | 4.7 |
| Hs.396783 | HAS1 | 153.3 | 2.9 | 30.7 | 52.7 | 5.0 |
| Hs.148907 | HOXB7 | 140.3 | 16.8 | 26.9 | 8.4 | 5.2 |
| Hs.529285 | SLN | 136.5 | 4.3 | 40.7 | 31.6 | 3.4 |
| Hs.370636 | CDH7 | 132.3 | 13.8 | 31.7 | 9.6 | 4.2 |
| Hs.473721 | CYGB | 127.0 | 3.8 | 26.8 | 33.7 | 4.7 |
| Hs.459 | CHRDL2 | 98.5 | 8.3 | 21.7 | 11.8 | 4.5 |
| Hs.500761 | HAND1 | 94.8 | 4.9 | 9.4 | 19.2 | 10.1 |
| Hs.604116 | GREM2 | 85.4 | 9.9 | 16.8 | 9.7 | 5.7 |
| Hs.29802 | ADAMTS6 | 79.5 | 15.5 | 24.2 | 5.1 | 3.3 |
| Hs.443728 | COL21A1 | 77.8 | 1.1 | 17.8 | 68.0 | 4.4 |
| Hs.6314 | COL8A2 | 74.5 | 3.4 | 13.1 | 18.7 | 5.1 |
| Hs.334629 | CNTNAP4 | 70.7 | 6.5 | 12.9 | 10.9 | 5.5 |
| Hs.143873 | ARSI | 69.4 | 5.7 | 12.3 | 12.2 | 5.6 |
| Hs.444834 | COPZ2 | 69.4 | 10.6 | 22.5 | 6.6 | 3.1 |
| Hs.476402 | ADAMTS9 | 66.3 | 4.5 | 14.7 | 15.2 | 5.9 |
| Hs.435291 | RSPO2 | 59.7 | 1.5 | 5.7 | 38.6 | 10.5 |
| Hs.507866 | RGC32 | 59.3 | 3.3 | 6.3 | 18.0 | 9.5 |
| Hs.386726 | DSC3 | 59.0 | 1.9 | 9.7 | 32.4 | 6.3 |
| Hs.75256 | IL6ST | 57.4 | 4.4 | 11.4 | 13.7 | 4.7 |
| Hs.485729 | AKR1B10 | 56.2 | 2.9 | 11.6 | 19.2 | 4.8 |
| Hs.592097 | SLIT3 | 55.5 | 7.8 | 18.2 | 7.2 | 3.0 |
| Hs.190544 | ALOX15 | 48.2 | 3.8 | 5.1 | 12.5 | 9.4 |
| Hs.368542 | AQP1 | 46.2 | 1.7 | 8.3 | 25.3 | 5.3 |
| Hs.2164 | MME | 46.0 | 2.9 | 12.2 | 15.7 | 3.8 |
| Hs.468675 | HOXB6 | 45.6 | 3.5 | 9.1 | 12.9 | 5.0 |
| Hs.498252 | SLC40A1 | 43.5 | 2.5 | 14.5 | 17.3 | 3.0 |
| Hs.553497 | COBLL1 | 42.9 | 3.2 | 6.5 | 13.4 | 6.5 |
| Hs.405156 | GRM7 | 42.1 | 0.4 | 4.3 | 98.3 | 9.8 |
| Hs.37044 | SLC5A12 | 41.9 | 1.4 | 3.3 | 30.7 | 12.8 |
| Hs.136348 | CNTN6 | 40.1 | 5.0 | 7.8 | 8.0 | 5.1 |
| Hs.589848 | FRZB | 39.8 | 1.6 | 4.0 | 27.9 | 10.0 |
| Hs.631510 | ATP7B | 39.7 | 2.6 | 6.6 | 15.5 | 6.0 |
| Hs.9315 | OLFML1 | 39.1 | 2.8 | 12.3 | 13.8 | 3.2 |
| Hs.503500 | SLIT2 | 39.0 | 5.1 | 7.2 | 7.7 | 5.4 |
| Hs.518921 | PRPH | 38.5 | 2.3 | 10.0 | 16.9 | 3.9 |
| Hs.132441 | GAS7 | 34.4 | 6.1 | 9.9 | 5.6 | 3.4 |
| Hs.307734 | SMOC2 | 34.0 | 5.1 | 11.1 | 6.6 | 3.1 |
| Hs.365706 | BDKRB1 | 33.7 | 1.2 | 5.6 | 27.9 | 6.0 |
| Hs.584852 | GHR | 32.1 | 2.1 | 10.0 | 15.2 | 3.2 |
| Hs.480938 | TMEM88 | 30.4 | 2.2 | 3.1 | 13.7 | 10.0 |
| Hs.475353 | COP1 | 29.8 | 0.1 | 7.1 | 268.1 | 4.2 |
| Hs.485581 | LMCD1 | 21.9 | 4.1 | 6.2 | 5.3 | 3.5 |
| Hs.107740 | IL6R | 21.1 | 0.9 | 3.4 | 23.5 | 6.1 |
| Hs.479756 | KDR | 20.9 | 0.7 | 4.2 | 29.3 | 5.0 |
| Hs.182265 | TNFAIP3 | 20.7 | 2.6 | 4.9 | 8.4 | 4.6 |
| Hs.532082 | CEBPD | 19.2 | 1.2 | 5.5 | 16.3 | 3.5 |
| Hs.591492 | ARHGEF3 | 18.9 | 1.8 | 4.1 | 10.5 | 4.6 |
| Hs.20315 | S100A10 | 18.5 | 2.7 | 3.3 | 6.9 | 5.6 |
| Hs.436873 | AQP4 | 18.3 | 1.5 | 5.3 | 12.4 | 3.5 |
| Hs.556244 | GPRC5C | 17.7 | 2.0 | 3.3 | 8.7 | 5.3 |

TABLE II-continued

Summary of genes that are specifically up-regulated in the basement cells.
All FC values in the table are, as indicated above, calculated in relation to
undifferentiated hBS cells. The genes are sorted in descending order based on the
$FC_{BC}$ value.

| UniGene ID | Gene Symbol | $FC_{BC}$ | $FC_{MC}$ | $FC_{CM}$ | $FC_{BC}/FC_{MC}$ | $FC_{BC}/FC_{CM}$ |
|---|---|---|---|---|---|---|
| Hs.57697 | TAC3 | 17.7 | 1.0 | 1.3 | 18.2 | 13.3 |
| Hs.436181 | ARHGAP6 | 17.3 | 2.3 | 3.9 | 8.0 | 4.5 |
| Hs.98428 | SLC16A3 | 16.3 | 1.8 | 4.1 | 8.9 | 4.0 |
| Hs.524688 | SLC9A3R1 | 15.7 | 1.1 | 2.1 | 14.1 | 7.7 |
| Hs.152531 | PXK | 14.9 | 1.9 | 5.0 | 7.8 | 3.0 |
| Hs.24258 | PCSK5 | 14.8 | 2.2 | 2.9 | 6.6 | 5.1 |
| Hs.125180 | CHRNA3 | 14.2 | 2.4 | 4.3 | 5.8 | 3.3 |
| Hs.462214 | ATP1B1 | 14.1 | 1.9 | 4.2 | 7.3 | 3.4 |
| Hs.98206 | PPAP2B | 14.0 | 2.0 | 3.3 | 6.9 | 4.2 |
| Hs.30332 | WNT5B | 13.3 | 2.2 | 4.0 | 5.9 | 3.3 |
| Hs.570608 | GALNT14 | 13.1 | 0.1 | 4.0 | 87.9 | 3.3 |
| Hs.116250 | ITGAV | 13.1 | 1.5 | 2.6 | 8.8 | 4.9 |
| Hs.446438 | RAB37 | 12.9 | 0.7 | 3.1 | 19.4 | 4.2 |
| Hs.128453 | FOSB | 12.3 | 1.2 | 0.1 | 9.9 | 85.5 |
| Hs.1424 | EPHB2 | 12.3 | 2.3 | 2.1 | 5.3 | 5.7 |
| Hs.533683 | GABRA2 | 11.3 | 1.3 | 3.2 | 8.8 | 3.5 |
| Hs.351593 | SLC2A1 | 11.1 | 1.8 | 1.9 | 6.1 | 5.8 |
| Hs.590958 | SLC18A3 | 11.0 | 1.1 | 0.9 | 10.0 | 12.0 |
| Hs.523329 | OGFRL1 | 11.0 | 1.9 | 3.3 | 5.7 | 3.3 |
| Hs.468410 | HPCAL4 | 9.9 | 0.6 | 1.5 | 15.9 | 6.7 |
| Hs.41690 | SOCS3 | 9.5 | 0.8 | 2.6 | 12.4 | 3.7 |
| Hs.156316 | GALNT13 | 9.1 | 0.9 | 1.5 | 10.9 | 6.5 |
| Hs.95120 | TSPAN5 | 8.9 | 1.5 | 1.7 | 6.1 | 5.4 |
| Hs.27475 | ANKS1B | 8.7 | 0.3 | 1.1 | 24.9 | 8.2 |
| Hs.513779 | TRPV2 | 8.6 | 1.2 | 2.7 | 7.4 | 3.2 |
| Hs.461389 | OLFML3 | 8.6 | 0.6 | 2.4 | 15.0 | 3.5 |
| Hs.387300 | KLF2 | 8.5 | 0.8 | 1.6 | 10.2 | 5.3 |
| Hs.47629 | CYB5D1 | 8.4 | 0.9 | 1.0 | 9.1 | 8.3 |
| Hs.353001 | PLD5 | 8.4 | 0.3 | 1.0 | 28.8 | 8.6 |
| Hs.470457 | WASPIP | 7.7 | 1.3 | 1.7 | 5.9 | 4.5 |
| Hs.408434 | ZNF395 | 7.6 | 1.3 | 2.3 | 6.0 | 3.3 |
| Hs.62192 | BMPER | 7.4 | 1.1 | 2.3 | 6.7 | 3.2 |
| Hs.436657 | RIMS1 | 7.4 | 1.1 | 1.7 | 6.7 | 4.5 |
| Hs.432379 | LRRC1 | 7.3 | 1.1 | 2.3 | 6.5 | 3.2 |
| Hs.89605 | FGFR2 | 7.2 | 0.8 | 0.9 | 9.2 | 7.9 |
| Hs.440829 | SFTPD | 7.1 | 0.2 | 1.8 | 35.9 | 3.9 |
| Hs.348365 | SEZ6L2 | 7.0 | 0.9 | 2.1 | 7.9 | 3.3 |
| Hs.130306 | PIGH | 7.0 | 1.2 | 1.6 | 5.7 | 4.3 |
| Hs.46348 | C3HC4 | 7.0 | 0.4 | 1.4 | 19.9 | 5.0 |
| Hs.209226 | F3 | 6.9 | 1.1 | 2.2 | 6.4 | 3.2 |
| Hs.459153 | ZFP36 | 6.6 | 0.8 | 1.5 | 8.0 | 4.4 |
| Hs.291196 | STXBP6 | 6.6 | 1.0 | 1.6 | 6.7 | 4.0 |
| Hs.492280 | TPK1 | 6.2 | 1.0 | 1.7 | 5.9 | 3.6 |
| Hs.591252 | CLU | 6.0 | 0.5 | 1.5 | 15.0 | 4.0 |
| Hs.73809 | SLC4A8 | 5.4 | 0.8 | 0.7 | 6.5 | 7.9 |
| Hs.315369 | PDPN | 4.8 | 0.6 | 0.8 | 8.7 | 6.4 |
| Hs.76152 | KRT19 | 4.7 | 0.8 | 1.3 | 5.6 | 3.5 |
| Hs.618240 | TMEM23 | 4.6 | 0.4 | 1.2 | 11.7 | 3.7 |
| Hs.506458 | PARD6B | 4.0 | 0.4 | 1.3 | 9.8 | 3.1 |
| Hs.116724 | GFPT2 | 3.5 | 0.3 | 0.9 | 13.0 | 4.1 |
| Hs.476604 | VIL2 | 3.3 | 0.4 | 0.7 | 7.5 | 4.7 |
| Hs.482291 | LRBA | 3.3 | 0.5 | 0.9 | 6.2 | 3.6 |

The gene expression profiles of a subset of the genes in Table II are also plotted in FIG. 12. The gene expression profiles are characterized by a low gene expression in the undifferentiated hBS cells and the mixed population of differentiated hBS cells. The gene expression is high in the basement cells and at low to intermediate levels in the cardiomyocyte-like cell preparations. The genes presented in FIG. 12 are: Basonuclin 1 (BNC1), nephronectin (NPNT), fibrinogen alpha chain (FGA), annexin A8 (ANXA8), matrix Gla protein (MGP), zona pellucida glycoprotein 4 (ZP4), thrombomodulin (THBD), homeobox B7 (HOXB7), heart and neural crest derivatives expressed 1 (HAND1), desmocollin 3 (DSC3), interleukin 6 signal transducer (IL6ST), aquaporin 1 (AQP1), Frizzled-related protein (FRZB), bradykinin receptor B1 (BDKRB1), growth hormone receptor (GHR), kinase insert domain receptor (Flk-1) (KDR).

Furthermore, genes indicative of onset of the early cardiomyogenic program were identified in the basement cells and the expression levels of these genes are shown in FIG. 13. The genes presented are: myosin heavy polypeptide 6 (MYH6), phospholamban (PLN), titin (TTN), GATA binding protein 6 (GATA6), GATA binding protein 4 (GATA4), T-box 5 (TBX5), T-box 2 (TBX2), actinin alpha 2 (ACTN2), cardiac LIM protein (CSRP3), troponin T type 2 (TNNT2), myosin heavy polypeptide 7 (MHY7), myosin binding protein C (MYBPC3), myosin light polypeptide 4 (MYL4), myosin light polypeptide 7 (MYL7), tropomodulin 1 (TMOD1), myosin light polypeptide 3 (MYL3), LIM domain binding 3 (LDB3), myozenin 2 (MYOZ2), creatine kinase (CKM), myoglobin (MB), and myomesin 1 (MYOM1).

Notably, these genes are expressed at low levels in the undifferentiated hBS cells and in the mixed population of differentiated hBS cells. However, they are expressed at intermediate levels in the basement cells and they are highly expressed in the cardiomyocyte-like cell preparations (CM1 and CM2). Taken together, these data demonstrate that the basement cells have, despite an immature phenotype, initiated molecular processes that indicate an ability to differentiate towards the cardiomyocyte lineage.

Example 4

Promoter Analysis of Genes Up-Regulated in Basement Cells

In order to identify common regulatory elements for the genes listed in Table II the promoter regions of these genes were investigated. The RefSeqIDs (mRNA transcript identifier) corresponding to the genes were compiled and used as input to the tool PromoSer using default settings (Halees et al. Nucleic Acids Res 2003, 31:3554-3559). A promoter sequence 1000bp up-streams and 50 by down-streams the coding sequence that fulfilled the specified quality criteria was possible to extract for 140 transcripts. These promoter sequences were scanned for common motifs using the Weeder algorithm which is designed to find transcriptional binding sites in sets of sequences from co-regulated genes (Pavesi et al. Nucleic Acids Res 2004, 32:W199-203). To further investigate if the common motifs identified by this algorithm matched experimentally verified binding sites in the human genome, the motifs identified by Weeder were searched against the Transfac® database using the tool PatchTM with "score" threshold set to 80 and "allowed mismatch" set to 1. Only matching motifs from the human genome were considered and reported in Table III. We also investigated whether the binding sites identified through Transfac® had known associating binding proteins as presented in "Binding factor column" in Table III.

hematopoiesis (blood formation) (Huber and Zon 1998, 10(2):103-109, Semin Immunol). Here we propose that GATA-1 can also provide a biological link between cardiogenesis and hematopoiesis by regulating early cellular processes occurring during development. The hemangioblasts, that give rise to vascular cells and blood cells, share developmental pathways with cardiac progenitors and also originates from the mesoderm in the early embryo.

Example 5

Cryopreservation of Basement Cells

Basement cells derived from undifferentiated hBS cells and isolated by mechanical dissection under visual observation can be dissociated into smaller clusters with an enzyme, such as collagenase, dispase, or trypsin and cryopreserved using either standard slow-freezing techniques or vitrification in closed straws (WO2004098285)

Example 6

Derivation of MCP Cells from Undifferentiated hBS Cells

Undifferentiated hBS cells were maintained and propagated in vitro. At day 4-5 after passage undifferentiated hBS cell colonies were manually dissected using a Stem Cell Cutting Tool and placed in differentiation medium (KO-DMEM supplemented with 1 mM Glutamax, 0,1 mM β-MeOH, 1% NEM, 1% PeST and 20% FBS) in suspension cultures. The cells were maintained in suspension for 1-6 days and subsequently transferred to gelatin-coated tissue culture dishes leading to adhesion of the differentiating cell clusters and continued proliferation and differentiation of the cells. Four days after plating a monolayer of cells appear arising from the adherent clusters of differentiating hBS cells. These cells grow in a characteristic tight network with appearance resembling a maze which makes areas of base-

TABLE III

Summary of the results from the motif analysis.
140 promoter regions were extracted corresponding to the genes listed in Table II. Five motifs were identified using the Weeder algorithm and the number of occurrences of each motif in these 140 promoters was calculated for 85% matches and 90% matches respectively. These motifs were searched against Transfac and matching human motifs identifiers are listed in column "Motif Identifier". These motifs were also investigated for known binding factors reported in Transfac and these are listed in column "Binding factor".

| | Data from Weeder motif search tool | | | Matching data from Transfac | | | |
|---|---|---|---|---|---|---|---|
| Motif | # of promoters | >85% match | >90% match | Motif identifier | Score | Binding factor | Motif sequens |
| TCTCCGGT | 140 | 323 | 102 | HS$GPC_02 | 85.71 | GATA-1 | TATCCGGT(+) |
| | | | | HS$EGFR_16 | 80 | Not reported | TCCGCT(+) |
| AACGCTCT | 140 | 117 | 65 | HS$RNU2_04 | 80 | Sp1 | ACGCCC(+) |
| | | | | HS$APOB_11 | 80 | LF-A1(HNF-2) | GAGCCT(−) |
| | | | | HS$CYP24_02 | 80 | VDR | CGCCCT(+) |
| CATCTCCG | 140 | 557 | 117 | HS$GG_03 | 80 | GATA1, POU2F1 | TATCTC(+) |
| | | | | HS$CFOS_18 | 80 | E12 | CATCTG(+) |
| CCGGAGAT | 140 | 255 | 132 | HS$INS_05 | 80 | Not reported | GGAAAT(+) |
| ACGCTC | 140 | 961 | 285 | HS$RNU2_04 | 80 | Sp1 | ACGCCC(+) |
| | | | | HS$APOB_11 | 80 | LF-A1(HNF-2) | GAGCCT(−) |

Taken together, the results suggest that the transcription factors GATA-1, Sp1, LF-A1, VDR, POU2F1, and E12 may be involved in regulating the expression of a sub-set of the genes listed in Table II. The role of GATA-1 is specifically notable since GATA-1 has been reported to be involved in ment cells easy to distinguish using light microscopy. The morphology of the basement cells share similarities with primitive endoderm and the cells are epithelial-like. In addition, individual cells are phase-dark, well demarcated, and usually angular in shape. From those basement cells clusters of MCP cells appeared. The MCP cells are visible using light microscopy and they grow as clusters of small, round, and phase-bright cells appearing as loosely adherent cell clumps overlaying the monolayer of basement cells (FIG. 2). They have a high nucleus-to-cytoplasm ratio. A typical feature of the clusters is the similarity to "balloons on a sting". The MCP cell clusters can either be round or elongated in shape. Cell lines used were SA002, LOTAL002 (passage 34, 42, 48, 55+ED3, 65), SA002.5, LOTBE002.5 (passage 26, 42+ED10), SA121, LOTBD121 (passage 146+ED10, 146+ED11, 146+ED18), SA461, LOTBF461 (passage 22, 33) and SA167 passage 32.

MCP cells can also be obtained from undifferentiated hBS cells using another approach described here. Undifferentiated hBS cells were maintained and propagated in vitro. At day 4-5 after passage undifferentiated hBS cell colonies were detached from the feeder layer by incubation with collagenase IV (200 U/ml), for 10-15 minutes at 37° C. According to forced aggregation, described in example 1, the cell suspension was transferred to a 15 ml tube, and after the cells had sedimented, the supernatant was removed. The colonies were resuspended in Knock Out DMEM supplemented with 20% FBS, 1% penicillin-streptomycin,1% Glutamax, 0.5 mmol/l β-mercaptoethanol and 1% non-essential amino acids (all from Invitrogen, Carlsbad, Calif.) and dissociated mechanically into small clusters (0.2-0.4 mm) using a pipette. This cell suspension was distributed (200 pl/well) into a 96-well v-bottom plate (Corning incorporated, NY, USA) at a concentration of approximately 4-6 colonies per well and centrifuged for 5 min at 400×g. The plate was then incubated at 37° C. for 6-8 days. The 3D structures that formed were then transferred to gelatin coated dishes containing culture medium (same as above). Four days after plating basement cells appear from the adherent clusters of differentiating hBS cells and from those basement cells clusters of MCP cells appeared. Medium was changes every second to third day.

MCP cells could be generated from different hBS cell lines (e.g., SA002, SA002.5, SA461, SA121) and also from hBS cells maintained in various culture conditions (e.g., cultured on MEF or hFF).

Enrichment of MCP cells can be achieved by changing the differentiation medium to CGM-medium (Base medium composed of 35% IMDM and 65% DMEM: F12, supplemented with 1% PeST and Glutamax and made to a final concentration of 3.5% FBS, 2% B-27, 0.1 mM β-MeOH, 10 ng/ml EGF, 20 ng/ml bFGF, 4 nM Cardiotrophin-1, and 40 nM Thrombin). By maintaining the monolayer of basement cells in this medium the number of MCP cells is increased compared to the standard differentiation medium.

Example 7

Isolation of MCP Cells Derived from Differentiated hBS Cells

The MCP cells appeared as loosely adherent cell clusters overlaying a basement cell type with distinct morphology. The MCP cell clusters could be isolated by mechanical dissection using a Stem Cell Cutting Tool. In addition, at various time points some larger clusters of MCP cells also spontaneously detached from the underlying cell layer and these were recovered while floating in the culture medium. It is also possible to recover the MCP cells using mild enzymatic treatment. The MCP cells were collected by pooling two washes with PBS, one wash with 0.5 mM EDTA (1-2min), and one wash with Trypsin-EDTA (2-3 min) at room temperature under visual control. Cell lines used were SA002, LOTAL002 (passage 34, 42, 48), SA002.5, LOTBE002.5 (passage 26, 42+ED10), SA121, LOTBD121 (passage 156+ED10, 156+ED11) and SA461. LOTBF461 (passage 22, 33).

Example 8

Propagation of MCP Cells on Feeder Cells

MCP cells were derived and isolated as described above (forced aggregation) and subsequently cultured on cardiac mesenchymal cells or END2 cells in order to create a co-culture system for propagation and/or differentiation of isolated progenitor cells. To obtain cardiac mesenchyme, cells derived from outgrowths of human heart biopsy explants (dx auriculus) were cultured at a density of 10 000 celler/cm$^2$ in culture medium containing DMEM/F12, 1% PeST, 1 mM Glutamax and 10% FBS. These cells are referred to as cardiac mesenchymal cells. The cells were passaged at approximately 80% confluency by means of 0.25% Trypsin/EDTA treatment.

END2 cells were cultured in medium containing DMEM/F12, 1% PeST, 1% NEM, 1 mM glutamax and 7.5% FBS. The cells were dissociated with 0.25% Trypsin/EDTA when approaching 100% confluency and generally split 1:6-1:8 every third to fourth day.

In order to stop cell division, cardiac mesenchymal cells and END2 cells were treated with medium containing Mitomycin C at a final concentration of 10 µg/ml during approximately 3 hours. The cells were washed three times with PBS and then dissociated with 0.25% Trypsin/EDTA. After centrifugation, the pellet was dissolved in the respective culture medium and seeded on plastic, for END2 cells coated with 0.1% gelatin, at a density of 50 000-70 000 cells/cm$^2$.

MCP cells were derived from undifferentiated hBS cells and isolated by mechanical dissection using a Stem Cell Cutting Tool as described above. The cell line used for derivation of progenitor cells was SA002, LOTAL002 (passage 58 and 61). Isolated MCP cell clusters were plated in dishes with Mitomycin C treated cardiac mesenchymal cells or END2 cells as feeder cells. The progenitor cells attached to both feeder layers and remained attached for a couple of days. Compared to gelatin coated controls without feeder cells, the MCP cells remained attached without flattening out for a longer time in contact with feeder cells. One beating cluster transferred to cardiac mesenchymal cells was beating also after replating. Together these observations suggest that the progenitor cells need to grow in close connection with other cell types (or their excreted products), giving them support or signals that make the progenitors stay in their original state without differentiating. Changing the conditions, however, could make the progenitor proliferate or initiate differentiation towards the cardiac or other lineages.

Example 9

Identification and/or Separation of MCP Cells by Mitochondria Staining

MitoFluor™Green Dye (Invitrogen, Carlsbad, Calif., USA) selectively stains mitochondria of live cells by diffusing across the plasma membrane and accumulating in active mitochondria where it becomes fluorescent. The MCP cells were exposed to this dye in order to investigate their staining pattern.

MCP cells were derived from undifferentiated hBS cells as described above, forced aggregation, example 1. The cell lines used for derivation were SA002, LOTAL002 (passage 21, 23 and 31) and SA002.5, LOTBE002.5 (passage 44). After 9-20 days in culture, the medium in the culture dishes was removed and prewarmed (37° C.) growth medium (DMEM/Glutamax, 0,1 mM β-MeOH, 1% NEM, 1% PeST and 20% FBS) containing the MitoFluor™ probe at a final concentration of 50-200 nM was added. In one experiment, cells were incubated for 15, 30 or 45 minutes under normal growth conditions after which the loading solution was replaced by fresh prewarmed medium without the staining dye. The fluorescence was observed using a fluorescence microscope at different time points after staining, allowing the dye to accumulate for different time periods. In another experiment the staining time was varied from 45 minutes up to 19 hours and fluorescence was monitored after each time point. Mitochondria in MCP cells stained with 200 nM of the dye for 30-45 minutes specifically exhibited bright green fluorescence directly after staining (FIG. 14). This staining did not get stronger or more specific by increasing the time for accumulation, neither by increasing the total staining incubation time. Cells treated with 100 nM MitoFluor™Green Dye needed staining for longer than 45 minutes, or time to let the dye accumulate, in order to exhibit the same pattern as for staining with 200 nM of the dye. With 50 nM of the staining dye, cells were only weakly stained except for the longest exposure/accumulation times. These results indicate that MCP cells can be distinguished from other cell types by use of the MitoFluor™Green Dye. Thus, this dye can be used to identify and/or isolate MCP cells from mixed cell populations. In particular, FACS can be used to enrich cell populations of MCP cells stained with MitoFluor™Green Dye.

Example 10

Re-Plating of Isolated MCP Cells

Isolated MCP cells, either aspirated or manually dissected, were transferred to new tissue culture dishes. The MCP cell clusters attached and spread into a monolayer of cells. Cells with various morphologies can be observed from different clusters (FIG. 3). Some clusters give rise to spontaneously contracting outgrowths with cardiomyocyte-like morphologies. Notably, some clusters also differentiate to the cell type described as the basement cells (see Example 1) from which the MCP cells were originally isolated. Within a few days in culture, new MCP cells can be observed overlaying the basement cells (FIG. 4). This indicates that, at least a subfraction of the MCP cells can differentiate into the basement cell type which subsequently gives rise to new MCP cells. Cell lines used were SA002, LOTAL002 (passage 34, 48, 55+ED3), SA002.5, LOTBE002.5 (passage 26, 42+ED4), SA121, LOTBD121 (passage 156+ED10, 156+ED11) and SA461, LOTBF461 (passage 22, 33).

Example 11

Differentiation of MCP Cells

The possibility to isolate, transfer, and re-plate MCP cells in new culture dishes makes these cells very suitable for setting up models to test various substances, growth factors, and compounds for their effect on cell differentiation. MCP cells can be re-plated in various culture media. As indicated above the MCP cells can be re-plated in differentiation medium which contains 20% FBS. It is also possible to re-plate the cells in differentiation medium without serum. In serum containing medium the MCP cells differentiate into monolayers with various morphologies but in the absence of serum a more homogenous differentiation appears to occur and most of the MCP cell clusters will gain the morphology as depicted in FIG. 6. Cell lines used were SA002, LOTAL002 (passage 55+ED3), SA002.5, LOTBE002.5 (passage 26) and SA461, LOTBF461 (passage 33).

To stimulate differentiation of MCP cells to specific cell types, e.g. contracting cardiomyocytes, various culture conditions can be tested and evaluated. For example, the surface on which the MCP cell clusters are seeded can be either non-modified tissue culture dishes or the dishes can be coated with various extracellular matrix components (e.g., Matrigel, fibronectin, laminin, collagen, etc.) In addition, components in the culture medium can be tested, either alone or in combination (e.g. serum concentration, presence of medium supplements such as K-SR, ITS, and B-27, growth factors such as members of the FGF and BMP families, 5-aza deoxycytidine, DMSO, retinoic acid, ascorbic acid, and ASA).

Example 12

Culture of MCP-Cells in B27-Containing Culture Medium

Undifferentiated hBS cell colonies (cell line SA461 Lot BF461) were mechanically transferred to suspension cultures in differentiation medium containing Knockout DMEM, 1 mM Glutamax, 0,1 mM β-MeOH, 1% non-essential amino acids, 1% PEST, 20% FBS. After two days the differentiating hBS cell clusters were plated and maintained in IVF-dishes in differentiation medium. Medium changes were done every second day in which half of the medium volume was replaced with fresh medium. At day 9 after plating the areas of basement cells were observed and at day 12 MCP were apparent and overlaid the basement cells. At day 19 MCP clusters were mechanically isolated and transferred to a new IVF-dish in serum-free medium supplemented with B27 (Knockout DMEM, 1 mM Glutamax, 0,1 mM β-MeOH, 1% non-essential amino acids, 1% PEST, 2% B27). The cells were maintained in this medium for 10 days and medium changes were performed every second day by replacing half of the volume with fresh medium. FIG. 10 shows the morphology of the cells at day 1, 2, 4, 7, and 10 after transfer of the MCP cells. At day 10 the cells were fixed using PFA and stained using antibodies directed against Brachyury. Based on the morphology of the cells maintained in the B27 medium it appears that the MCP cells can, in appropriate culture conditions, give rise to the basement cell type from which they were originally isolated. This conclusion is further strengthened by the positive immunostaining for Brachyury shown in FIG. 11.

Example 13

Cardiac Differentiation of MCP Cells

Spontaneously contracting cells can be obtained from MCP cells in principally three different ways.
  i) One is by simply isolating spontaneously contracting clusters of loosely adherent MCP cells by mechanical dissection once they have been identified visually.
  ii) Secondly, contracting clusters of free floating MCP cells (i.e., detached MCP cells) can also be isolated by aspiration. Contracting cell clusters isolated by any of these procedures can be transferred and plated in new tissue culture dishes. They attach and continue to proliferate and differentiate and can be maintained in vitro for at least 20 days while maintaining the contractile capacity. FIG. 5 illustrates the morphology of the proliferating and spontaneously contracting clusters.
  iii) Finally, non-beating MCP cells can be isolated and transferred to new dishes in which they adhere and spread. After a few days spontaneous contraction is initiated in a fraction of the isolated and re-plated MCP cell clusters. Cell lines used were SA002, LOTAL002 (passage 34, 42, 55+ED3), SA121, LOTBD121 (passage 156+ED10, 156+ED11) and SA461, LOTBF461 (passage 33).

Example 14

Time-Laps Analysis of Live Cultures of MCP Cells

Basement cells and MCP cells derived from undifferentiated hBS cells (described above) were followed by time-lapse photography. Cells were cultured in differentiation medium for 15 days and before the time-lapse study started, it was replaced by CGM medium. In this example cell line BE002.5 passage 26 was used. The culture was put in a culture chamber (37° C., 5% CO2 and 95% humidity) and photos were taken every fifth minute for 72 hours. The time-lapse technique enables studies of the origin of the MCP cell clusters and to follow them over time. MCP cell clusters spontaneously detached from the basement cells and then attached and plated on the same cells and received their morphology. MCP cells can attach either on other cells or directly on plastic.

Example 15

Characterization of MCP Cells

MCP cells were derived as described above from differentiating hBS cells. Isolated MCP cell clusters were harvested and immediately collected and fixed using PFA for subsequent immunohistochemical evaluation on glass slides using Cytospin according to the manufacturer's instructions. On each glass slide 3-4 MCP cell clusters were collected and at least three individual glass slides were used for each antibody-staining (see below). Cell lines used were SA002, LOTAL002 (passage 55+ED3) and SA002.5, LOTBE002.5 (passage 26).

In order to determine in which manner the MCP cells were distinct from undifferentiated hBS cells, immunohistochemical staining of the fixed MCP cells was performed using antibodies directed against hBS cell markers (SSEA-3, SSEA-4, TRA1-60, TRA-1-81, and Oct-4) and the early differentiation marker SSEA-1. Immunohistochemistry was performed as described before (Noaksson et al Stem Cells 2005). None of these markers were expressed by the MCP cells while undifferentiated hBS cell expressed SSEA-4, TRA-1-81, and Oct-4. SSEA-1 was expressed by early differentiated hBS cells but not by MCP cells. Taken together, these data demonstrate that the MCP cells are phenotypically distinct and different from hBS cells.

Additional markers for differentiated cells were also tested. Antibodies directed against the following antigens were evaluated: vimentin, desmin, α-sarcomeric actin, nestin, and islet-1. Among these, only vimentin was expressed in MCP cells (FIG. 7). Notably, the lack of nestin expression distinguishes these cells from previously described neurospheres.

Table IV summarizes the results from IHC analysis of isolated MCP cells.

TABLE IV

| Antigen marker | Result | Antibody info |
| --- | --- | --- |
| SSEA-4 (undifferentiated hBS cells) | Negative | Mouse anti-SSEA-4 antibody, sc-21704, Santa Cruz biotechnology |
| TRA-1-81 (undifferentiated hBS cells) | Negative | Mouse anti_Tra-1-81 antibody, sc-21706, Santa Cruz Biotechnology |
| Oct-4 (undifferentiated hBS cells) | Negative | Mouse anti-Oct-4 antibody, sc-5279, Santa Cruz Biotechnology |
| SSEA-1 (differentiated hBS cells) | Negative | Mouse anti-SSEA-1 antibody, sc-21702, Santa Cruz Biotechnology |
| Nestin (ectodermal) | Negative | Mouse anti-nestin antibody, 611658, BD Biosciences Pharmingen |
| Vimentin (mesodermal) | Positive | Mouse anti-vimentin antibody, V-6630, Sigma |
| Desmin (mesodermal) | Negative | Mouse anti-desmin antibody, MAB1698, Chemicon |
| α-sarcomeric actin (mesodermal) | Negative | Mouse anti-α-sarcomeric actin antibody, A-2172, Sigma |
| Islet-1 (early cardic marker) | Negative | Mouse anti-islet-1 antibody, 39.4D5, DSHB |

Example 16

Characterization of MCP Cells by Real-Time RT PCR

MCP cells were derived from undifferentiated hBS cells as described above, forced aggregation, example 1. MCP cell clusters were harvested 9-18 days after plating either by mechanical dissection of loosely attached cell clusters using a Stem Cell Cutting Tool or by aspiration of freely floating clusters. These two types of cell clusters could theoretically represent different developmental stages of the MCP cells. The MCP cell cells were transferred to tubes, around 50-200 cells in each tube, and washed with ice cold PBS. The cells were centrifuged at 400×g for 10 minutes. The supernatant was removed and the cell pellet was frozen in liquid nitrogen. The cells were stored in i–80° C. until analysis. Cell lines used for derivation of progenitor cells were SA002, LOTAL002 (passage 24, 27 and 28), SA348 (passage 27) cultured on mouse embryonic fibroblasts (mEF), and E3-SA002 (passage 10) cultured on human foreskin fibroblasts (hFF). Undifferentiated cells (SA002, passage 74, and E3-SA002, passage 10), mixed differentiated cells cultured on mEF (SA002, passage 75, 20 days after plating) and hFF cells were harvested and processed as described above to compare gene expression levels in these samples to MCP cells.

Total RNA was prepared from the cells using the RNeasy micro and mini kit followed by DNase treatment according to the manufacturer's instructions (Qiagen). Synthesis of cDNA was performed with the High Capacity cDNA Reverse Transcription kit (Applied Biosystems). cDNA prepared from samples containing small amounts of cells was preamplified before TaqMan analysis according to the manufacturer's instructions (Applied Biosystems).

In order to get a mRNA finger print of the MCP cells, a panel of genes specific for different types of cells was analyzed with TaqMan real-time RT PCR: stem/progenitor cells (Oct4, Nanog, Flk-1 (KDR), Notch-1 and Islet-1), early cardiac cells (Nkx2.5 and GATA4), cardiomyocytes (Troponin T2), endothelial cells (CD31) and smooth muscle cells (ACTA2). CREBBP was used as an endogenous control. The expression levels of each gene for the MCP cell samples were compared to the reference samples.

The mRNA expression level of both Oct-4 and Nanog was high in undifferentiated cells, but very low in MCP cells as well as mixed differentiated cells or hFF (FIGS. 15A and 16A). The lack of detectable RNA levels in MCP cells of these two genes indicates that the MCP cells from both mEF and hFF culture systems are clearly distinguished from undifferentiated hBS cells.

Flk-1 mRNA is highly expressed specifically in MCP cells compared to both undifferentiated cells and mixed differentiated cells or hFF (FIGS. 15B and 16B). This suggests that Flk-1 (KDR) could be used as a specific marker to selectively identify and/or isolate MCP cells. Notch-1 gene expression levels were also higher in MCP cells compared to undifferentiated cells, hFF, and mixed differentiated cells but the differences were not as striking as for Flk-1 (FIGS. 15A and 16A). Notch-1 is involved in many different signaling pathways and general expression of this gene could therefore be expected in various types of differentiated cells. Gene expression levels of Islet-1 were higher in MCP cells compared to undifferentiated cells. However, islet-1 mRNA levels in mixed differentiated cells and hFF were higher compared to both undifferentiated cells and MCP cells (FIGS. 15A and 16A). This is not unexpected since Islet-1 is implicated in the developmental pathways of many different cells.

Gene expression levels of Nkx2.5 and GATA4, representing early cardiac stages, and Troponin T2, representing the specialized cardiomyocyte, were increased in MCP cells cultured on hFF and mEF compared to undifferentiated hBS cells, hFF feeder cells, and mixed differentiated cells (FIGS. 15B and 16B). The same pattern was seen for CD31, commonly used as endothelial cell marker, in these cells (FIGS. 15B and 16B). For α-smooth muscle actin, a smooth muscle cell marker, the gene expression was higher in the MCP cells compared to undifferentiated hBS cells but lower compared to hFF and mixed differentiated cells (FIGS. 15B and 16B). This is not unexpected since the hFF and mixed differentiated cells contain a substantial proportion of fibroblasts-like cells that also express a-smooth muscle actin. Notably, similar to the expression of cardiac genes in the MCP cells, the mRNA levels of CD31 and α-smooth muscle actin were increased in MCP cells compared to undifferentiated cells. This is indicative of a cardiac/endothelial/smooth muscle progenitor phenotype of the MCP cells. In conclusion, the MCP cells do not express marker genes for undifferentiated hBS cells and they have started to take on different developmental pathways, supporting their multipotent character.

Example 17

Characterization of Cells Differentiated from MCP Cells

MCP cells were derived as described above from undifferentiated hBS cells. The MCP cell clusters were isolated and transferred to new culture dishes. Subsequently, MCP cells were maintained in culture for up to 16 days in differentiation medium. Cells were fixed at various time points and evaluated using immunohistochemistry (Noaksson et al Stem Cells 2005). Cell lines used were SA002, LOTAL002 (passage 48), SA002.5, LOTBE002.5 (passage 42+ED4), SA121, LOTBD121 (passage 156+ED10, 156+ED11) and SA461, LOTBF461 (passage 22).

Table V summarizes the experiments and the results obtained.

TABLE V

| Antigen marker | Days of differentiation* | Result | Antibody info |
|---|---|---|---|
| Vimentin (mesodermal) | 3 | Positive | Mouse anti-vimentin antibody, V-6630, Sigma |
| Desmin (mesodermal) | 3 | Positive | Mouse anti-desmin antibody, MAB1698, Chemicon |
| Brachyury (mesodermal) | 5 | Negative | Rabbit anti-brachyury antibody, sc-20109, Santa Cruz Biotechnology |
| α-sarcomeric actin (mesodermal) | 2 | Few positive colonies | Mouse anti-α-sarcomeric actin antibody, A-2172, Sigma |
|  | 7 | Positive colonies |  |
| Nestin (ectodermal) | 2 | Individual positive cells | Mouse anti-nestin antibody, 611658, BD Biosciences Pharmingen |
|  | 5 | Individual positive cells |  |
|  | 12 | Negative |  |
| GFAP (ectodermal) | 5 | Negative | Rabbit anti-GFAP antibody, Z0334, Dako cytomation |
|  | 6 | Negative |  |
| Islet-1 (early cardiac) | 2 | Negative | Mouse anti-islet-1 antibody, 39.4D5, DSHB |
|  | 5 | Negative |  |
| c-kit (early cardiac stem cell marker) | 2 | Negative | Mouse anti-c-kit antibody, MAB1164, Chemicon |
| GATA-4 (early cardiac) | 3 | Negative | Rabbit anti-GATA-4 antibody, sc-9053, Santa Cruz Biotechnology |
|  | 6 | Weakly positive cells in a few colonies |  |
|  | 7 | Negative |  |
| Nkx2.5 (early cardiac) | 3 | Negative | Rabbit anti-Nkx2.5 antibody, sc-14033, Santa Cruz Biotechnology |
|  | 12 | Negative |  |
|  | 16 | Several positive areas |  |
| Connexin-43 (early cardiac) | 3 | Negative | Mouse anti-connexin-43 antibody, MAB3067, Chemicon |
| Oct-4 (undifferentiated hBS cells) | 3 | Negative | Mouse anti-Oct-4 antibody, sc-5279, Santa Cruz Biotechnology |

*Denotes number of days after isolation and transfer of MCP cell clusters to new culture dishes.

The early appearance of markers of the mesoderm lineage (e.g. dersmin, vimentin, α-sarcomeric actin) suggests that the MCP cells preferentially differentiate towards cell types of this germ layer. In addition, the lack of expression of neural markers (nestin and GFAP), indicates that the MCP cells are distinct from neurosphere cells originally described by Reynolds and Weiss (Reynolds B A, Weiss S (1992) Generation of neurons and astrocytes from isolated cells of the adult mammalian central nervous system. Science 255: 1707-1710). Neurospheres consist predominantly of committed progenitors mixed with differentiated astrocytes and neurons.

Finally, the expression of Nkx2.5 illustrates the capacity of MCP cells to differentiate into early stage cardiomyocytes.

FIG. 8 illustrates the results obtained by immunohistochemical analysis of the differentiated MCP cells.

Example 18

Cryopreservation of MCP Cells

MCP cells derived and isolated as described above can be cryopreserved using closed straws and vitrification as described before (WO2004098285). In addition, traditional slow-freezing could also be an option.

Example 19

Bioreactor Culture

The MCP cells and basement cells may be grown in a 3-D space which may be compartmentalized by e.g. artificial hollow fiber capillary membranes. This system would enable growth of the cells into larger cell masses between the capillaries, and provide an optimized, natural environment by the perfusion of culture medium and gases like oxygen. The closed bioreactor systems may be developed to produce larger amount of cells (up to $10^{11}$ cells), and to support the potential maintenance of functional properties of the cells. Cell isolation via enzyme perfusion would then allow scale-up in closed GMP systems. Cell purification could then be performed using e.g. FACsorting based on e.g. membrane antigen expression or using density gradient media and centrifugation.

Example 20

Separation Techniques

The MCP cells and basement cells may be purified by using antigen detection for surface expressed markers and subsequent FACsorting. Other alternatives for antigen based sorting is to coat culture dishes with a specific antibody and add the cells in culture medium to the dish and let the cells with the right antigen bind in and the remaining cells be discarded and the bound-in cells harvested for further use. This method is sometimes referred to as immunopanning and could also be performed as negative selection, i.e. letting non-wanted cell types bind in to the antigen coated with and save the culture medium with the wanted MCP cells or basement cells in suspension. This approach may just as well be performed on magnetic beads, so called MAC sorting or using column chromatography. Still other methods to purify cells, such as MCP cells or basement cells with specific characteristics include the use of density gradient media for cell separation based on buoyant density or size under centrifugation.

Example 21

Use of MCP and Basement Cells in Regenerative Medicine

Owing to their multipotentiality and capacity to differentiate into spontaneously contracting cardiomyocyte-like cells, both MCP cells and basement cells could prove extremely useful in regenerative medicine. Specifically, the use of MCP cells for treatment of cardiac related diseases can be envisioned. In order to restore function in a heart which have suffered from cardiac infarction it is necessary to replace cardiac myocytes as well as new blood vessels. When clinically compliant hBS cell lines are available it is possible to use these cells for the derivation of MCP cells or basement cells that later can be transplanted and evaluated for the potential use in humans. In the meantime proof-of-principle experimentation can be performed in animal models. Standard models for induction of cardiac infarction in SCID mice can be employed (eg. cryo-damage or LAD ligation) and MCP cells or basement cells injected at the site of injury. The mice are subsequently monitored for shorter (up to 2-3 weeks) or longer (>3 weeks) time periods and cardiac improvements are measured using standard techniques. At the end of the experiments the mice are sacrificed and the hearts collected for subsequent histological evaluation. The engraftment of human cells in the mouse hearts can be measured using antibodies or probes directed against human specific antigens or DNA.

Example 22

Use of MCP Cells and Basement Cells in Regenerative Medicine, Cell Therapy

The MCP cells and basement cells may further be used for treating disorders associated with, for example, necrotic, apoptotic, damaged, dysfunctional or morphologically abnormal myocardium. Such disorders include, but are not limited to, ischemic heart disease, cardiac infarction, rheumatic heart disease, endocarditis, autoimmune cardiac disease, valvular heart disease, congenital heart disorders, cardiac rhythm disorders, and cardiac insufficiency.

The MCP cells and basement cells, no longer being undifferentiated hBS cells as shown by marker analysis and, accordingly, not giving rise to tumour formations in vivo, being able to proliferate and having a potential to differentiate into cardiac cell types (including cardiomyocytes, endothelial cells and smooth muscle cells), may therefore be suitable for treating the majority of cardiac disorders and diseases by reversing, inhibiting or preventing cardiac damage caused by ischemia resulting from myocardial infarction.

In still further aspects the MCP cells and basement cells can be used to treat cardiac disorders characterized by abnormal cardiac rhythm, such as, for example, cardiac arrhythmia.

The treatment is preferably performed by administering a therapeutically effective dose of the cells to the heart of the subject, preferably by injection into the heart. A therapeutically effective dose is an amount sufficient to generate a beneficial or desired clinical result, which dose could be administered in one or more administrations. The injection can be administered into various regions of the heart, depending on the type of cardiac tissue repair required. The administration may be performed using a catheter-based approach after opening up the chest cavity or entry through any suitable blood vessel. The effective dose of cells can be based on factors such as weight, age, physiological status, medical history, infarct size and elapsed time following onset of ischemia. The administration of MCP cells and/or basement cells preferably comprises treating the subject with an immunosuppressive regimen, preferably prior to such administration, so as to inhibit such rejection.

Example 23

Use of MCP Cells and Basement Cells in Drug Discovery

The use of MCP cells or basement cells in drug discovery applications can be extensive and is based on the features of the cells. Here an application for discovering compounds with a potential effect on cardiac regeneration is described. MCP cells or basement cells are derived and isolated from hBS cells and can be transferred to multi-well format culture dishes (e.g. 96- or 384-well plates). Compounds from a library are then added to the cells in the presence of a defined medium (preferentially serum-free). The cells can be maintained in the presence of the compounds for various time points and in different concentrations. The potential effects of the compounds can be monitored by measuring the differentiation, proliferation and functionality of the cells. Specifically, gene expression analysis can be used and expression of genes typically associated with cardiomyogensis can be measured. In addition, reporter gene constructs can be created that allow easy monitoring of for example fluorescent labeled reporter proteins.

Example 24

Use of MCP Cells and Basement Cells in Toxicity Testing

MCP cells and basement cells are derived from hBS cells as described above and further differentiated into spontaneously contracting cardiomyocyte-like cells either before or after plating of the cells in a MEA (Multichannel Systems, Germany). The effects of various compounds or chemicals can be determined by adding the substances directly to the MEA and incubating the cells for different time points. Extracellular field potentials can be determined using the MEA system and deleterious effects measured non-invasively in the cultures. This opens the possibility to study both acute as well as long term effects of the substances. A further improvement of the platform would be to seed the cells directly in to 96-well plates of the QT-screen system (Multichannel Systems, Germany) with the main advantage of being able to run multiple samples simultaneously.

A further application for evaluation of the effect of various chemicals or compounds on development can be envisioned using MCP cells. For example, during the differentiation of MCP cells towards spontaneously contracting cells (cardiomyocyte-like cells) compounds to be tested can be added to the cultures. The effect of the compounds can be determined using a number of different read-outs such as changes in gene- and protein expression as wells as loss of capacity to differentiate into contracting cells.

Example 25

Use of MCP Cells and Basement Cells in Studies of the Molecular Mechanisms Regulating Cardiogenesis The use of both MCP cells and basement cells in basic research can be extensive and is based on the multipotentiality of the cells and their intrinsic capacity to form spontaneously contracting cells similar to cardiomyocytes. For example, MCP cells are derived and isolated from hBS cells and can be transferred to multi-well format culture dishes. The cells can be maintained in different culture conditions for various time points. The potential effects on cardiomyogenesis can be monitored by measuring the differentiation, proliferation and functionality of the MCP cells and/or the basement cells. Specifically, gene expression analysis can be used and expression of genes typically associated with cardiomyogensis can be measured. In addition, reporter gene constructs can be created that allow easy monitoring of for example fluorescent labeled reporter proteins. In addition, siRNA construct and related transfection technologies can be used to study the effects of certain genes on the cardiomyogenic program.

REFERENCES

Heins N, Englund MCO, Sjöblom C et al. Derivation, characterization, and differentiation of human embryonic stem cells. STEM CELLS 2004;22:367-76.
Huber and Zon 1998, 10(2):103-109, Seminars in Immunology
WO03055992, A method for the establishment of a pluripotent human blastocyst-derived stem cell line, Cellartis AB
WO2004098285, Cryopreservation of human blastocyst stem cells by use of a closed straws vitrification method
WO2004099394, A method for the efficient transfer of human blastocyst-derived stem cells from a feeder-supported to a feeder-free culture system
Noaksson K, Zoric N, Zeng X, Rao M S, Hyllner J, Semb H, Kubista M, Sartipy P, Monitoring differentiation of human embryonic stem cells using real-time PCR. Stem Cells. November-December 2005;23(10):1460-7. Epub Aug. 4, 2005.
Norström A, Åkesson K, Hardarson T, Hamberger L, Björquist P, Sartipy P. "Molecular and pharmacological properties of human embryonic stem cell-derived cardiomyocytes." Exp Biol Med (Maywood). December 2006;231(11):1753-62.
Sjogren-Jansson E, Zetterström M, Moya K, Lindqvist J, Strehl R, Eriksson P S. Large-scale propagation of four undifferentiated human embryonic stem cell lines in a feeder-free culture system, Dev Dyn. August 2005;233 (4):1304-14.
Reynolds B A, Weiss S (1992) Generation of neurons and astrocytes from isolated cells of the adult mammalian central nervous system. Science 255: 1707-1710.
Urbanek, et al, Intense myocyte formation from cardiac stem cells in human cardiac hypertrophy PNAS 2003, 100 (18), 10440-45
Laugwitz et al Postnatal isl1+ cardioblasts enter fully differentiated cardiomyocyte lineages. Nature, 2005, 433, 647-653
Messina et al Isolation and expansion of adult cardiac stem cells from human and murine heart Circ Res 2004, 95, 911-921
Beltrami et al Adult cardiac stem cells are multipotent and support myocardial regeneration Cell, 2003,114, 763-776
Cai et al Isl1 identifies a cardiac progenitor population that proliferates prior to differentiation and contributes a majority of cells to the heart Dev Cell 2003, 5, 877-889
Kehat et al Human embryonic stem cells can differentiate into myocytes with structural and functional properties of cardiomyocytes. J Clin Invest, 108: 407-414, 2001
Xu et al Characterization and enrichment of cardiomyocytes derived from human embryonic stem cells Circ Res, 91: 501-508, 2002
He et al Human embryonic stem cells develop into multiple types of cardiac myocytes: action potential characterization. Circ Res, 93: 32-39, 2003
Mummery et al Differentiation of human embryonic stem cells to cardiomyocytes: role of coculture with visceral endoderm-like cells. Circulation, 107: 2733-2740, 2003
WO2005/012510, METHOD FOR THE ISOLATION AND EXPANSION OF CARDIAC STEM CELLS FROM BIOPSY
WO2006/052925, CARDIAC STEM CELLS Items MCP Cells 1. A cell population derived from human blastocyst-derived stem (hBS) cells comprising multipotent cardiac precursor (MCP) cells.
2. A cell population according to item 1, wherein the cell population has at least one of the following characteristics i) at least 1% of the cells exhibit no antigen expression of one or more markers for undifferentiated cell, the marker being selected from the group consisting of SSEA-3, SSEA-4, TRA-1-60, TRA-1-81 and Oct-4,
ii) at least 1% of the cells exhibit no protein expression of one or more of a neural marker such as, e.g., nestin or GFAP
iii) at least 1% of the cells exhibit protein and/or gene expression of one or more of a mesodermal marker such as, e.g., brachyury, vimentin or desmin, and
iv) at least 1% of the cells exhibit no protein expression of one or more early stage cardiac marker such as, e.g., islet-1, cTNI, cTNT, Nkx2.5, alpha-MHC or connexin 43.

3. A cell population according to item 1 or 2, wherein the cell population comprises MCP cells that grow as clusters of small, round and phase-bright cells.

4. A cell population according to item 3, wherein the clusters of MCP cells are either round or elongated in shape.

5. A cell population according to item 3 or 4, wherein the clusters of MCP cells appear as loosely adherent cell clumps that, if grown on basement cells, overlay a monolayer of basement cells.

6. A cell population according to any of the preceding items, wherein the MCP cells have a relatively high nucleus-to-cytoplasma ratio.

7. A cell population according to any of the preceding items, wherein the MCP cells appear as balloons on a string.

8. A cell population according to any of the preceding items, wherein at least 50% of the MCP cells that
   1. grow as clusters of small, round and phase-bright cells,
   2. form clusters of round or elongated shape, that appear as loosely adherent cell clumps that, if grown on basement cells, overlay a monolayer of basement cells,
   3. have a relatively high nucleus-to-cytoplasma ratio, and/or
   4. appear as balloons on a string
   have at least one of the following characteristics
   i) at least 1% of the cells exhibit no antigen expression of one or more markers for undifferentiated cells, the marker being selected from the group consisting of SSEA-3, SSEA-4, TRA-1-60, TRA-1-81 and Oct-4,
   ii) at least 1% of the cells exhibit no protein expression of one or more of a neural marker such as, e.g., nestin or GFAP
   iii) at least 1% of the cells exhibit protein and/or gene expression of one or more of a mesodermal marker such as, e.g., brachyury, vimentin or desmin, and
   iv) at least 1% of the cells exhibit no protein and/or gene expression of one or more early stage cardiac marker such as, e.g., islet-1, cTNI, cTNT, Nkx2.5, alpha-MHC or connexin 43.

9. A cell population according to item 8, wherein at least 50% of the MCP cells have at least two of the four characteristics.

10. A cell population according to item 8 or 9 wherein at least 50% of the MCP cells have at least three of the four characteristics.

11. A cell population according to any of items 8-10, wherein at least 50% of the MCP cells have all four characteristics.

12. A cell population according to any of items 8-11, wherein characteristics i), ii), iii) and/or iv) are valid for at least 55% such as, e.g., at least 60%, at least 65%., at least 70%, at least 75%, at least 80%, at least 85%, at least 90% or at least 95% of the cells.

13. A cell population according to any of the preceding items, wherein the cell population has at least characteristic i).

14. A cell population according to any of the preceding items, wherein the cell population has at least characteristic i) for at least two such as at least three or at least four of the markers mentioned in i).

15. A cell population according to item 14, wherein the cell population has at least characteristic i) for all markers mentioned in i).

16. A cell population according to any of the preceding items, wherein the cell population has at least characteristic ii) for both markers mentioned in ii).

17. A cell population according to any of the preceding items, wherein the cell population has at least characteristic iii) for two or three of the markers mentioned in iii).

18. A cell population according to any of the preceding items, wherein the cell population has at least characteristic iv) for at least 2 such as, e.g., 2, 3, 4, 5 or 6 of the markers mentioned in iv).

19. A cell population according to any of the preceding items, wherein the cell population has at least two of the four characteristics.

20. A cell population according to any of the preceding items, wherein the cell population has at least three of the four characteristics.

21. A cell population according to any of the preceding items, wherein the cell population has all four characteristics.

22. A cell population according to any of the preceding items, wherein characteristic i) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

23. A cell population according to any of the preceding items, wherein characteristic ii) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

24. A cell population according to any of the preceding items, wherein characteristic iii) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

25. A cell population according to any of the preceding items, wherein characteristic iv) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

26. A cell population according to any of the preceding items, wherein characteristic i), ii), iii) and/or iv) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

27. A cell population according to any of the preceding items, the cell population being xeno-free.

Differentiated MCP Cells

28. A cell population according to any of the preceding items having at least one of the following characteristics after being subjected to differentiation by plating and using a differentiation medium for a time period of at least 5 days
    i) at least 1% of the cells exhibit protein and/or gene expression of one ore more mesodermal markers such as, e.g., brachyury, vimentin or desmin, ii) at least 1% of the cells exhibit protein and/or gene expression of one ore more cardiac markers such as, e.g., islet-1, GATA-4, Nkx2.5, cTNI, cTNT or connexin 43, iii) at least 1% of the cells exhibit no antigen expression of one or more markers for undifferentiated stem cells, the marker being selected from the group consisting of SSEA-3, SSEA-4, TRA-1-60, TRA-1-81 and Oct-4.

29. A cell population according to items 28, wherein the cell population after subjection to differentiation has at least characteristic i).

30. A cell population according to item 28 or 29, wherein the cell population after subjection to differentiation has at least characteristic i) for two or three of the markers mentioned in i).

31. A cell population according to any of items 28-30, wherein the cell population after subjection to differentiation has at least characteristic ii) for at least 2 such as, e.g., 2, 3, 4, 5 or 6 of the markers mentioned in ii).

32. A cell population according to any of items 28-31, wherein the cell population after subjection to differentiation has at least characteristic iii) for at least 2 such as, e.g., 2, 3, 4 or 5 of the markers mentioned in iii).

33. A cell population according to any of items 28-32, wherein the cell population after subjection to differentiation has at least two of the three characteristics.

34. A cell population according to any of items 28-33, wherein the cell population after subjection to differentiation has all three characteristics.

35. A cell population according to any of items 28-34, wherein characteristic i) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

36. A cell population according to any of items 28-35, wherein characteristic ii) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

37. A cell population according to any of items 28-36, wherein characteristic iii) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

38. A cell population according to any of items 28-37, wherein characteristic i), ii) and/or iii) is valid for at least 2% such as, e.g., at least 5%, at least 10%, at least 15%, at least 20%, at least 25%, at least 30%, at least 40%, at least 50%, at least 60%, at least 70%, at least 80%, at least 85%, at least 90% or at least 95% of the cells.

Basement Cells

39. A cell population derived from human blastocyst-derived stem (hBS) cells, the cell population comprising basement cells.

40. A cell population according to item 39, wherein the cell population has at least one of the following characteristics
i) at least 1% of the cells exhibit protein and/or gene expression of brachury
ii) at least 1% of the cells exhibit protein and/or gene expression of alpha-sarcomeric actin,
iii) at least 1% of the cells exhibit no protein expression of vimentin, and
iv) at least 1% of the cells exhibit no protein expression of desmin
v) at least 1% of the cells exhibit no antigen expression of one or more markers for undifferentiated cell, the marker being selected from the group consisting of SSEA-3, SSEA-4, TRA-1-60, TRA-1-81 and Oct-4.

41. A cell population according to item 39 or 40, wherein the basement cells have morphology with similarities to primitive endoderm and the cells are epithelial-like.

42. A cell population according to any of items 39-41, wherein the basement cells are phase-dark and well demarcated as evidenced by light microscopy.

43. A cell population according to any of items 39-42, wherein the basement cells have an angular shape as evidenced by light microscopy.

44. A cell population according to any of items 39-43, wherein at least 5% of the basement cells that
1. have a morphology with similarities to primitive endoderm,
2. are epithelial like,
3. are phase-dark and well demarcated as evidenced by light microscopy, and/or
4. have an angular shape as evidenced by light microscopy have at least one of the following characteristics
i) at least 1% of the cells exhibit protein and/or gene expression of brachury
ii) at least 1% of the cells exhibit protein and/or gene expression of alpha-sarcomeric actin,
iii) at least 1% of the cells exhibit no protein expression of vimentin, and
iv) at least 1% of the cells exhibit no protein expression of desmin
v) at least 1% of the cells exhibit no antigen expression of one or more markers for undifferentiated cell, the marker being selected from the group consisting of SSEA-3, SSEA-4, TRA-1-60, TRA-1-81 and Oct-4

45. A cell population according to item 44, wherein at least 5% of the basement calls have at least two of the five characteristics.

46. A cell population according to item 45, wherein the two characteristics are i) and iv).

47. A cell population according to any of items 44-46, wherein at least 5% of the basement calls have at least three of the five characteristics.

48. A cell population according to any of items 44-47, wherein at least 5% of the basement calls have at least four of the five characteristics.

49. A cell population according to any of items 44-48, wherein at least 5% of the basement calls have all five characteristics.

50. A cell population according to any of items 44-49, wherein the characteristics are valid for at least 10% such as, e.g., at least 20%, at least 30%, at least 40%, at least 50%, at least 60%, at least 70%, at least 80%, at least 85%, at least 90% or at least 95% of the cells.

51. A cell population according to any of items 39-50, wherein the cell population has at least characteristic i).

52. A cell population according to any of items 39-51, wherein the cell population has at least two of the five characteristics.

53. A cell population according to item 52, wherein the two characteristics are i) and iv).

54. A cell population according to any of items 39-53, wherein the cell population has at least three of the five characteristics.

55. A cell population according to any of items 39-54, wherein the cell population has at least four of the five characteristics.

56. A cell population according to any of items 39-55, wherein the cell population has all five characteristics.
57. A cell population according to any of items 39-56, wherein characteristic i) is valid for at least 5% such as, e.g., at least 10%, at least 15%, at least 20%, at least 25%, at least 30%, at least 40% or at least 50% of the cells.
58. A cell population according to any of items 39-57, wherein characteristic ii) is valid for at least 5% such as, e.g., at least 10%, at least 15%, at least 20%, at least 25%, at least 30%, at least 40% or at least 50% of the cells.
59. A cell population according to any of items 39-58, wherein characteristic iii) is valid for at least 5% such as, e.g., at least 10%, at least 15%, at least 20%, at least 25%, at least 30%, at least 40% or at least 50% of the cells.
60. A cell population according to any of items 39-59, wherein characteristic iv) is valid for at least 5% such as, e.g., at least 10%, at least 15%, at least 20%, at least 25%, at least 30%, at least 40% or at least 50% of the cells.
61. A cell population according to any of items 39-60, wherein characteristic v is valid for at least 5% such as, e.g., at least 10%, at least 15%, at least 20%, at least 25%, at least 30%, at least 40% or at least 50% of the cells.
62. A cell population according to any of items 39-61, wherein characteristic i), ii), iii), iv) and/or v) is valid for at least 5% such as, e.g., at least 10%, at least 15%, at least 20%, at least 25%, at least 30%, at least 40% or at least 50% of the cells.
63. A cell population according to any of items 39-62, the cell population being xeno-free.
64. Use of a cell population as defined in any of items 39-63 for providing MCP cells
65. Use of a cell population as defined in any of the preceding items for use in a drug discovery process.
66. Use of a cell population as defined in any of items 1-63 in in vitro models for studying drugs with potential effect on cardiac cell types.
67. Use of a cell population as defined in any of items 1-63 in in vitro models for studying cardiogenesis, such as, e.g., early cardiogenesis.
68. Use of a cell population as defined in any of items 1-63 in in vitro models for studying human cardiodegenerative disorders.
69. Use of a cell population as defined in any of items 1-63 for in vitro cardiotoxicity testing.
70. Use of a cell population as defined in any of items 1-63 in regenerative medicine.
71. Use of a cell population as defined in any of items 1-63 in medicine.
72. Use of a cell population as defined in any of items 1-63, for the manufacture of a medicinal product for the prevention and/or treatment of pathologies and/or diseases caused by tissue degeneration, such as, e.g., the degeneration of cardiac tissue.
73. Use of a cell population as defined in any of items 1-63 for the manufacture of a medicinal product for the treatment of cardiac disorders.
74. Use of a cell population as defined in any of items 1-63 for the manufacture of a medicinal product for the prevention and/or treatment of cardiac disorders such as disorders related to necrotic, apoptotic, damaged, dysfunctional or morphologically abnormal myocardium.
75. Use of a cell population as defined in any of items 1-63 for the manufacture of a medicinal product for the treatment and/or prevention of diseases such as ischemic heart disease, cardiac infarction, rheumatic heart disease, endocarditis, autoimmune cardiac disease, valvular heart disease, congenital heart disorders, cardiac rhythm disorders, and/or cardiac insufficiency. .
76. Use of one or more cells from a cell population as defined in any items 1-63 for obtaining cardiomyocyte-like cells.
77. Use of one or more cells from a cell population as defined in any items 1-63 for studying maturation towards cardiomyocyte-like cells.
78. A method for screening a compound for cardiocellular toxicity, comprising exposing cells from a cell population as defined in any items 1-63 to the compound, and determining whether the compound is toxic to the cell.
79. A method for screening a compound for its ability to modulate cardiocellular function, comprising exposing cells from a cell population as defined in any of items 1-63 to the compound, determining any phenotypic or metabolic changes in the cells that result from contact with the compound, and correlating the change with an ability to modulate cardiocellular function.

Method Basement Cells and MCP Cells

80. A method for the preparation of a cell population as defined in any of items 39-63 comprising the steps of
    i) culturing of one or more pieces of colonies or colonies of undifferentiated hBS cell in a differentiation medium in a suspension culture of from about 1 to about 10 days such as from about 1 to about 6 days,
    ii) transferring the thus cultured cells to a culture vessel for continued proliferation and differentiation,
    iii) identifying basement cells by morphological criteria in light microscope and/or relevant marker identification as defined herein,
    iv) optionally, isolating the thus obtained basement cells, and
    v) optionally, repeating steps ii)-iv)
81. A method for the preparation of a cell population as defined in any of items 1-39 comprising steps i)-iii) as defined in item 80 and the further steps of
    vi) culturing the basement cells until MCP cells appears as evidenced by light microscope and/or relevant marker identification as defined herein,
    vii) isolating the thus obtained MCP cells.
82. A method according to item 81 further comprising sub-culturing of the MCP cells e.g. for storage, for use for cardiac differentiation, for characterization, for use in drug discovery, for use in toxicity testing, for use in regenerative medicine and/or for obtaining basement cells.
83. A method according to item 81 further comprising de novo isolation of MCP cells.
84. A method according to any of items 80-83, wherein step i) is performed using pieces of undifferentiated colonies of hBS cells.
85. A method according to any of items 80-84, wherein the suspension culture in step i) is performed in serum such as FBS or human serum.
86. A method according to item 85, wherein the concentration of serum is at least 2% such as, e.g., from about 2% to about 30%, from about 5% to about 25% or about 20%.
87. A method according to any of items 80-86, wherein step i) is performed for a time period of from about 1 to abut 6 days such as, e.g., from about 1 to about 4 days, from about 1 to about 3 days or from about 1 to about 2 days.
88. A method according to any of items 80-87, wherein step ii) is performed in the same or in a different medium.
89. A method according to item 88, wherein the medium contains serum such as FBS or human serum or it is a serum-free medium.

90. A method according to item 89, wherein the concentration of serum, if present, is at least 2% such as, e.g., from about 2% to about 30%, from about 5% to about 25% or about 20%.

91. A method according to any of items 80-90, wherein step ii) is performed by plating the cells directly on a surface of the culture vessel or on extracellular matrix components.

92. A method according to any of items 80-91, wherein step ii) is performed for a time period of from about 2 to about 20 days such as e.g. from about 2 to abut 15 days, from about 2 to about 10 days, from about 2 to about 6 days or from about 2 to about 4 days.

93. A method according to any of items 80-92, wherein step iv) is performed for a time period of from about 2 to abut 25 days such as, e.g., from about 2 to about 20 days, from about 2 to about 15 days, from about 2 to abut 10 days, from about 2 to about 5 days or from about 2 to about 4 days.

94. A method comprising
i) plating MCP cells on a surface in the presence of a differentiation factor and/or medium to obtain differentiated MCP cells.

Kit

95. A kit comprising i) a cell population as defined in any of items 1-63, ii) one or more maturation factors and/or a maturation culture medium, and iii) optionally, an instruction for use.

96. A kit according to item 95, wherein the maturation culture medium is selected from the group consisting of Vitro-HES™, VitroHES™ supplemented with bFGF, autologuous pre-conditioned VitroHES™, CGM medium, and other cardiac specific culture media.

97. A kit according to item 95 or 96, wherein the one or more maturation factors are selected from the group consisting of FGF, such as bFGF, BMP, 5-aza deoxycytidine, DMSO, retinoic acid, ascorbic acid, and ASA 98. A kit according to any of items 95-97, further comprising tools for monitoring maturation.

99. A kit according to item 98, wherein the tools for monitoring maturation comprises
i) PCR primers against at least three, such as, e.g. at least four or at least five of the genes coding for expression markers selected from the group consisting of markers for undifferetnatiated hBS cells, desmin, alpha-sarcomeric actin, Brachyury, Nestin, GFAP, Islet-1, Nkx2.5, GATA-4, cTnI, cTnT, a-MHC, and connexin-43, and
ii) a user's manual.

100. A kit according to any of items 98 or 99, wherein the tools for monitoring maturation comprises
i) antibodies against at least three, such as, e.g. at least four or at least five of the expression marker antigens selected from the group consisting of markers for undifferetnatiated hBS cells, desmin, alpha-sarcomeric actin, Brachyury, Nestin, GFAP, Islet-1, Nkx2.5, GATA-4, cTnI, cTnT, a-MHC, and connexin-43, and
ii) a user's manual.

101. A kit for regenerative medicine comprising
i) basement and/or MCP cells
ii) optionally, factors for driving differentiation in vitro and or in vivo
iii) tools for administration of the cells to a patient or cells in an administrative form, such as in a ready-to-use syringe.

The invention claimed is:

1. An isolated population of basement cells, wherein said basement cells are phase-dark as evidenced by light microscopy and have all of the following seven characteristics:
    i) the cells exhibit protein and/or gene expression of brachury,
    ii) the cells exhibit protein and/or gene expression of alpha-sarcomeric actin,
    iii) the cells exhibit no protein expression of vimentin,
    iv) the cells exhibit no protein expression of desmin,
    v) the cells exhibit no antigen expression of SSEA-3, SSEA-4, TRA-1-60, TRA-1-81, and Oct-4,
    vi) the cells exhibit gene expression of Basonuclin 1 (BNC1), nephronectin (NPNT), fibrinogen alpha chain (FGA), annexin A8 (ANXA8), matrix Gla protein (MGP), zona pellucida glycoprotein 4 (ZP4), thrombomodulin (THBD), homeobox B7 (HOXB7), heart and neural crest derivatives expressed 1 (HAND1), desmocollin 3 (DSC3), interleukin 6 signal transducer (IL6ST), aquaporin 1 (AQP1), Frizzled-related protein (FRZB), bradykinin receptor B1 (BDKRB1), growth hormone receptor (GHR) and kinase insert domain receptor (Flk-1) (KDR), and
    vii) the cells have down regulated gene expression of oct-4 and nanog compared to undifferentiated hBS cells.

2. An isolated basement cell which is phase-dark as evidenced by light microscopy and has all of the following seven characteristics
    i) the cell exhibits protein and/or gene expression of brachury,
    ii) the cell exhibits protein and/or gene expression of alpha-sarcomeric actin,
    iii) the cell exhibits no protein expression of vimentin,
    iv) the cell exhibits no protein expression of desmin,
    v) the cell exhibits no antigen expression of SSEA-3, SSEA-4, TRA-1-60, TRA-1-81, and Oct-4,
    vi) the cell exhibits gene expression of Basonuclin 1 (BNC1), nephronectin (NPNT), fibrinogen alpha chain (FGA), annexin A8 (ANXA8), matrix Gla protein (MGP), zona pellucida glycoprotein 4 (ZP4), thrombomodulin (THBD), homeobox B7 (HOXB7), heart and neural crest derivatives expressed 1 (HAND1), desmocollin 3 (DSC3), interleukin 6 signal transducer (IL6ST), aquaporin 1 (AQP1), Frizzled-related protein (FRZB), bradykinin receptor B1 (BDKRB1), growth hormone receptor (GHR) and kinase insert domain receptor (Flk-1) (KDR), and
    vii) the cell has down regulated gene expression of oct-4 and nanog compared to an undifferentiated hBS cell.

* * * * *